(12) United States Patent
Lachenbruch et al.

(10) Patent No.: US 10,548,788 B2
(45) Date of Patent: Feb. 4, 2020

(54) PERSON SUPPORT SYSTEMS WITH COOLING FEATURES

(71) Applicant: Hill-Rom Services, Inc., Batesville, IN (US)

(72) Inventors: Charles A. Lachenbruch, Batesville, IN (US); Varad Narayan Srivastava, Loveland, OH (US); David Lance Ribble, Indianapolis, IN (US); Rachel L. Williamson, Batesville, IN (US); David Lawrence Bedel, Oldenburg, IN (US); Andrew David Clark, Waltham, MA (US); Steven D. Baker, Beaverton, OR (US); John V. Harmeyer, Cleves, OH (US); Ben Hertz, Acton, MA (US); Todd P. O'Neal, Fairfield, OH (US)

(73) Assignee: HILL-ROM SERVICES, INC., Batesville, IN (US)

( * ) Notice: Subject to any disclaimer, the term of this patent is extended or adjusted under 35 U.S.C. 154(b) by 590 days.

(21) Appl. No.: 15/348,080

(22) Filed: Nov. 10, 2016

(65) Prior Publication Data
US 2017/0135884 A1 May 18, 2017

Related U.S. Application Data

(60) Provisional application No. 62/255,147, filed on Nov. 13, 2015.

(51) Int. Cl.
*A61G 7/05* (2006.01)
*A61G 7/057* (2006.01)
(Continued)

(52) U.S. Cl.
CPC ............ *A61G 7/057* (2013.01); *A61B 5/01* (2013.01); *A61B 5/6892* (2013.01);
(Continued)

(58) Field of Classification Search
CPC ....................................................... A61G 7/05
(Continued)

(56) References Cited

U.S. PATENT DOCUMENTS

| | | | |
|---|---|---|---|
| 4,057,861 A | 11/1977 | Howorth | |
| 5,837,002 A | 11/1998 | Augustine et al. | |

(Continued)

FOREIGN PATENT DOCUMENTS

| | | |
|---|---|---|
| TW | 201407164 A | 2/2014 |
| WO | 2012051628 A1 | 4/2012 |

(Continued)

OTHER PUBLICATIONS

Doty et al., "The Wearable Multimodal Monitoring System: A platform to study falls and near-falls in the real-world", Springer International Publishing, Switzerland, pp. 412-422, DOI: 10.1007/978-3-319-20913-5_38, 2015.

(Continued)

*Primary Examiner* — Fredrick C Conley
(74) *Attorney, Agent, or Firm* — Dinsmore & Shohl LLP

(57) ABSTRACT

Embodiments provide a person support system including support pads having cooling features. According to one embodiment, a person support system may include a longitudinal frame comprising at least one side rail. A support pad may be positioned on the longitudinal frame. The support pad may comprise a thermally conductive core portion comprising a support matrix and at least one thermally conductive element. A cooling source may be thermally coupled to the thermally conductive core portion through the side rail with a connector comprising thermally conductive fibers. The cooling source may draw heat from the thermally conductive core portion through the at least one thermally conductive element and the thermally conductive fibers of (Continued)

the connector thereby cooling at least the thermally conductive core portion of the support pad.

47 Claims, 28 Drawing Sheets

(51) Int. Cl.
*A61B 5/00* (2006.01)
*A61B 5/01* (2006.01)
*A61G 13/12* (2006.01)
*A61F 7/00* (2006.01)
*A61G 13/00* (2006.01)
*A61G 13/04* (2006.01)
*A61G 13/06* (2006.01)
*A61G 13/10* (2006.01)

(52) U.S. Cl.
CPC .......... *A61F 7/0053* (2013.01); *A61F 7/0097* (2013.01); *A61G 13/0054* (2016.11); *A61G 13/04* (2013.01); *A61G 13/06* (2013.01); *A61G 13/104* (2013.01); *A61G 13/12* (2013.01); *A61G 13/126* (2013.01); *A61G 13/127* (2013.01); *A61B 5/4836* (2013.01); A61F 2007/0056 (2013.01); A61F 2007/0075 (2013.01); A61F 2007/0086 (2013.01); A61F 2007/0096 (2013.01); A61G 2203/10 (2013.01); A61G 2203/46 (2013.01); A61G 2205/60 (2013.01); A61G 2210/50 (2013.01); A61G 2210/70 (2013.01)

(58) Field of Classification Search
USPC .......................................... 5/724, 726, 652.1
See application file for complete search history.

(56) References Cited

U.S. PATENT DOCUMENTS

| | | |
|---|---|---|
| 6,210,427 B1 | 4/2001 | Augustine et al. |
| 6,840,955 B2 | 1/2005 | Ein |
| 7,273,490 B2 | 9/2007 | Lachenbruch |
| 7,727,267 B2 | 6/2010 | Lachenbruch |
| 7,784,126 B2 | 8/2010 | Meissner et al. |
| 7,857,507 B2 | 12/2010 | Quinn et al. |
| 7,942,825 B2 | 5/2011 | Ranganathan et al. |
| 8,087,254 B2 | 1/2012 | Arnold |
| 8,328,420 B2 | 12/2012 | Abreu |
| 8,475,368 B2 | 7/2013 | Tran et al. |
| 8,606,344 B2 | 12/2013 | Dimaio et al. |
| 8,620,625 B2 | 12/2013 | Sing et al. |
| 8,663,106 B2 | 3/2014 | Stivoric et al. |
| 8,716,629 B2 | 5/2014 | Klewer et al. |
| 8,800,078 B2 | 8/2014 | Lachenbruch et al. |
| 8,907,287 B2 | 12/2014 | Vanderpohl |
| 8,939,912 B2 | 1/2015 | Turnquist et al. |
| 9,089,462 B1 | 7/2015 | Lafleche |
| 9,132,031 B2 | 9/2015 | Levinson et al. |
| 9,596,944 B2 | 3/2017 | Makansi et al. |
| 2005/0149153 A1 | 7/2005 | Nakase |
| 2005/0168941 A1 | 8/2005 | Sokol et al. |
| 2006/0202816 A1 | 9/2006 | Crump et al. |
| 2007/0135878 A1* | 6/2007 | Lachenbruch ......... A61G 7/057 607/108 |
| 2008/0018480 A1 | 1/2008 | Sham |
| 2008/0077201 A1 | 3/2008 | Levinson et al. |
| 2009/0069642 A1 | 3/2009 | Gao et al. |
| 2010/0274331 A1* | 10/2010 | Williamson ....... A61G 7/05738 607/104 |
| 2010/0298658 A1 | 11/2010 | Mccombie et al. |
| 2011/0107514 A1* | 5/2011 | Brykalski ............ A47C 21/044 5/421 |
| 2013/0066237 A1 | 3/2013 | Smotrich et al. |
| 2013/0090571 A1 | 4/2013 | Nourani et al. |
| 2014/0237719 A1 | 8/2014 | Brykalski et al. |
| 2014/0260331 A1 | 9/2014 | Lofy et al. |
| 2014/0323816 A1 | 10/2014 | Soderberg et al. |
| 2015/0051673 A1 | 2/2015 | Rivas Tapia |
| 2015/0230974 A1 | 8/2015 | Pistor et al. |
| 2015/0290065 A1 | 10/2015 | Augustine et al. |
| 2015/0323388 A1 | 11/2015 | Kostic et al. |
| 2016/0338500 A1 | 11/2016 | Malzl |

FOREIGN PATENT DOCUMENTS

| | | |
|---|---|---|
| WO | 2014047310 A1 | 3/2014 |
| WO | 2015074007 A1 | 5/2015 |
| WO | 20150148225 A2 | 10/2015 |
| WO | 20150164456 A2 | 10/2015 |

OTHER PUBLICATIONS

Jiang, "A Smart and Mimimum-Intrusive Monitoring Framework Design for Health Assessment of the Elderly", Doctoral dissertation, University of Cincinnati, pp. 1-124, 2015.

Hill-Rom, "VersaCare® Med Surg Bed" <online: http://www.hill-rom.com/usa/products/category/hospital-beds/versacare-med-surg-beds/>.

Laird, "Penn Medicine tests continuous, wearable patient monitoring", <online: http://www.summitdata.com/blog/penn-medicine-tests-wearable-patient-monitor-hospital/>, 2015.

Appelboom G et al., "The Promise of Wearable Activity Sensors to Define Patient Recovery", Journal of Clinical Neuroscience, DOI: 10.1016/j.jocn.2013.12.003, 2014.

CSZ, Gelli-Roll®, "Reusable Warming and Cooling Gel Pad", <online: http://www.cszmedical.com/gelli-roll>.

Bard Medical, "Arctic Sun® 5000 Temperature Management System", <online: http://www.bardmedical.com/Prescriptive/?productID=5971&p=6564>.

Lanata et al., "Complexity Index from a Personalized Wearable Monitoring System for Assessing Remission in Mental Health", Journal of Latex Class Files, vol. 11, No. 4, 2012.

Extended European Search Report dated Apr. 13, 2017 relating to EP Patent Application No. 16198283.0.

* cited by examiner

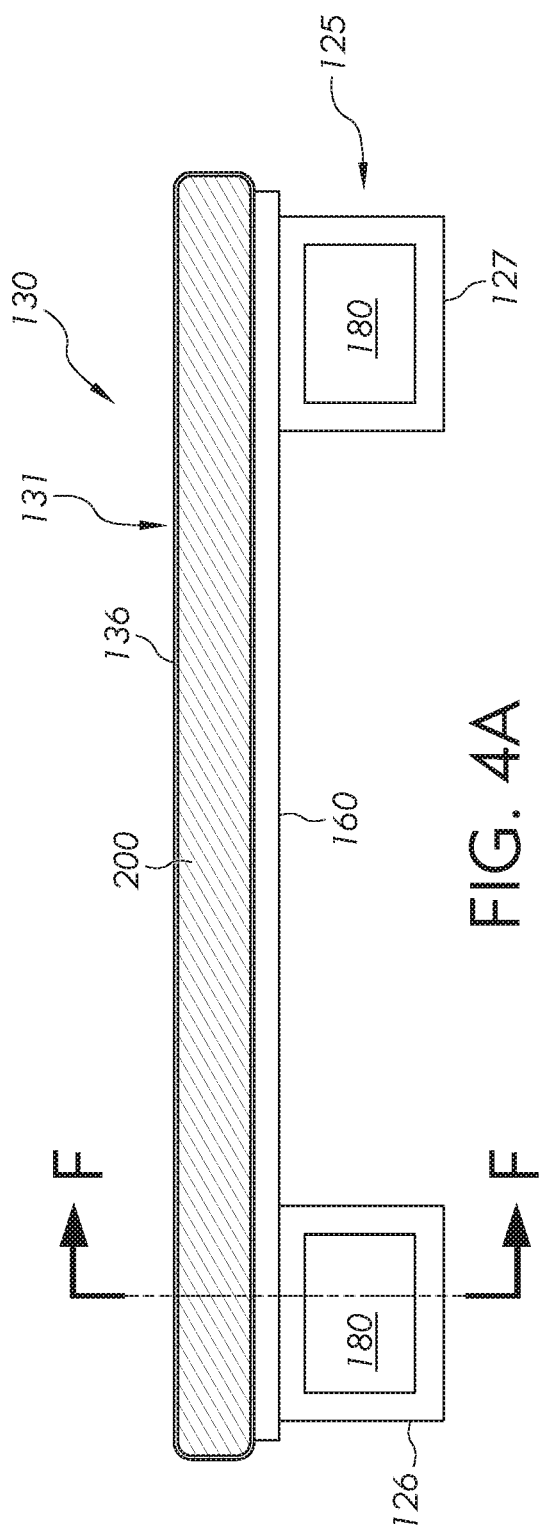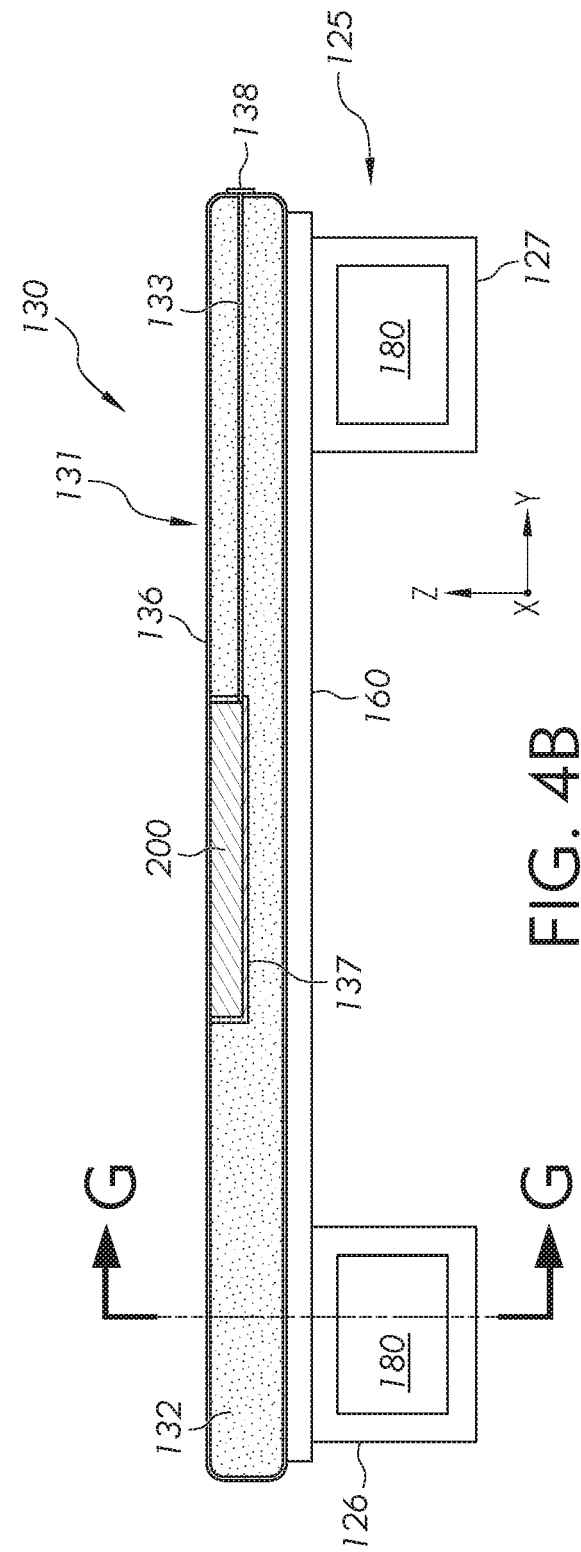

PERSON SUPPORT SYSTEMS WITH COOLING FEATURES

CROSS REFERENCE TO RELATED APPLICATIONS

The present application claims priority to U.S. Provisional Patent Application No. 62/255,147 filed Nov. 13, 2015 and entitled "Support Surfaces With Cooling Features," the entirety of which is incorporated by reference herein.

TECHNICAL FIELD

The present specification generally relates to person support systems, and more specifically, to person support systems having cooling features.

BACKGROUND

Conventionally, a subject may be positioned on a support surface during a medical procedure. The support surface is generally the upper surface of a surgical table, such as a spine table or standard operating room (OR) table, and may include a number of pads to provide support to the subject. The pads provide cushioning to the subject and may facilitate positioning the subject so as to provide access to a portion of the subject's anatomy that is to be operated on. For example, in the case of a spine table, the pads of the support surface may be used to position the subject on the spine table such that the subject's spine is curved or arched, thereby separating the vertebrae.

During a surgical operation the subject may be maintained in one position on the support surface for an extended period of time. As such, certain areas of the subject's anatomy in contact with the surface may be subject to relatively high, localized pressure. For example, when a subject is in a supine position on the surface, portions of the subject's posterior skin, such as the subject's sacral area, buttocks, scapular areas, and/or heels, may be subject to relatively high, localized pressure due to the subject's own body weight. These areas of localized pressure may be different depending on the orientation of the subject on the surface. For example, when the subject is in the prone position on the surface, the areas of localized pressure may be along the anterior skin of the subject. The areas of relatively high localized pressure may be prone to the development of pressure ulcers due to the localized increases in pressure. The development of pressure ulcers may be further exacerbated by heat and the presence of moisture, such as perspiration, trapped between the skin and the surface for extended periods of time.

Accordingly, a need exists for alternative support pads for support surfaces of person support systems, such as surgical tables or the like, which mitigate the development of pressure ulcers in subjects positioned on the support pads.

SUMMARY

According to one embodiment, a person support system may include a longitudinal frame comprising at least one side rail. A support pad may be positioned on the longitudinal frame. The support pad may comprise a thermally conductive core portion comprising a support matrix and at least one thermally conductive element. A cooling source may be thermally coupled to the thermally conductive core portion through the side rail with a connector comprising thermally conductive fibers. The cooling source may draw heat from the thermally conductive core portion through the at least one thermally conductive element and the thermally conductive fibers of the connector thereby cooling at least the thermally conductive core portion of the support pad.

According to another embodiment, a subject cooling system may include a support pad comprising a core part and at least one recess formed in the core part. The recess may extend through a top surface of the support pad. The system may further include a foam plug having a shape and a size corresponding to the recess formed in the core part of the support pad. In addition, the system may include a set of thermally conductive core portions. Each thermally conductive core portion of the set of thermally conductive core portions may have a shape and a size corresponding to the recess formed in the core part of the support pad. Each thermally conductive core portion of the set of thermally conductive core portions may have different cooling characteristics than at least one other thermally conductive core portion in the set of thermally conductive core portions. The foam plug and each thermally conductive core portion of the set of thermally conductive core portions may be interchangeably insertable into the at least one recess formed in the core part of the support pad.

According to another embodiment, a support pad for a person support system may include a thermally conductive core portion that includes a support matrix and a plurality of thermally conductive elements formed from thermally conductive materials, such as thermally conductive particles or the like, disposed on or in the support matrix and arranged to conduct heat away from a top surface of the support matrix. The thermally conductive core portion may further include at least one thermal transport layer thermally coupled to the support matrix and configured to conduct heat from the support matrix. A cover material may envelope the thermally conductive core portion.

According to another embodiment, a support pad for a person support system may include a thermally conductive core portion comprising a support matrix. An array of thermally conductive fibers may be disposed in the support matrix and arranged to conduct heat away from a top surface of the support pad. At least a portion of the array of thermally conductive fibers extend from at least one of a side surface of the support matrix and a bottom surface of the support matrix.

According to another embodiment, a support pad for a person support system may include a thermally conductive core portion comprising a support matrix. A plurality of thermally conductive particles and/or thermally absorptive particles may be dispersed in the support matrix. The support pad may further include at least one thermal transport layer thermally coupled to the support matrix and configured to conduct heat from the support matrix.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

Referring now to the illustrative examples in the drawings, wherein like numerals represent the same or similar elements throughout:

FIG. 4A schematically depicts a cross-section of a support pad for a person support system in accordance with one or more embodiments described herein;

FIG. 4B schematically depicts a cross-section of a support pad for a person support system in accordance with one or more embodiments described herein;

DETAILED DESCRIPTION

Figure 1:
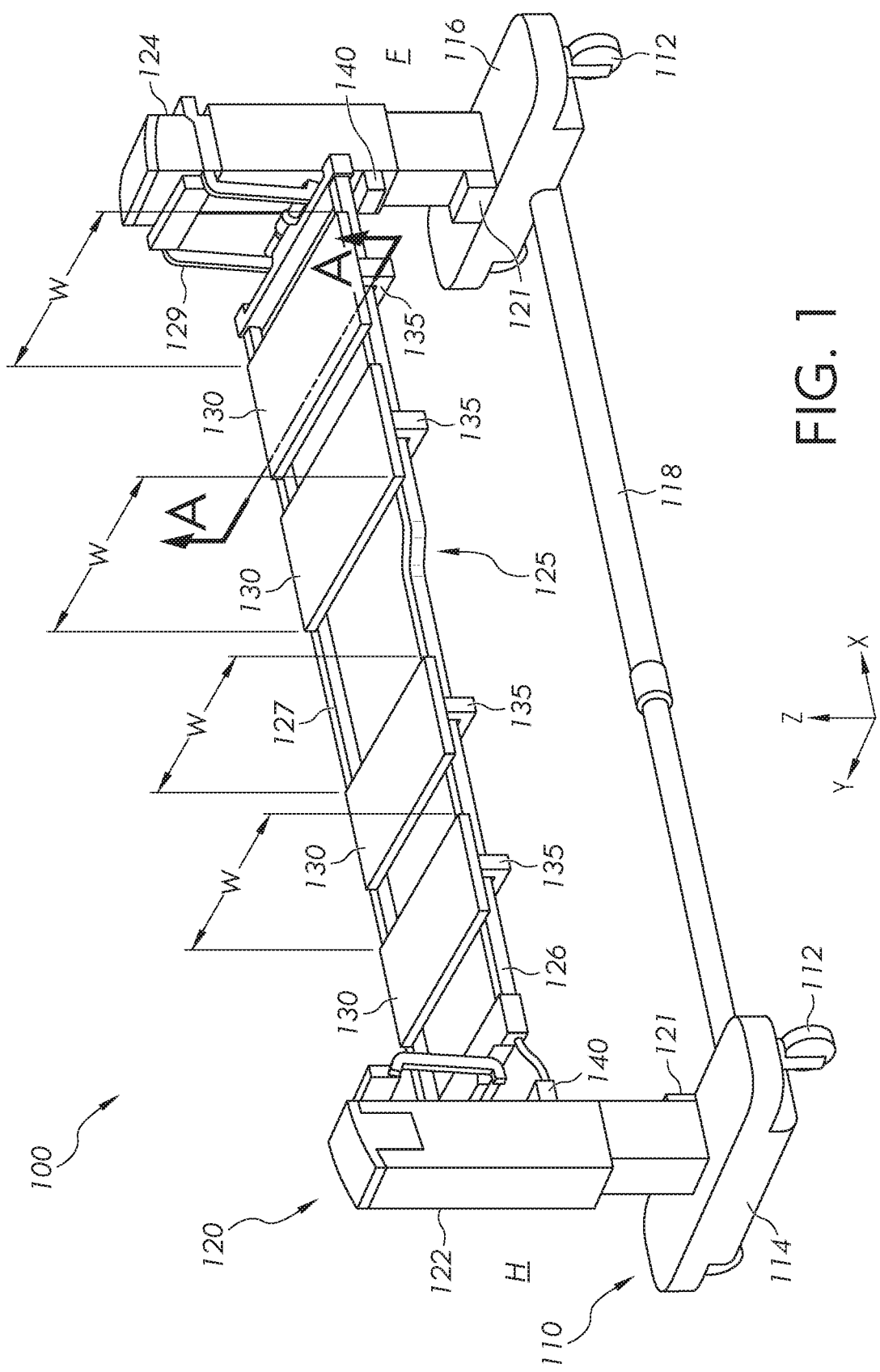
FIG. 1 is a perspective view of a person support system in accordance with one or more embodiments described herein.

FIG. 1 generally depicts one embodiment of a person support system including support pads having cooling features. According to one embodiment, the person support system may include a longitudinal frame comprising at least one side rail. A support pad may be positioned on the longitudinal frame. The support pad may comprise a thermally conductive core portion comprising a support matrix and at least one thermally conductive element. A cooling source may be thermally coupled to the thermally conductive core portion through the side rail with a connector comprising thermally conductive fibers. The cooling source may draw heat from the thermally conductive core portion through the at least one thermally conductive element and the thermally conductive fibers of the connector thereby cooling at least the thermally conductive core portion of the support pad. Various embodiments of the support pads, person support systems with support pads, and methods of using the support pads will be described in more detail herein.

Referring to FIG. 1, one embodiment of a person support system 100 is schematically depicted. In this embodiment, the person support system 100 may be, for example and without limitation, a two-column operating table such as the Allen® Advance Table manufactured by Allen Medical Systems, Inc. of Acton, Mass. The person support system 100 generally includes a base frame 110 and a primary support frame 120 that is supported by the base frame 110. The person support system 100 may further include a plurality of support pads 130 coupled to the primary support frame 120. In various embodiments, one or more of the support pads 130 may include cooling features, as will be described in greater detail herein.

The base frame 110 of the person support system 100 includes a head portion 114 positioned at a head end H of the person support system 100 and a foot portion 116 positioned at a foot end F of the person support system 100. The head portion 114 and the foot portion 116 are spaced apart from one another in a longitudinal direction (i.e., generally along the X axis of the coordinate axes depicted in the FIG. 1) and may be coupled to one another by a central portion 118 that extends between the head portion 114 and the foot portion 116 in the longitudinal direction. The central portion 118 may be extendable and retractable in the longitudinal direction, thereby increasing or decreasing the distance between the head portion 114 and the foot portion 116 in the longitudinal direction. In some embodiments, the head portion 114 and the foot portion 116 each have a plurality of casters 112 coupled thereto, such that the person support system 100 may be moved along a surface, such as a floor.

The primary support frame 120 extends upward in a vertical direction (i.e., generally along the Z axis of the coordinate axes depicted in FIG. 1) from the base frame 110 of the person support system 100. In the embodiment depicted in FIG. 1, the primary support frame 120 includes a head column 122 that extends upward from the head portion 114 of the base frame 110 in the vertical direction. The primary support frame 120 further includes a foot column 124 that extends upward from the foot portion 116 of the base frame 110 in the vertical direction. Accordingly, it should be understood that the head column 122 is generally positioned proximate the head end H of the person support system 100 and the foot column 124 is generally positioned proximate the foot end F of the person support system 100. The head column 122 is spaced apart from the foot column 124 in the longitudinal direction by the central portion 118. In some embodiments, the head column 122 and the foot column 124 are coupled to the head portion 114 and the foot portion 116 of the base frame 110, respectively. Alternatively, the head column 122 and the foot column 124 may be integrated with the head portion 114 and the foot portion 116 of the base frame 110, respectively. The head column 122 and the foot column 124 may be actuated to raise and lower the head column 122 and the foot column 124 in the +/−Z direction of the coordinate axes depicted in FIG. 1.

The primary support frame 120 includes a longitudinal frame 125 that is positioned above the base frame 110 in the vertical direction and that extends between the head column 122 and the foot column 124 in the longitudinal direction. The longitudinal frame 125 is coupled to the head column 122 and the foot column 124 such that the longitudinal frame 125 may be raised, lowered and/or tilted with respect to the base frame 110 upon actuation of the head column 122 and/or the foot column 124. In the embodiment depicted in FIG. 1, the longitudinal frame 125 generally extends in the horizontal plane (i.e., the X-Y as depicted). However, it should be understood that the longitudinal frame 125 may be tilted with respect to the X-Y plane (i.e., about an axis of rotation generally parallel to the Y-axis in the coordinate axes depicted in FIG. 1) or rotated with respect to the X-Y plane (i.e., about an axis of rotation generally parallel to the X-axis in the coordinate axes depicted in FIG. 1). While FIG. 1 generally depicts the longitudinal frame as being substantially planar, in other embodiments, the longitudinal frame 125 may be contoured and may include portions that extend out of the horizontal plane. In some embodiments, the longitudinal frame 125 may include a first side rail 126 and a second side rail 127, where the first side rail 126 and the second side rail 127 extend substantially parallel to each other in the longitudinal direction between the head column 122 and the foot column 124. The first side rail 126 and the second side rail 127 may be coupled to the head column 122 and the foot column 124, respectively, by a head support piece 128 and a foot support piece 129. The head support piece 128 may be coupled between the head column 122 and the first and second side rails 126, 127. In embodiments, the head support piece 128 and the foot support piece 129 may be pivotable with respect to the head column 122 and the foot column 124 about an axis of rotation that is generally parallel to the X-axis in the coordinate axes depicted in FIG. 1. The foot support piece 129 may be coupled between the foot column 124 and the first and second side rails 126, 127.

Figure 2:
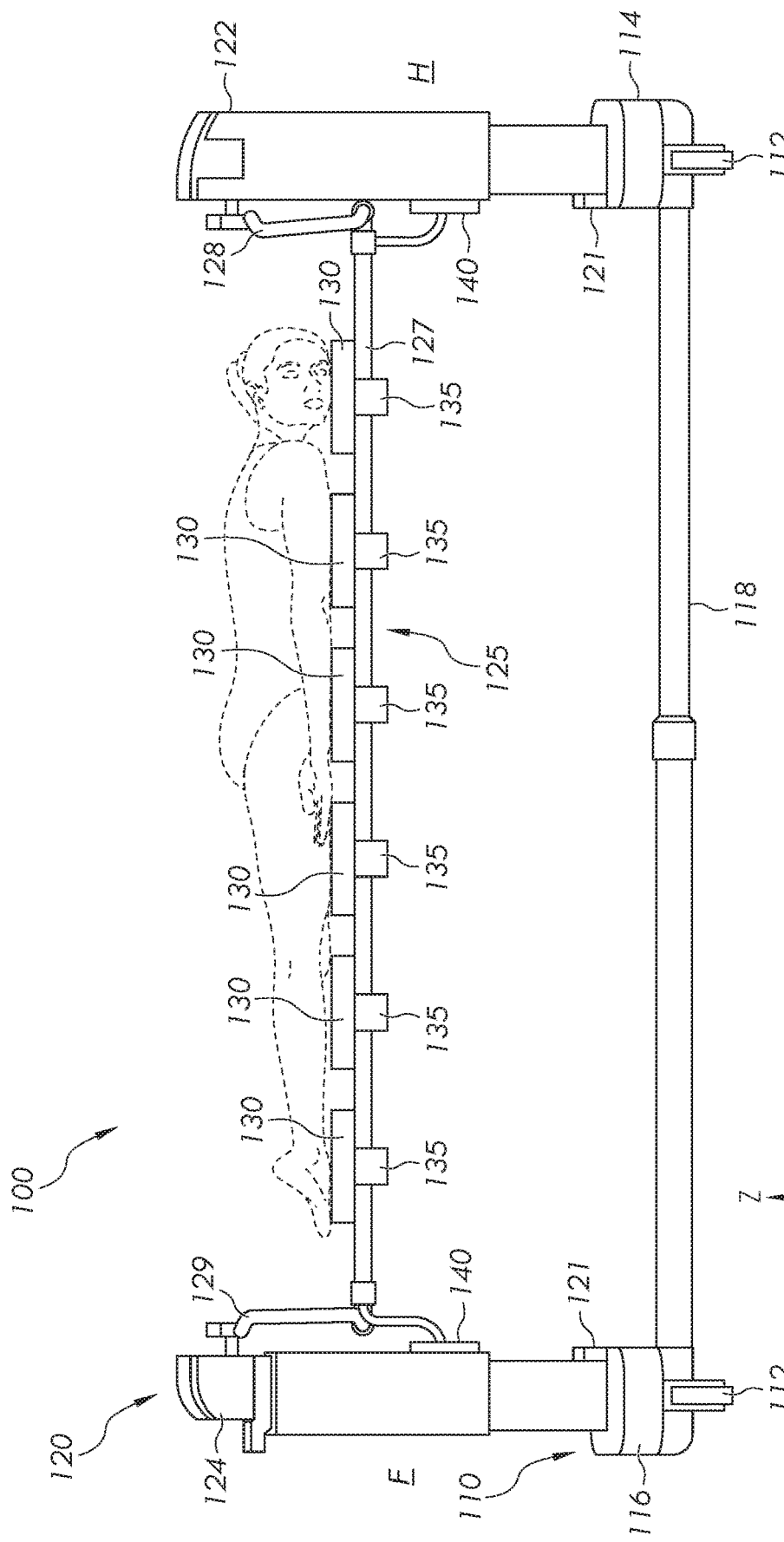
FIG. 2 is a side view of the person support system of FIG. 1.

As depicted in FIGS. 1 and 2, in embodiments, the longitudinal frame 125 supports and may be coupled to each of the plurality of support pads 130, each of which extends a distance in the longitudinal direction between the head column 122 and the foot column 124 and extends a distance in the lateral direction. Alternatively, the longitudinal frame 125 supports and may be coupled to a support deck (not shown), which extends a distance between the head column 122 and the foot column 124 in the longitudinal direction.

Referring again to FIG. 1, as noted above, the head column 122 and the foot column 124 may be adjustable in the vertical direction such that the head column 122 and the foot column 124 may raise or lower the longitudinal frame 125 with respect to the base frame 110 in the vertical direction. In some embodiments, at least one column actuator 121 is coupled to the head column 122 and/or the foot column 124. The at least one column actuator 121 moves the head column 122 and the foot column 124 upward and downward in the vertical direction with respect to the base frame 110. The column actuator 121 may be a powered actuator, such as an electric motor, linear actuator, or the like, or may be manually powered, such as by a system of gears actuated by a pedal, a crank, or the like, or even a hydraulic cylinder actuated by a pedal, crank, or the like. For example, the column actuator 121 may also include a linear actuator, a hydraulic actuator, a pneumatic actuator, an electro-mechanical actuator, or the like.

The head column 122 and the foot column 124 may be raised and lowered in the vertical direction independent of one another such that the longitudinal frame 125 may be tilted with respect to the horizontal plane (i.e., the X-Y plane), as described above. For example, the head column 122 may be raised with respect to the foot column 124 in the vertical direction such that the head end of the longitudinal frame 125 is positioned higher than the foot end of the longitudinal frame 125 in the vertical direction (i.e., a reverse Trendelenburg position). Conversely, the foot column 124 may be raised with respect to the head column 122 in the vertical direction, such that the foot end of the longitudinal frame 125 is positioned higher than the head end of the longitudinal frame 125 in the vertical direction (i.e., a Trendelenburg position). In some embodiments, both the head column 122 and the foot column 124 of the primary support frame 120 may be raised or lowered in the vertical direction simultaneously and in conjunction with one another, thereby raising both the head end and the foot end of the longitudinal frame 125.

Referring again to FIGS. 1 and 2, each of the plurality of support pads 130 are coupled to the longitudinal frame 125 and are positioned between the head column 122 and the foot column 124. In addition, each of the plurality of support pads 130 extends in the lateral direction (i.e., generally along the Y axis of the coordinate axes depicted in FIGS. 1 and 2) by a width W from the first side rail 126 to the second side rail 127. In some embodiments, each of the plurality of support pads 130 may extend beyond the side rails 123, 127, as depicted in FIG. 1. In the embodiment depicted in FIG. 1, the plurality of support pads 130 includes six support pads 130 positioned at various locations between the head column 122 and the foot column 124. However, it should be understood that the number of support pads 130 coupled to the longitudinal frame 125 between the head column 122 and the foot column 124 is not limited by the present disclosure. In some embodiments, the person support system 100 may include a suitable number of support pads 130 sufficient to support a patient thereon.

While FIGS. 1 and 2 generally depict the person support system 100 as comprising a head column 122 and a foot column 124 supporting the longitudinal frame 125, it should be understood that other embodiments are contemplated and possible.

For example, in an alternative embodiment, the longitudinal frame may be supported by a single support column located near the longitudinal center of the longitudinal frame. Examples of such person support systems include, without limitation, the TruSystem® 7000 series or 7500 series of operating room tables manufactured by TRUMPF Medizin Systeme GmbH+Co. KG of Saalfeld, Germany. Alternatively, the person support apparatus may be a MARS™ OR Table or SATURN® OR Table, each of which is manufactured by TRUMPF Medizin Systeme GmbH+Co. KG of Saalfeld, Germany.

Figure 3:
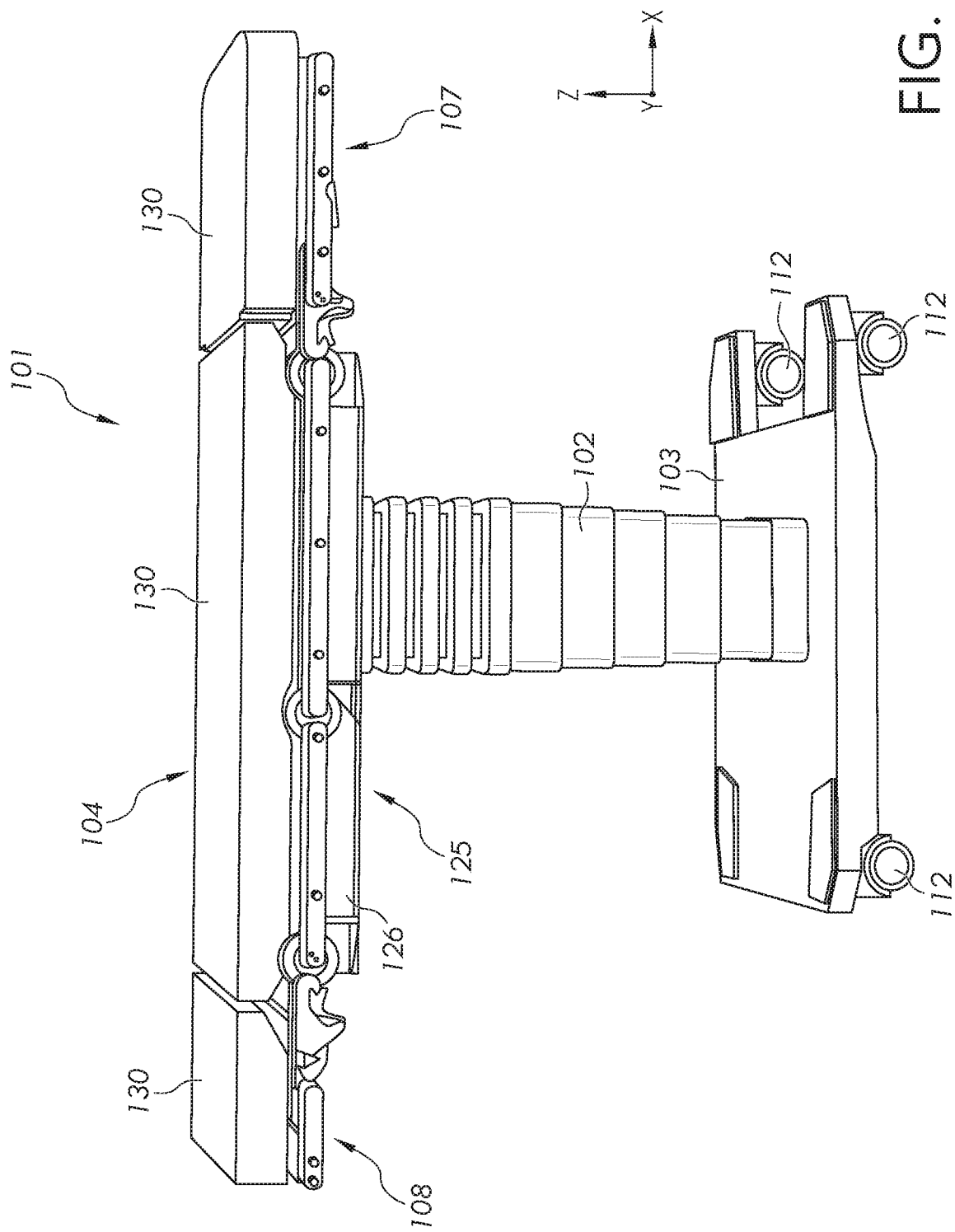
FIG. 3 schematically depicts a perspective view of a person support system in accordance with another embodiment described herein.

Referring to FIG. 3 by way of example, an alternative embodiment of a person support system 101 with a single support column is schematically depicted. In this embodiment, the person support system 101 includes a single support column 102, a base 103, and a table top assembly 104. The base 103 may include a plurality of casters 112 such that the person support system 101 may be moved along a surface, such as a floor. The support column 102 is positioned on and supported by the base 103. The table top assembly 104 is positioned on and supported by the support column 102. In embodiments, the support column 102 may include an adjustment system (not shown) for raising and lowering the table top assembly 104 relative to the base 103 and/or tilting the table top assembly 104 relative to the base 103. For example, in some embodiments the adjustment system may facilitate rotating the table top assembly 104 about an axis generally parallel with the Y axis depicted in FIG. 3 and/or rotating the table top assembly 104 about an axis generally parallel with the X axis depicted in FIG. 3. In embodiments, the adjustment system may be a mechanical adjustment system, an electro-mechanical adjustment system, a hydraulic adjustment system or combinations thereof.

In embodiments, the table top assembly 104 generally includes a longitudinal frame 125, a foot frame 107, and a head frame 108. The foot frame 107 may be pivotally and removably attached to the longitudinal frame 125. Similarly, the head frame 108 may be pivotally and removably attached to the longitudinal frame 125 opposite the foot frame 107. Each of the longitudinal frame 125, foot frame 107, and head frame 108 may include a deck (not shown in FIG. 3) on which a support pad 130 is removably positioned.

Similar to the embodiment of the person support system 100 depicted in FIG. 1, the longitudinal frame 125 of the person support system 101 depicted in FIG. 3 may include a first side rail 126 and a second side rail 127 (not shown in FIG. 3), where the first side rail 126 and the second side rail 127 extend substantially parallel to each other in the longitudinal direction (i.e., the +/−X direction of the coordinate axes depicted in the figures). In embodiments, the first side rail 126 and the second side rail 127 may be coupled to one another with cross rails and/or the deck. While the structure of the longitudinal frame 125 has been described herein, it should be understood that the foot frame 107 and the head frame 108 may have similar structures.

While reference has been made herein to specific embodiments of person support systems 100, 101, it should be understood that the embodiments of support pads with the cooling features of the person support systems described in further detail herein may also be used in conjunction with other person support systems including, without limitation, stretchers, gurneys, and the like.

Referring now to FIG. 1 and FIG. 3, during a medical procedure, such as a surgical procedure or the like, a subject may be positioned on the person support system 100, 101 such that the subject is in contact with the support pad 130. The subject may be in a static position on the support pad for an extended period of time. As such, certain areas of the subject's anatomy in contact with the support pad(s) may be subject to relatively high, localized pressure. For example, when a subject is in a supine position on the support pad(s), portions of the subject's posterior skin, such as the subject's sacral area, buttocks, scapular areas, and heels, may be subject to relatively high, localized pressure due to the subject's own body weight. These areas of relatively high localized pressure, in conjunction with moisture trapped between the subject and the support pad and the local build-up of heat, may lead to the development of pressure ulcers in the tissue of the subject. The embodiments described herein provide person support systems and support pads for person support systems which may assist in mitigating the development of pressure ulcers.

Referring to FIG. 4A by way of example, a cross section through the Y-Z plane of one embodiment of the longitudinal frame 125 and support pad 130 of the person support system 100 (FIG. 1) and/or person support system 101 (FIG. 3) is schematically depicted showing the side rails 126, 127, a deck 160 supported on the side rails 126, 127, and a support pad 130 supported on the deck 160. In embodiments, at least a portion of the support pad 130 includes a thermally conductive core portion 200 which is constructed, at least in part, from thermally conductive material arranged to conduct heat away from an upper or top surface 131 of the support pad 130, thereby providing at least localized, focal cooling of the top surface 131 of the support pad 130 which, in turn, may provide at least localized, focal cooling of a subject positioned on the top surface 131 of the support pad 130. For example, the support pad 130 may include a cover material 136 which, in some embodiments, envelopes and encloses the support pad 130. The cover material 136 may be, for example and without limitation, a woven or non-woven fabric which, in some embodiments, includes a coating, such as a urethane coating, polyurethane coating, or the like, which seals at least the top surface 131 of the support pad 130 from moisture permeation and facilitates cleaning of the support pad 130. In embodiments where the cover material 136 is formed from a woven or non-woven fabric material, the woven or non-woven fabric material may optionally include thermally conductive fibers, such as carbon fibers, metallic fibers or the like, to facilitate the conduction of heat into the thermally conductive core portion 200. In some other embodiments, the cover material 136 may include a solid sheet of material which is impervious to fluids, such as a urethane material, vinyl, or the like. In embodiments where the cover material 136 is formed from a solid sheet material, the solid sheet material may optionally include thermally conductive fibers, such as carbon fibers, metallic fibers or the like, or thermally conductive particles, such as carbon particles, metallic particles or the like, embedded therein to facilitate the conduction of heat into the thermally conductive core portion 200. In embodiments, the thermally conductive core portion 200 is positioned adjacent to the top surface 131 of the support pad 130 (i.e., adjacent to the top surface of the cover material 136) to facilitate good thermal contact with a subject positioned on the top surface 131 of the support pad 130.

While FIG. 4A schematically depicts a support pad 130 in which the thermally conductive core portion 200 extends through the cross section of the support pad 130 within the cover material 136, it should be understood that other configurations of the thermally conductive core portion 200 are contemplated and possible. Referring to FIG. 4B by way of example, an alternative embodiment of a cross section through the Y-Z plane of the longitudinal frame 125 and support pad 130 is schematically depicted. As noted herein with respect to FIG. 4A, the support pad 130 includes a thermally conductive core portion 200 enclosed within a cover material 136. In the embodiment depicted in FIG. 4A, the thermally conductive core portion 200 is disposed in only a portion of the support pad 130. Specifically, the support pad 130 includes a core part 132 disposed within the cover material 136. The core part 132 may be formed from, for example and without limitation, a foam such as urethane foam, polyurethane foam or the like. The core part 132 may also include a combination of different foam materials. For example, the core part 132 may include a urethane foam or a polyurethane foam with an additional layer of memory foam disposed over the urethane foam or the polyurethane foam. In these embodiments, the thermally conductive core portion 200 is disposed in a portion of the core part 132. For example, the thermally conductive core portion 200 may be disposed in a recess 137 formed in the core part 132 and located adjacent to the top surface 131 of the support pad (i.e., adjacent to the cover material 136 forming the top surface 131 of the support pad 130).

In embodiments, the thermally conductive core portion 200 need not extend through the entire thickness (i.e., the +/−Z direction of the coordinate axes depicted in FIG. 4B) of the core part 132. That is, the thermally conductive core portion 200 may be positioned in the core part 132 and has a thickness that is less than the thickness of the core part 132. In some embodiments, the thermally conductive core portion 200 may not extend across the entire width (i.e., the +/−Y direction of the coordinate axes depicted in FIG. 4B) of the core part 132. That is, the thermally conductive core portion 200 is positioned in the core part 132 and has a width that is less than the width of the core part 132. In some embodiments, the thermally conductive core portion 200 may not extend across the entire length (i.e., the +/−X direction of the coordinate axes depicted in FIG. 4B) of the core part 132. That is, the thermally conductive core portion 200 is positioned in the core part 132 and has a length that is less than the length of the core part 132. In some embodiments, the thermally conductive core portion 200 has at least a width and a length that are less than the corresponding dimensions of the core part 132.

Constructing the support pad 130 such that the thermally conductive core portion 200 has at least a width and a length that are less than the corresponding dimensions of the core part 132 allows for discrete, targeted cooling (i.e., focal cooling) of particular areas of a subject positioned on the support pad. For example, in some embodiments, the thermally conductive core portion 200 may be located within recesses 137 in the core part 132 beneath areas of the top surface 131 that contact a subject at locations most prone to the development of pressure ulcers, including, without limitation, the sacral area, buttocks, scapular areas, heels, and the like. Discrete, focal cooling of these areas with the thermally conductive core portion 200 may aid in mitigating the development of pressure ulcers.

Figure 4C:
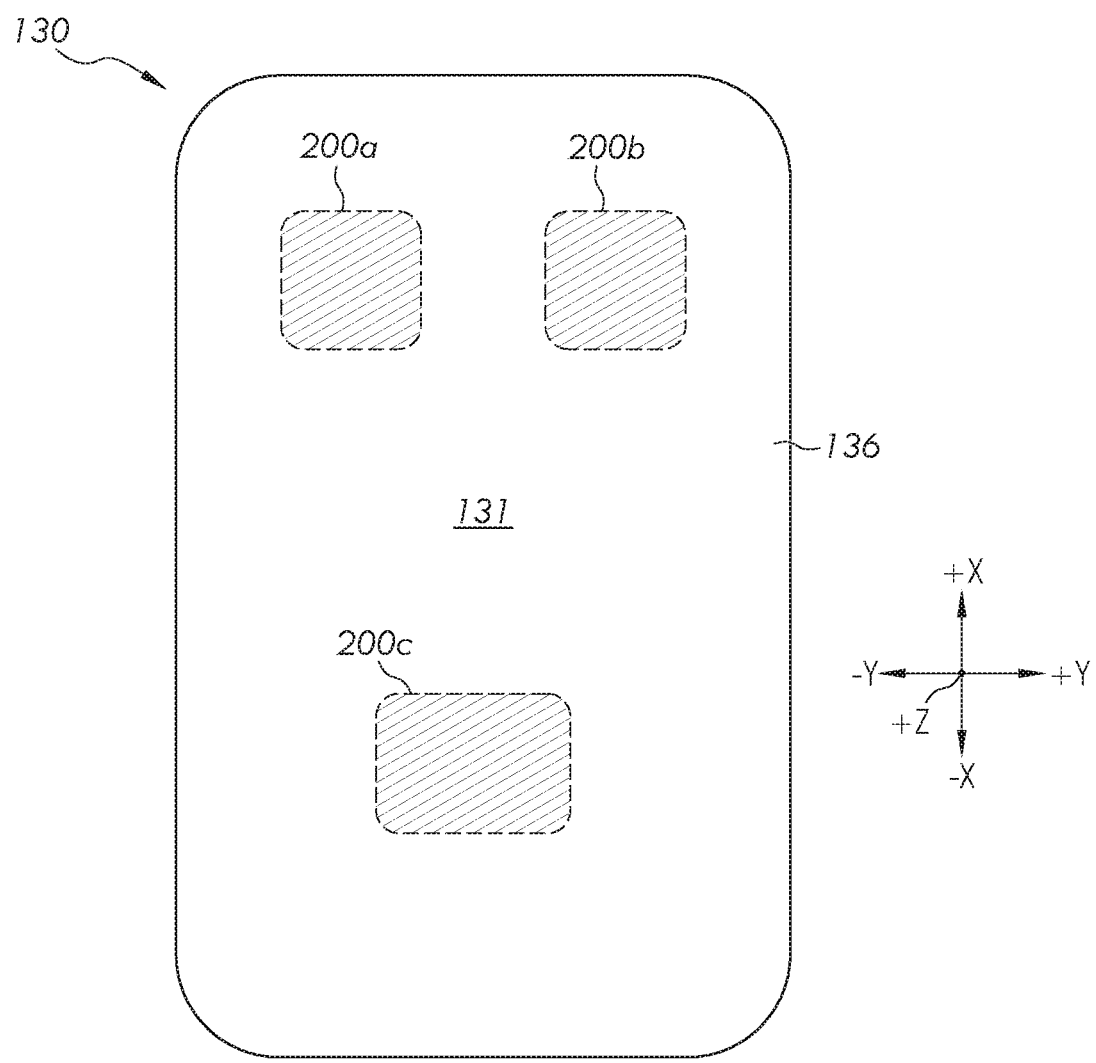
FIG. 4C schematically depicts a top view of a support pad depicting the location of thermally conductive core portions in accordance with one or more embodiments described herein.

For example, FIG. 4C is a top view of the support pad 130 depicted in FIG. 4B showing the relative positioning of three thermally conductive core portions 200a, 200b, 200c in the core part beneath the cover material 136. As depicted in FIG. 4C, thermally conductive core portions 200a, 200b are generally located beneath the areas of the top surface 131 that correspond to the scapular areas of a subject positioned on the top surface 131 of the support pad 130 while thermally conductive core portion 200c is generally located beneath the area of the top surface 131 that corresponds to the sacral area of a subject positioned on the top surface 131 (assuming the head of the subject is positioned towards the end of the support pad 130 in the +X direction of the coordinate axes depicted and the pelvis of the subject is positioned towards the end of the support pad in the −X direction of the coordinate axes depicted). While FIG. 4C schematically depicts a support pad 130 that includes three thermally conductive core portions 200a, 200b, 200c, it should be understood that the number of thermally conductive core portions within the support pad 130 may be greater than three or less than three. For example and without limitation, in embodiments, the support pad 130 may include the thermally conductive core portions 200a, 200b corresponding to the scapular areas or the thermally conductive core portion 200c corresponding to the sacral area.

Referring again to FIG. 4B, in embodiments, the core part 132 of the support pad 130 may be formed with a channel 133 extending through the foam of the core part 132 from the recess 137 where the thermally conductive core portion 200 is located to the edge of the support pad 130, as depicted in FIG. 4B. The channel 133 may facilitate removing and replacing the thermally conductive core portion 200 with, for example, a thermally conductive core portion constructed from different thermally conductive material having different cooling characteristics or a "fresh" thermally conductive core portion (such as when the thermally conductive core portion 200 has reached an equilibrium temperature with a subject positioned on the support pad 130 and the cooling capabilities of the thermally conductive core portion 200 are exhausted). In other embodiments, the channel 133 may facilitate removing and replacing the thermally conductive core portion 200 in the recess 137 with, for example, a plug of foam material similar or identical to the foam of the core part 132. The thermally conductive core portion 200 may be replaced with a plug of foam material when, for example, focal cooling of a particular area is not needed or desired. The plug of foam material fills the recess 137 previously occupied by the thermally conductive core portion 200, thereby maintaining the support provided by the support pad 130 in the absence of the thermally conductive core portion 200. In embodiments, access to the channel 133 in the core part 132 may be provided by, for example, a closure 138 formed in the cover material 136 enveloping the core part 132. The closure 138 may be, for example and without limitation, a flap, a hook-and-loop closure, a zipper, or the like.

Still referring to FIGS. 4A and 4B, in embodiments, the side rails 126, 127 may be formed from materials suitable for use in load bearing applications. Suitable materials may include, for example and without limitation, aluminum alloys, steel, titanium alloys, carbon fiber composites or the like. In embodiments where radiolucency is desired, the side rails 126, 127 may be formed from, for example, carbon fiber composites. The deck 160 may also be formed from materials suitable for use in load bearing applications such as aluminum alloys, steel, titanium alloys, carbon fiber composites or the like. As with the side rails 126, 127, the deck 160 may be formed from carbon fiber composites when radiolucency is desired. More specifically, in various embodiments provided herein, the materials of various components of the person support systems 100, 101 are radiolucent, or transparent to x-rays. Radiolucency, particularly in the area of the support pads 130 enables x-ray and fluoroscopic imaging to be performed during surgical procedures without interference from the person support system. X-ray or fluoroscopic images may be taken with a device having a C-arm that includes portions above and below the subject on the person support system. The use of non-radiolucent materials can cause shadows or even obstructions in the x-ray or fluoroscopic images. Accordingly, in some embodiments, portions of the person support systems described herein, such as the support pads 130 or the like, are formed from radiolucent materials.

In embodiments described herein, the thermally conductive core portion 200 of the support pad 130 may be utilized to provide focal cooling to a targeted area of a subject positioned on the support pad 130 including, without limitation, the scapular areas, the sacral areas, the buttocks, the heels, and the like. In embodiments, the targeted area may be cooled to a temperature that is from about 3° C. to about 20° C. less than body temperature. The focal cooling may be done either passively or actively, such as when the thermally conductive core portion is further coupled to a cooling source (i.e., a heat sink) as will be described in further detail herein. For example, in some embodiments, the thermally conductive core portion 200 of the support pad 130 may be thermally coupled to a cooling source (not shown) disposed within an interior channel 180 formed in at least one of the side rails 126, 127. The cooling source may be at a lower temperature than at least a portion of the thermally conductive core portion 200 such that the temperature gradient between the thermally conductive core portion 200 and the cooling source promotes the conduction of heat from the thermally conductive core portion 200 to the cooling source. That is, thermally coupling the thermally conductive core portion 200 of the support pad 130 to a cooling source (not shown) may assist in actively conducting heat away from the top surface 131 of the support pad 130, enhancing the cooling provide by the thermally conductive core portion 200. In embodiments, the thermally conductive core portion 200 may be thermally coupled to the cooling source with one or more thermally conductive elements formed from thermally conductive materials, as will be described in further detail herein.

Various embodiments of thermally conductive core portions 200 suitable for use with the support pads of FIGS. 4A and 4B will be described in further detail with specific reference to FIGS. 5A-5G.

Figure 5A:
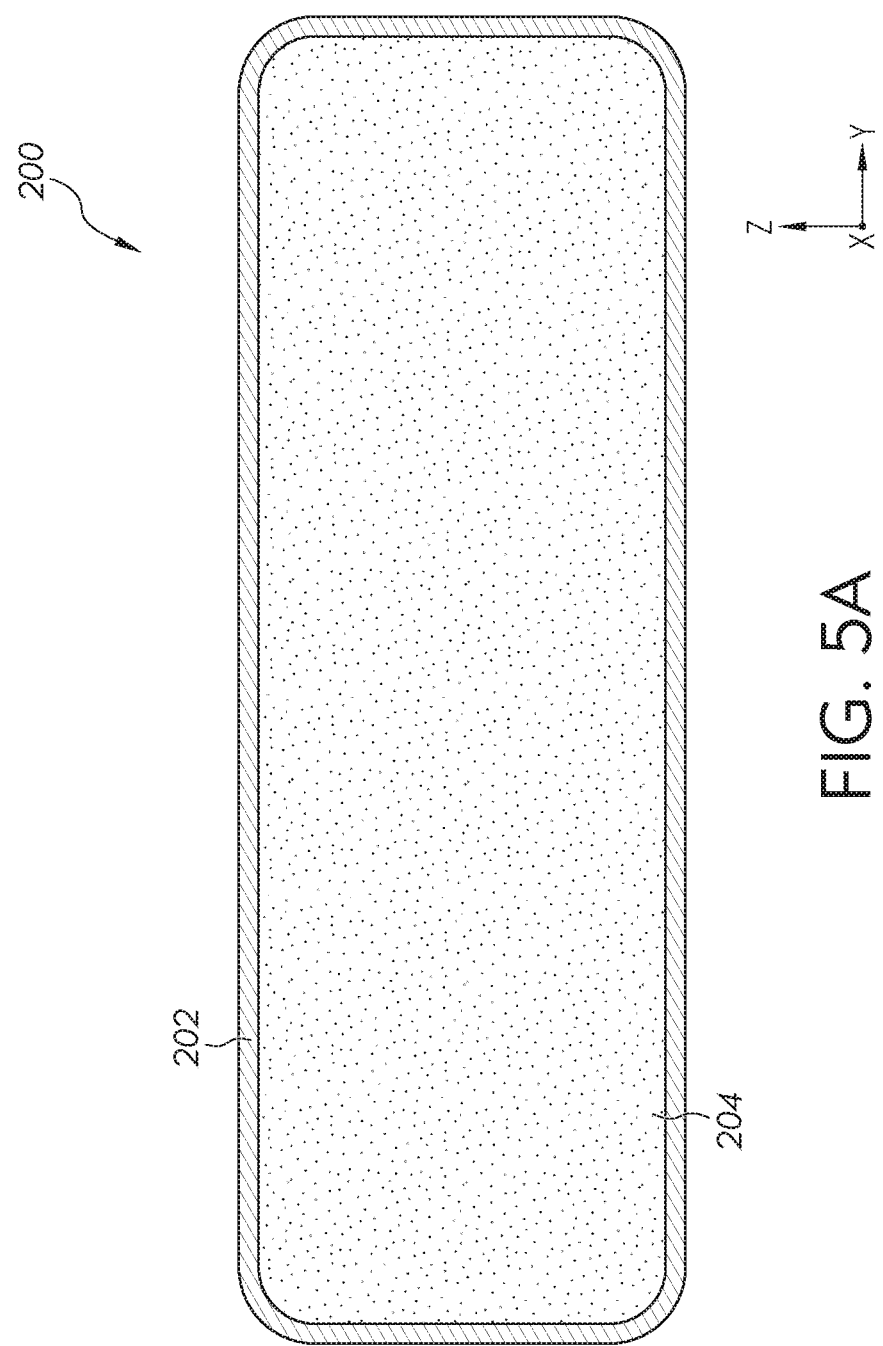
FIG. 5A schematically depicts a cross-section of a thermally conductive core portion in accordance with one or more embodiments described herein.

The thermally conductive core portions 200 of the support pads 130 may be formed from a variety of different materials in different arrangements. One embodiment of a thermally conductive core portion 200 is schematically depicted in FIG. 5A. The thermally conductive core portion 200 of this embodiment includes a support matrix 204 enclosed within a compliant shell 202. The compliant shell 202 may be formed from, for example, a fluid impermeable, elastomeric film. Suitable elastomeric films include, without limitation, urethane films, polyurethane films, and the like. The film generally has a thickness of less than 5 mils (127 micrometers) to facilitate conduction of heat into the support matrix 204. In some embodiments, the compliant shell 202 has a thickness of less than 4 mils (101.6 micrometers) or even less than or equal to 3 mils (76.2 micrometers). In embodiments, the compliant shell 202 has a thickness greater than or equal to 1 mil (25.4 micrometers) and less than or equal to 3 mils (76.2 micrometers). In some embodiments, the compliant shell 202 has a thickness greater than or equal to 2 mils (50.8 micrometers) and less than or equal to 3 mils (76.2 micrometers).

In the embodiment depicted in FIG. 5A, the support matrix 204 may be formed from thermally absorptive materials including, without limitation, oils with high heat capacity, fluids with high heat capacity, phase change materials (PCMs) and the like. Suitable phase change materials include, without limitation, alkanes having a melting temperature greater than or equal to about 5° C. and less than or equal to about 35° C. Examples of suitable alkanes include, without limitation, tetradecane, pentadecane, hexadecane, heptadecane, octadecane, and nonadecane. However, it should be understood that other suitable phase change materials may be used for the support matrix 204. Suitable oils may include, without limitation, inorganic oils, silicone oils, mineral oils, and the like. Suitable fluids may include, without limitation, water, cooling fluids, or mixtures of water and cooling fluids. In embodiments where the support matrix 204 includes a fluid, an antimicrobial may be added to the fluid to mitigate microbial growth. In embodiments, the thermally conductive core portion 200 may be constructed from different phase change materials (or even different combinations of phase change materials) to achieve different degrees of cooling. In some embodiments, more or less phase change material may be incorporated into the support matrix 204 to achieve different degrees of cooling and/or the thickness of the thermally conductive core portion 200 may be increased or decreased to achieve different degrees of cooling.

Referring to FIGS. 4B and 5A, when the thermally conductive core portion 200 is positioned in the support pad 130 and a subject (not shown) is positioned on the top surface 131 of the support pad 130 over the thermally conductive core portion 200, heat from the subject is absorbed into the thermally conductive core portion 200. In embodiments where the support matrix comprises phase change materials, the absorbed heat causes the support matrix 204 to undergo a phase transformation from a solid into a pseudo-solid (i.e., a gel) or a liquid. The absorption of heat into the thermally conductive core portion 200 results in the localized cooling of the portion of the subject positioned over the thermally conductive core portion 200.

Figure 5B:
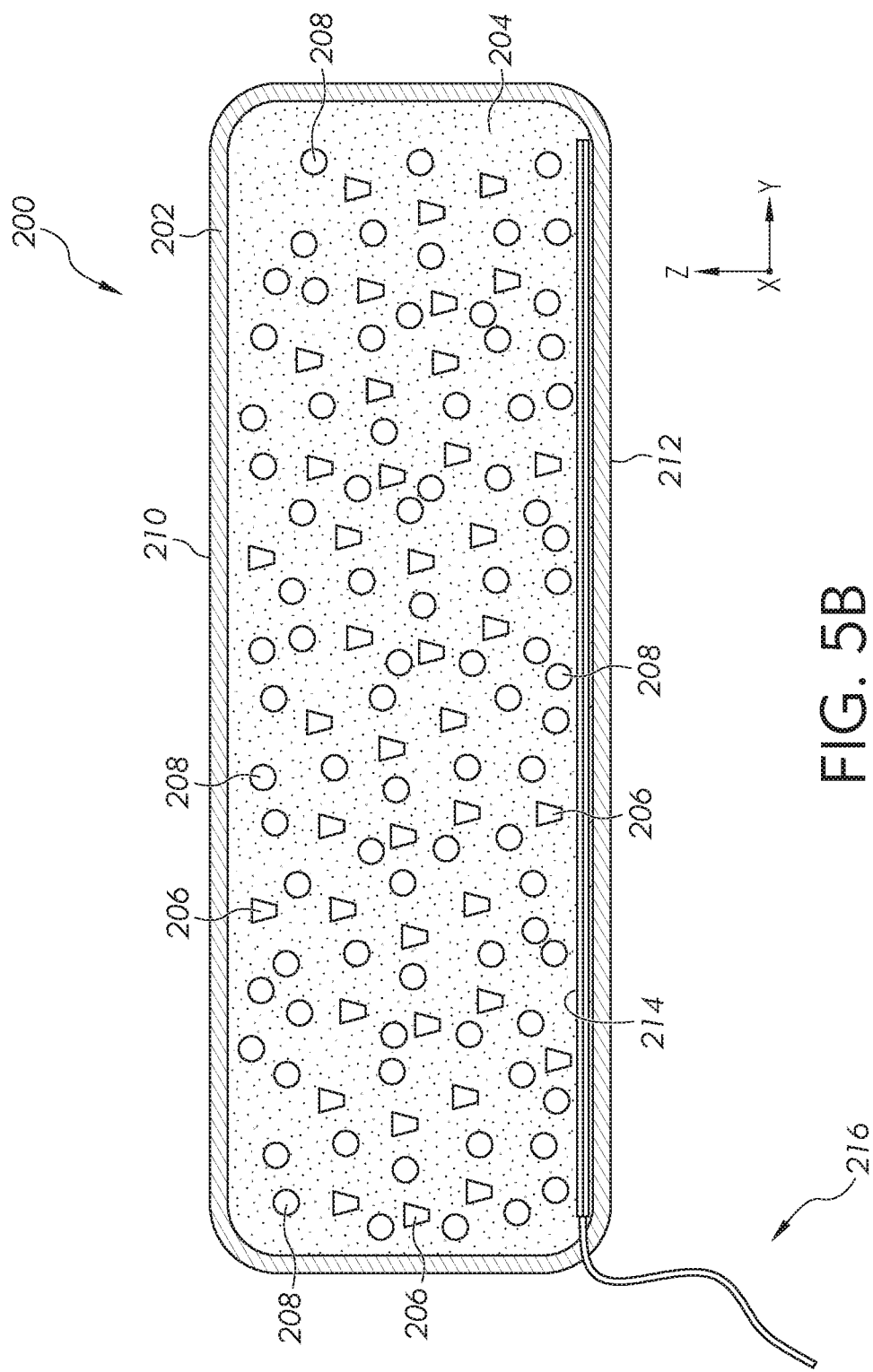
FIG. 5B schematically depicts a cross-section of a thermally conductive core portion in accordance with one or more embodiments described herein.

Referring now to FIG. 5B, in other embodiments, the thermally conductive core portion 200 may include a support matrix 204 enclosed within a compliant shell 202. The compliant shell 202 may be formed from the same materials and have the same dimensions as described herein with respect to FIG. 5A. In the embodiment depicted in FIG. 5B, the support matrix 204 may be formed from, for example, elastomeric gels, foams, oils, or fluids. Suitable elastomeric gels may include, without limitation, silicone gels, urethane gels, polyurethane gels and the like. Suitable oils may include, without limitation, inorganic oils, silicone oils, mineral oils, and the like. Suitable foams may include, without limitation, urethane foam, polyurethane foam, and the like. Suitable fluids may include, without limitation, water, cooling fluids, or mixtures of water and cooling fluids. In embodiments where the support matrix 204 includes a fluid, the support matrix 204 may further include an anti-microbial agent to resist microbial growth.

In the embodiment depicted in FIG. 5B, the support matrix 204 may further include thermally conductive elements and/or thermally absorptive elements. For example, the support matrix 204 may include thermally conductive elements, such as thermally conductive particles 206, suspended within the support matrix 204 to facilitate the conduction of heat through the support matrix 204 from the top surface 210 of the thermally conductive core portion 200 to the bottom surface 212 of the thermally conductive core portion 200. The thermally conductive particles 206 may have a relatively high thermal conductivity (e.g., greater than about 40 W/m*K). Examples of thermally conductive particles 206 include, without limitation, metallic particles, carbon nanotubes, polymer particles, and combinations thereof. Suitable metallic particles include, without limitation, copper particles, copper alloy particles, silver particles, silver alloy particles, gold particles, gold alloy particles, and the like. Suitable polymer particles include, without limitation, ultra-high molecular weight polyethylene particles, polypropylene particles, liquid crystalline polymer particles, polyphthalamide particles, polycarbonate particles, and the like.

In some embodiments, the thermally conductive particles 206 are evenly dispersed throughout the support matrix 204. In some other embodiments, the thermally conductive particles 206 are dispersed in the support matrix 204 such that the density of the thermally conductive particles 206 in the support matrix 204 (i.e., the number of thermally conductive particles 206 per unit volume of the support matrix 204) is greatest proximate the top surface 210 of the thermally conductive core portion 200 and decreases with increasing distance from the top surface 210 of the thermally conductive core portion 200. While not wishing to be bound by theory, it is believed that having a greater density of thermally conductive particles 206 proximate the top surface 210 of the thermally conductive core portion 200 may enhance the conduction of heat away from the top surface 210 of the thermally conductive core portion 200 and into the support matrix 204.

Still referring to FIG. 5B, in some embodiments, the thermally conductive core portion 200 may further include a plurality of thermally absorptive elements 208 suspended within the support matrix 204. The thermally absorptive elements 208 may be in addition to, or as an alternative to, the thermally conductive particles 206. The thermally absorptive elements 208 facilitate the absorption and dissipation of heat from the top surface 210 of the thermally conductive core portion 200 into the support matrix 204. In embodiments, the thermally absorptive elements 208 may be formed from phase change materials (PCMs). Suitable phase change materials include, without limitation, alkanes having a melting temperature greater than or equal to about 5° C. and less than or equal to about 35° C. Suitable alkanes may include, without limitation, tetradecane, pentadecane, hexadecane, heptadecane, octadecane, and nonadecane. However, it should be understood that the thermally absorptive elements 208 may be formed from other suitable phase change materials.

In some embodiments, the thermally absorptive elements 208 are evenly dispersed throughout the support matrix 204. In some other embodiments, the thermally absorptive elements 208 are dispersed in the support matrix 204 such that the density of the thermally absorptive elements 208 in the support matrix 204 (i.e., the number of thermally absorptive elements 208 per unit volume of the support matrix 204) is greatest proximate the top surface 210 of the thermally conductive core portion 200 and decreases with increasing distance from the top surface 210 of the thermally conductive core portion 200. While not wishing to be bound by theory, it is believed that having a greater density of thermally absorptive elements 208 proximate the top surface 210 of the thermally conductive core portion 200 may enhance the extraction and dissipation of heat from the top surface 210 of the thermally conductive core portion 200 and into the support matrix 204.

In still other embodiments, the amount of thermally absorptive elements 208 in the support matrix 204 may be varied when constructing the thermally conductive core portion 200 to adjust the amount of cooling that can be achieved with the thermally conductive core portion 200.

While FIG. 5B schematically depicts the thermally conductive core portion 200 as including both thermally conductive particles 206 and thermally absorptive elements 208 dispersed in the support matrix 204, it should be understood that the thermally conductive core portion 200 may be formed without the thermally conductive particles 206 or without the thermally absorptive elements 208. For example, in embodiments, the thermally conductive core portion 200 may be formed with only the thermally conductive particles 206 dispersed in the support matrix 204. Alternatively, in embodiments, the thermally conductive core portion 200 may be formed with only the thermally absorptive elements 208 dispersed in the support matrix 204.

In the embodiment depicted in FIG. 5B, the thermally conductive core portion 200 may further include a thermal transport layer 214 thermally coupled to the support matrix and configured to conduct heat from the support matrix. In some embodiments, the thermal transport layer 214 is disposed between the support matrix 204 and the compliant shell 202, as depicted in FIG. 5B. In some other embodiments (not shown), the thermal transport layer 214 is embedded within the support matrix 204 such that a portion of the support matrix 204 is disposed between the thermal transport layer 214 and the bottom surface 212 of the compliant shell 202 and another portion of the support matrix 204 is disposed between the thermal transport layer 214 and the top surface 210 of the compliant shell 202.

The thermal transport layer 214 may be constructed from thermally conductive materials such as, without limitation, metals, polymers, carbon fiber and/or combinations thereof. For example, in embodiments, the thermal transport layer 214 may be formed from a metal or alloy having relatively high thermal conductivity (e.g., greater than about 40 W/m*K) such as, for example and without limitation, copper, alloys of copper, and the like. In these embodiments, the thermal transport layer 214 may be in the form of a metal plate or, alternatively, a layer of woven or non-woven metallic fibers. Alternatively, the thermal transport layer 214 may be formed from a polymer material having a relatively high thermal conductivity (e.g., greater than about 40 W/m*K) such as ultra-high molecular weight polyethylene, polypropylene, liquid crystalline polymer, polyphthalamide, polycarbonate, or the like. In these embodiments, the thermal transport layer 214 may be in the form of a polymer plate or, alternatively, a layer of woven or non-woven polymer fibers. As yet another alternative, the thermal transport layer 214 may be formed from a layer of woven or non-woven carbon fiber having a relatively high thermal conductivity (e.g., greater than about 40 W/m*K). Suitable carbon fibers include, without limitation, pitch-based carbon fibers. In these embodiments, the thermal transport layer 214 may be in the form of a carbon fiber plate or, alternatively, a layer of woven or non-woven carbon fibers.

In embodiments where radiolucency of the thermally conductive core portion 200 is desired, the thermally conductive particles 206 may be carbon nanotubes or thermally conductive polymers and the thermal transport layer 214 may be formed from carbon fiber or thermally conductive polymer(s).

In embodiments, the thermally conductive core portion 200 may further include a pigtail connector 216 thermally coupled to the thermal transport layer 214 and extending through the compliant shell 202. The pigtail connector 216 may be used to couple the thermally conductive core portion 200 to a cooling source (described in further detail herein), thereby facilitating the extraction of heat from the interior of the thermally conductive core portion 200. In embodiments, the pigtail connector 216 may be formed from, for example and without limitation, thermally conductive elements having a thermal conductivity of greater than about 40 W/m*K. For example, the thermally conductive elements of the pigtail connector 216 may have a thermal conductivity of from about 40 W/m*K to about 2000 W/m*K, from about 60 W/m*K to about 1000 W/m*K, from about 80 W/m*K to about 500 W/m*K, or from about 100 W/m*K to about 300 W/m*K. In one particular example, the thermally conductive elements may be carbon fibers, such as pitch-based carbon fibers. Alternatively, the thermally conductive elements may be polymer fibers or strips, such as polymer fibers or strips formed from ultra-high molecular weight polyethylene, polypropylene, liquid crystalline polymer, polyphthalamide, polycarbonate, or the like. In yet another alternative, the thermally conductive elements may be metallic fibers or wires, such as fibers or wires formed from copper or alloys of copper.

Referring to FIGS. 4B and 5B, when the thermally conductive core portion 200 is positioned in the support pad 130 and a subject (not shown) is positioned on the top surface 131 of the support pad 130 over the thermally conductive core portion 200, heat from the subject is conducted into the support matrix 204 and through the support matrix 204 with the thermally conductive particles 206 to the thermal transport layer 214. The thermal transport layer 214 conducts the heat laterally (i.e., in the X-Y plane) relative to the bottom surface 212 of the thermally conductive core portion 200. Optionally, the heat may be conducted from the thermal transport layer 214 and through the pigtail connector 216 to a cooling source where the heat is dissipated. The conduction of heat into and through the thermally conductive core portion 200 results in the localized cooling of the portion of the subject positioned over the thermally conductive core portion 200.

As noted herein, the thermally conductive particles 206 may be dispersed throughout the support matrix 204. In embodiments, the thermal conductivity of the support matrix 204 may increase when the support matrix 204 is compressed, such as by the weight of a subject positioned on the support pad 130. That is, as the support matrix 204 is compressed, the thermally conductive particles 206 are brought into closer proximity, thereby improving the thermal conductivity of the support matrix 204.

In embodiments where the support matrix 204 comprises thermally absorptive elements 208, the thermally absorptive elements 208 further assist in cooling an area of the subject positioned over the thermally conductive core portion 200. Specifically, heat from the subject may be directly absorbed and dissipated by the thermally absorptive elements 208. Similarly, heat being conducted through the support matrix 204 may be absorbed and dissipated by the thermally absorptive elements 208. In either case, the absorption of heat causes the thermally absorptive elements 208 to undergo a phase transformation from a solid or pseudo-solid (i.e., a gel) to a liquid resulting in the dissipation of heat and the localized cooling of the portion of the subject positioned over the thermally conductive core portion 200.

Figure 5C:
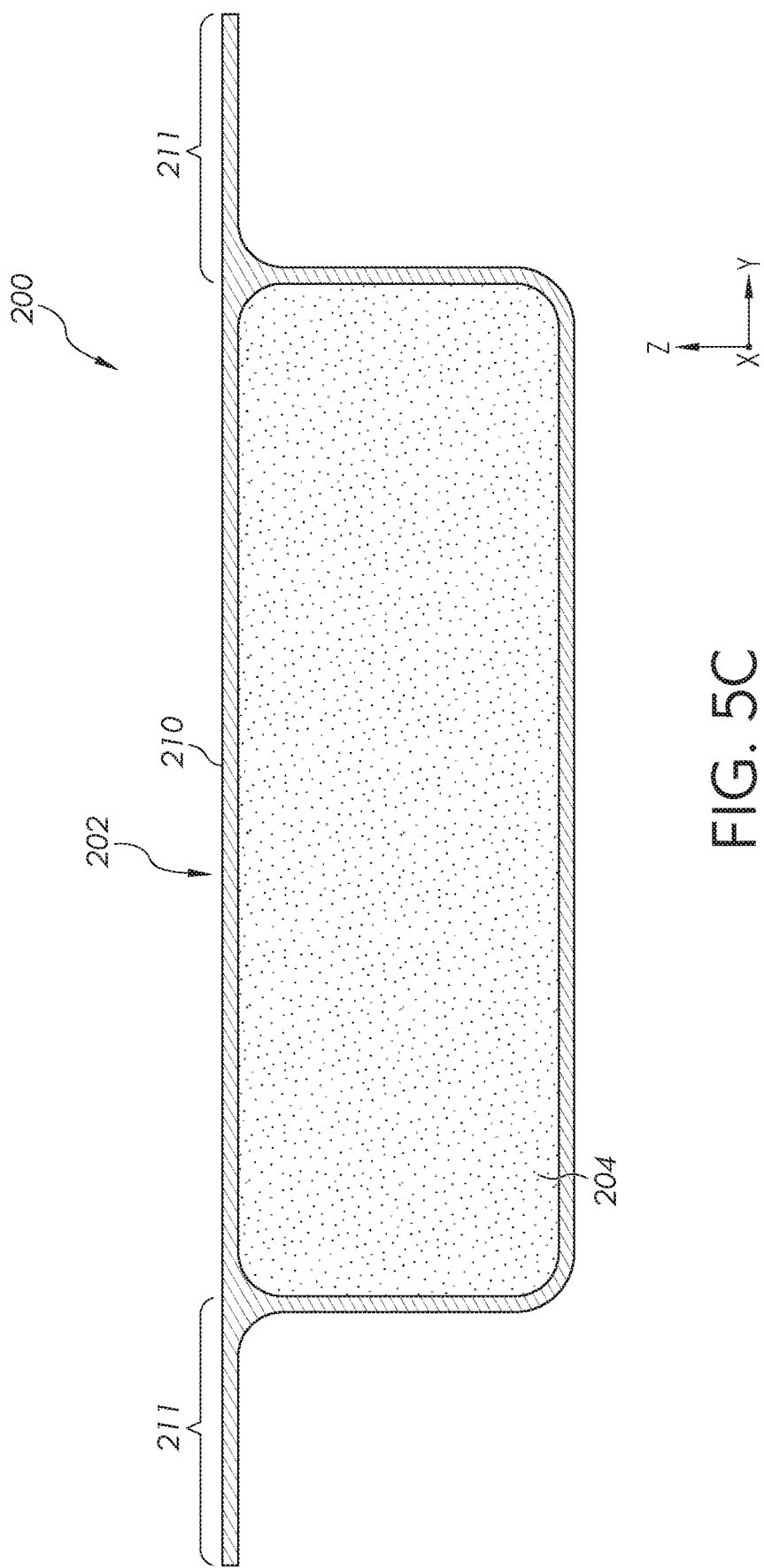
FIG. 5C schematically depicts a cross-section of a thermally conductive core portion in accordance with one or more embodiments described herein.

Referring now to FIG. 5C, an alternative embodiment of a thermally conductive core portion 200 is schematically depicted. In this embodiment, the thermally conductive core portion 200 includes a support matrix 204 enclosed within a compliant shell 202, as described herein with respect to FIGS. 5A and 5B. In this embodiment, the support matrix 204 of the thermally conductive core portion 200 may be formed from one or more thermally absorptive materials, as described herein with respect to FIG. 5A. However, it should be understood that the support matrix 204 of the thermally conductive core portion 200 may be constructed as described with respect to FIG. 5B, that is, with a support matrix 204 formed from elastomeric gels, foams, oils, or fluids and which comprises thermally conductive particles 206 and/or thermally absorptive elements 208.

In the embodiment depicted in FIG. 5C a top surface 210 of the compliant shell 202 may be formed with a cover flange 211 that extends around the support matrix 204 and is continuous with the top surface 210 of the compliant shell 202. In this embodiment, at least the top surface 210 and the cover flange 211 of the compliant shell 202 may be formed from a thermally conductive material or, alternatively, from a material in which thermally conductive elements are incorporated. For example, in embodiments, at least the top surface 210 of the compliant shell 202 includes thermally conductive elements having a relatively high thermal conductivity (e.g., greater than about 40 W/m*K). The thermally conductive elements may include for example and without limitation, metal particles or metal fibers formed from copper, alloys of copper, silver, alloys of silver, gold, alloys of gold, and the like. For example, in embodiments, at least the top surface 210 of the compliant shell 202 may be in the form of an elastomeric film which includes metal particulates or a layer of woven or non-woven metallic fibers. Alternatively, at least the top surface 210 of the compliant shell 202 may be formed from or incorporate a polymer material having a relatively high thermal conductivity (e.g., greater than about 40 W/m*K) such as particles or fibers formed from ultra-high molecular weight polyethylene, polypropylene, liquid crystalline polymer, polyphthalamide, polycarbonate, or the like. For example, in embodiments, at least the top surface 210 of the compliant shell 202 may be in the form of an elastomeric film which includes thermally conductive polymer particles or a layer of woven or non-woven thermally conductive polymer fibers. As yet another alternative, at least the top surface 210 of the compliant shell 202 may be formed from or incorporate carbon fiber or carbon nanotubes having a relatively high thermal conductivity (e.g., greater than about 40 W/m*K). For example, in embodiments, at least the top surface 210 of the compliant shell 202 may be in the form of an elastomeric film which includes thermally conductive carbon particulates or a layer of woven or non-woven thermally conductive carbon fibers.

In the embodiment of the thermally conductive core portion 200 depicted in FIG. 5C, the cover flange 211 of the compliant shell 202 assists in conducting heat into the support matrix 204. For example, when the thermally conductive core portion 200 is positioned in the support pad and a subject (not shown) is positioned on the top surface of the support pad over and in contact with the cover flange 211, heat from the subject is conducted through the cover flange 211 and into the support matrix 204 where the heat is dissipated. The conduction of heat into the thermally conductive core portion 200 through the cover flange 211 results in the localized cooling of the portion of the subject positioned over the thermally conductive core portion 200.

Figure 5D:
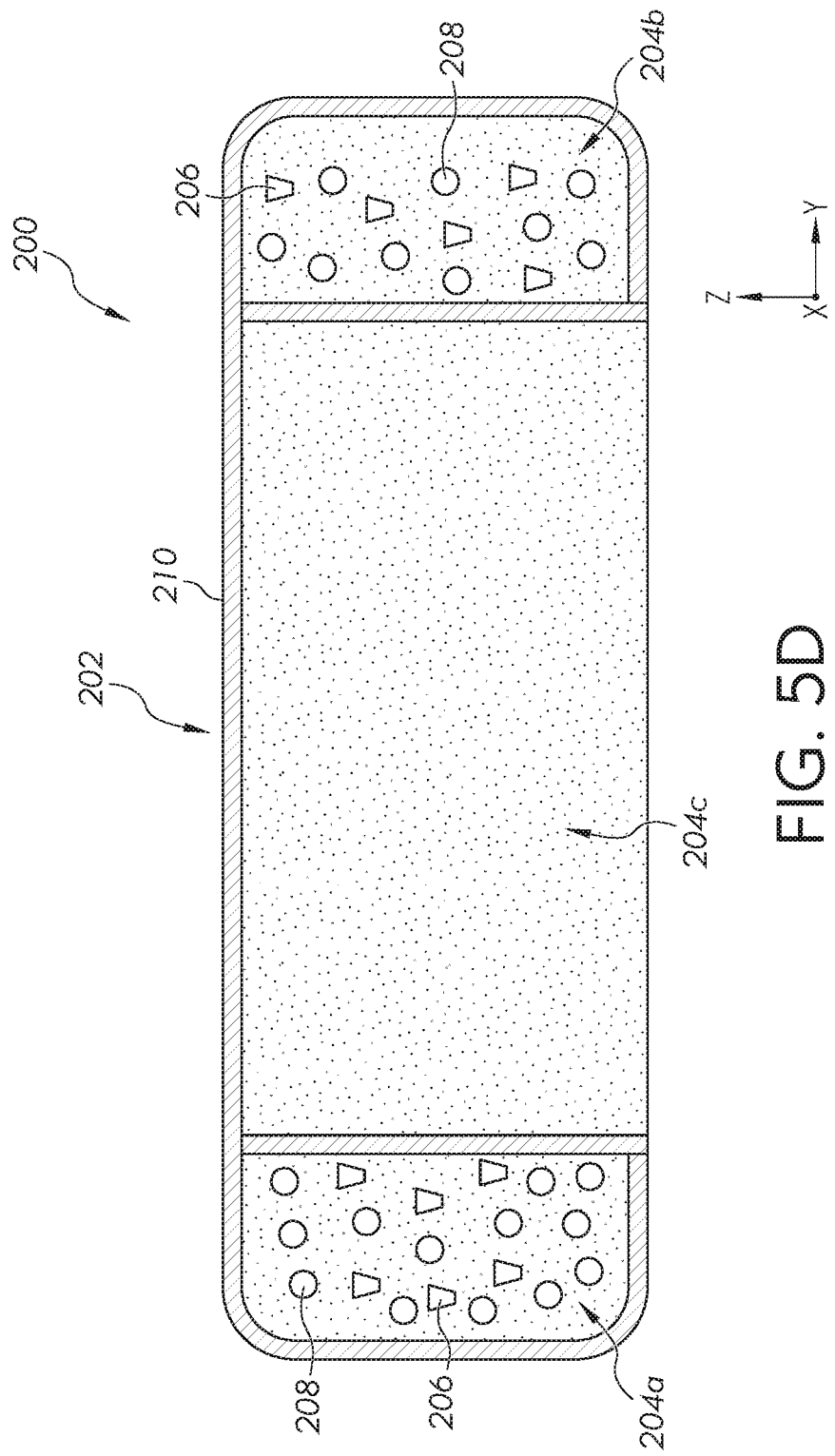
FIG. 5D schematically depicts a cross-section of a thermally conductive core portion in accordance with one or more embodiments described herein.

Referring now to FIG. 5D, another alternative embodiment of a thermally conductive core portion 200 is schematically depicted. In this embodiment, the thermally conductive core portion 200 includes a support matrix enclosed within a compliant shell 202. However, in this embodiment, the support matrix is formed from multiple parts. Specifically, the support matrix may include a first support matrix 204a and a second support matrix 204b enclosed within the compliant shell 202. In this embodiment, each support matrix 204a, 204b is formed from elastomeric gels, foams, oils, or fluids which comprise thermally conductive particles 206 and/or thermally absorptive elements 208 dispersed therein, as described herein with respect to FIG. 5B. However, it should be understood that each support matrix 204a, 204b may be constructed as described with respect to FIG. 5A, that is, from thermally absorptive materials.

In the embodiment depicted in FIG. 5D, the first support matrix 204a and the second support matrix 204b may be separated and spaced apart by a third support matrix 204c formed from different material than the first support matrix and the second support matrix. In the embodiment shown in FIG. 5D, the third support matrix 204c is attached to, but not disposed in, the compliant shell 202. However, in alternative embodiments (not shown) the third support matrix 204c may be disposed in the compliant shell 202 between the first support matrix 204a and the second support matrix 204b. In these embodiments, the third support matrix 204c may be formed from, for example and without limitation, foam such as urethane foam or polyurethane foam.

Still referring to FIG. 5D, in this embodiment of the thermally conductive core portion 200, at least the top surface 210 of the compliant shell 202 is formed from a thermally conductive material or, alternatively, from a material in which thermally conductive elements are incorporated, such that heat from the top surface 210 of the compliant shell may be conducted into each of the first support matrix 204a and the second support matrix 204b. That is, in this embodiment, each of the first support matrix 204a and the second support matrix 204b serve as reservoirs in which heat from the top surface 210 of the compliant shell 202 may be absorbed and dissipated.

For example, in embodiments, at least the top surface 210 of the compliant shell 202 includes thermally conductive elements having a relatively high thermal conductivity (e.g., greater than about 40 W/m*K). The thermally conductive elements may include for example and without limitation, metal particles or metal fibers formed from copper, alloys of copper, silver, alloys of silver, gold, alloys of gold, and the like. For example, in embodiments, at least the top surface 210 of the compliant shell 202 may be in the form of an elastomeric film which includes metal particulates or a layer of woven or non-woven metallic fibers. Alternatively, at least the top surface 210 of the compliant shell 202 may be formed from or incorporate a polymer material having a relatively high thermal conductivity (e.g., greater than about 40 W/m*K) such as particles or fibers formed from ultra-high molecular weight polyethylene, polypropylene, liquid crystalline polymer, polyphthalamide, polycarbonate, or the like. For example, in embodiments, at least the top surface 210 of the compliant shell 202 may be in the form of an elastomeric film which includes thermally conductive polymer particles or a layer of woven or non-woven thermally conductive polymer fibers. As yet another alternative, at least the top surface 210 of the compliant shell 202 may be formed from or incorporate carbon fiber or carbon nanotubes having a relatively high thermal conductivity (e.g., greater than about 40 W/m*K). For example, in embodiments, at least the top surface 210 of the compliant shell 202 may be in the form of an elastomeric film which includes thermally conductive carbon particulates or a layer of woven or non-woven thermally conductive carbon fibers.

In the embodiment of the thermally conductive core portion 200 depicted in FIG. 5D, at least the top surface 210 of the compliant shell 202 assists in conducting heat into the first support matrix 204a and the second support matrix 204b. For example, when the thermally conductive core portion 200 is positioned in the support pad and a subject (not shown) is positioned on the top surface of the support pad over and in contact with the top surface 210 of the compliant shell 202, heat from the subject is conducted through and along the top surface 210 of the compliant cover and into support matrix 204a and support matrix 204b where the heat is dissipated. The conduction of heat into the support matrix 204a and the support matrix 204b of the thermally conductive core portion 200 results in the localized cooling of the portion of the subject positioned over the thermally conductive core portion 200.

Figure 5E:
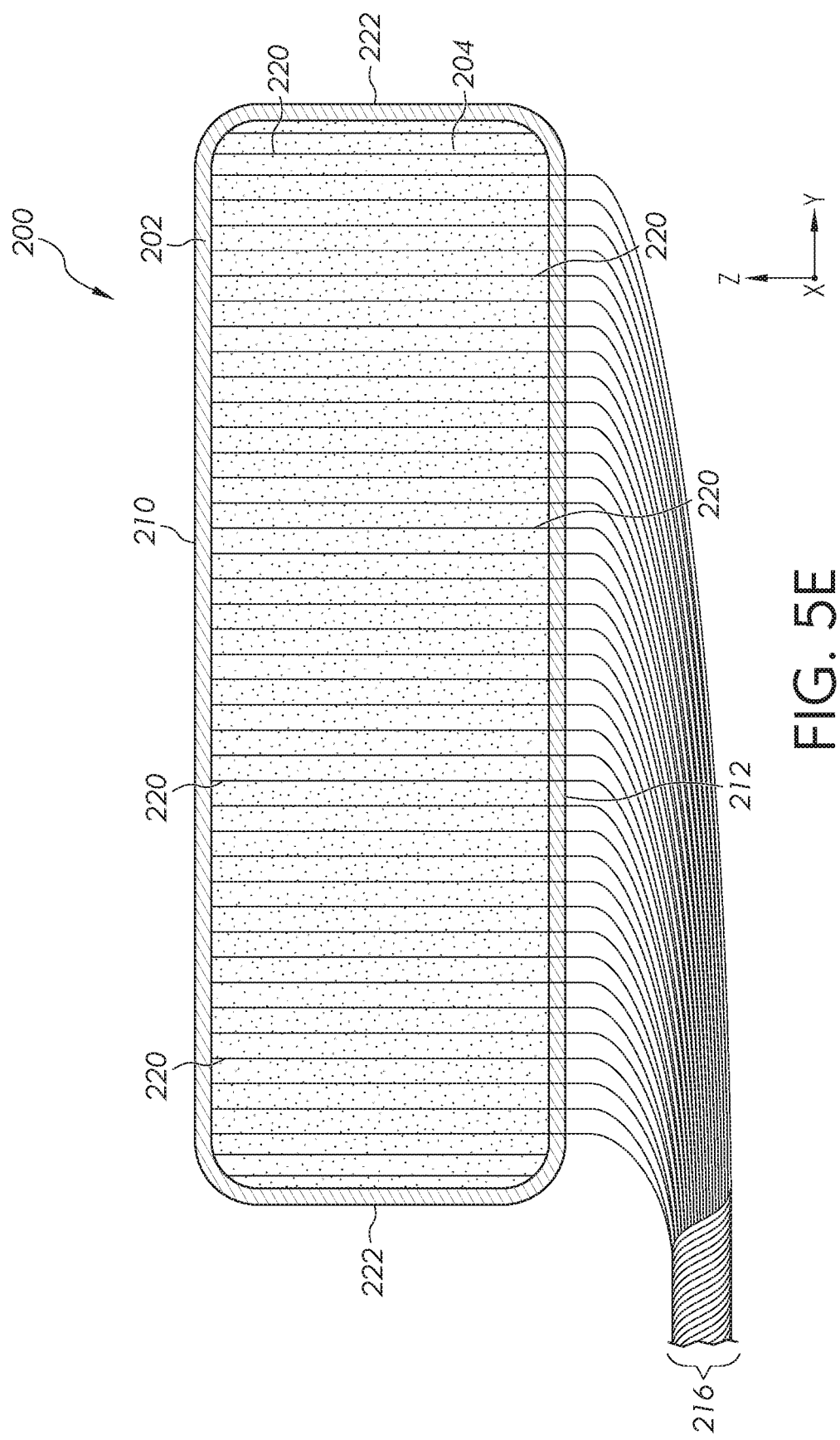
FIG. 5E schematically depicts a cross-section of a thermally conductive core portion in accordance with one or more embodiments described herein.
Figure 5F:
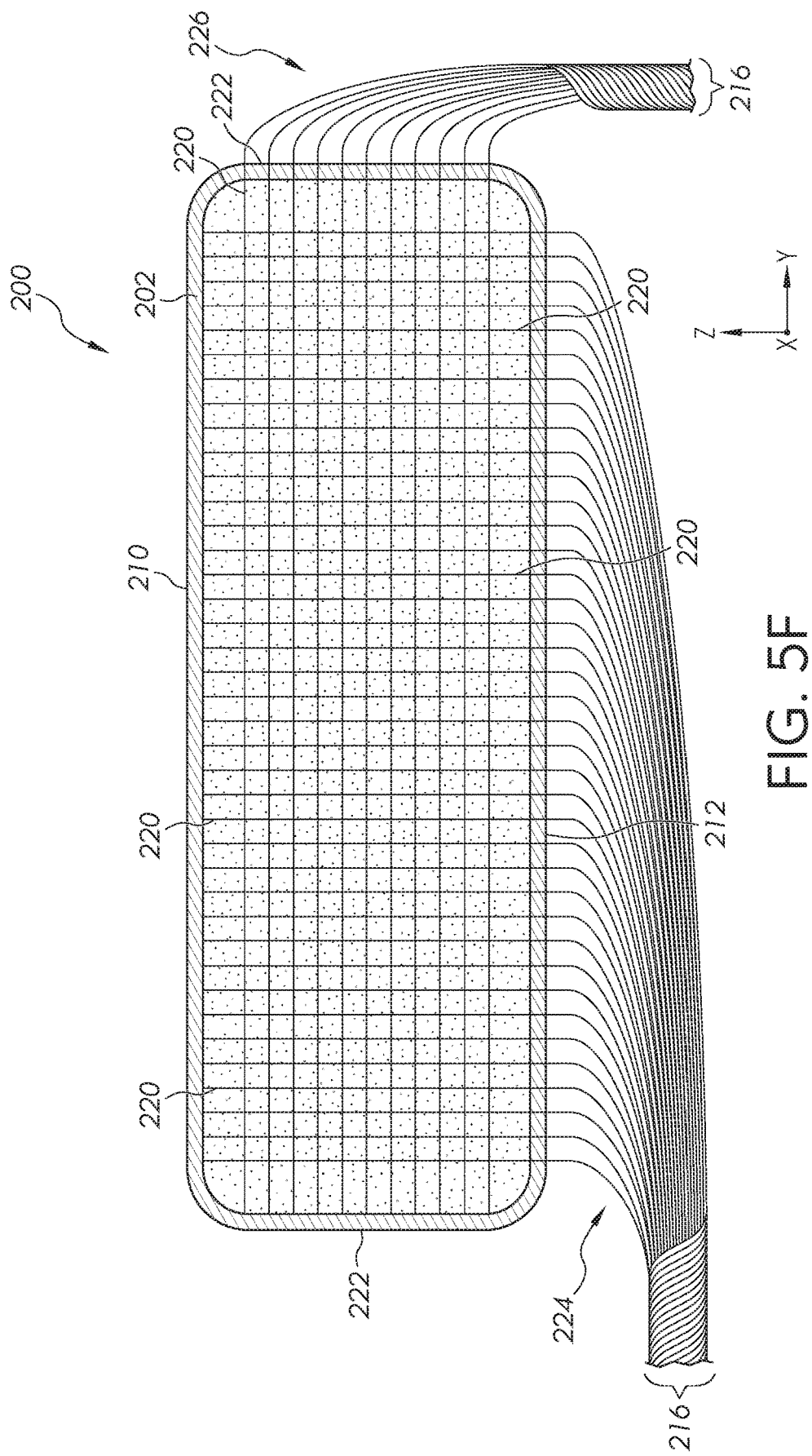
FIG. 5F schematically depicts a cross-section of a thermally conductive core portion in accordance with one or more embodiments described herein.
Figure 5G:
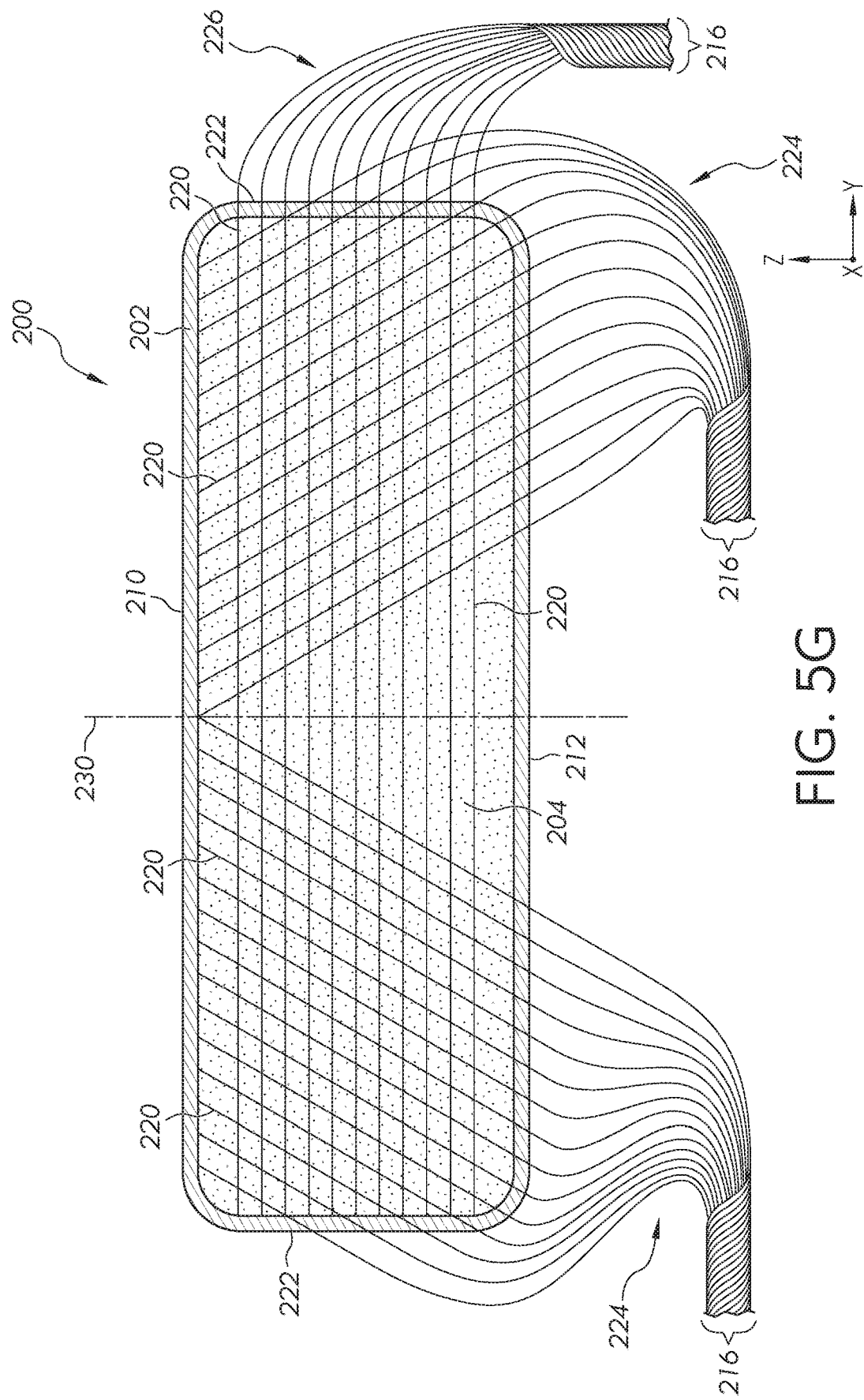
FIG. 5G schematically depicts a cross-section of a thermally conductive core portion in accordance with one or more embodiments described herein.

Referring now to FIGS. 5E-5G, alternative embodiments of thermally conductive core portions 200 are schematically depicted. These embodiments of the thermally conductive core portions 200 include a support matrix 204 enclosed within a compliant shell 202, as described herein with respect to FIGS. 5A and 5B. The compliant shell 202 of the thermally conductive core portion 200 may be formed from the same materials and have the same dimensions as described hereinabove with respect to FIGS. 5A and 5B. Further, in the embodiments of the thermally conductive core portions 200 depicted in FIGS. 5E-5G, the support matrix 204 may be formed from, for example, phase change materials, elastomeric gels, foams, oils, or fluids as described herein with respect to FIG. 5B. In some embodiments, the support matrix may be formed from, for example, thermally absorptive materials including, without limitation, phase change materials, oils with high heat capacity, water, cooling fluids, and the like. Suitable phase change materials include, without limitation, alkanes having a melting temperature greater than or equal to about 5° C. and less than or equal to about 35° C. Examples of suitable alkanes include, without limitation, tetradecane, pentadecane, hexadecane, heptadecane, octadecane, and nonadecane. Suitable elastomeric gels may include, without limitation, silicone gels, urethane gels, polyurethane gels and the like. Suitable oils may include, without limitation, inorganic oils, silicone oils, mineral oils, and the like. Suitable foams may include, without limitation, urethane foam, polyurethane foam, and the like. Suitable fluids may include, without limitation, water, cooling fluids, or mixtures of water and cooling fluids. In embodiments where the support matrix 204 includes a fluid, the support matrix 204 may further include an antimicrobial agent to resist microbial growth. Although not depicted in FIGS. 5E-5G, the thermally conductive core portions 200 may optionally include thermally conductive particles and/or thermally absorptive particles dispersed in the support matrix 204 as described herein with respect to FIG. 5B. However, it should be understood that the thermally conductive particles and/or thermally absorptive particles are optional and that the thermally conductive core portions 200 depicted in FIGS. 5E-5G may be formed without thermally conductive particles and/or thermally absorptive particles dispersed in the support matrix 204.

In the embodiments of the thermally conductive core portion 200 depicted in FIGS. 5E-5G, the support matrix 204 may further include thermally conductive elements, such as an array of thermally conductive fibers 220, suspended within the support matrix 204 to facilitate the conduction of heat through the support matrix 204 and away from the top surface 210 of the thermally conductive core portion 200. In these embodiments, the thermally conductive fibers 220 may have a relatively high thermal conductivity (e.g., greater than about 40 W/m*K). For example, in embodiments, the thermally conductive fibers 220 may have a thermal conductivity of from about 40 W/m*K to about 2000 W/m*K, from about 60 W/m*K to about 1000 W/m*K, from about 80 W/m*K to about 500 W/m*K, or even from about 100 W/m*K to about 300 W/m*K. Examples of thermally conductive fibers 220 include, without limitation, metallic fibers, carbon fibers, polymer fibers and combinations thereof. Suitable metallic fibers include, without limitation, copper fibers, copper alloy fibers, silver fibers, silver alloy fibers, gold fibers, gold alloy fibers, and the like. Suitable polymer fibers include, without limitation, ultra-high molecular weight polyethylene fibers, polypropylene fibers, liquid crystalline polymer fibers, polyphthalamide fibers, polycarbonate fibers, and the like. Suitable carbon fibers include, without limitation, pitch-based carbon fibers.

In the embodiments of the thermally conductive core portions 200 depicted in FIGS. 5E-5G, the thermally conductive fibers 220 of the array of fibers may be arranged in various orientations within the support matrix 204. In general, at least a portion of the array of thermally conductive fibers 220 extend from at least one of a side surface 222 of the thermally conductive core portion 200 and a bottom surface 212 of the thermally conductive core portion 200. In embodiments, at least a portion of the array of thermally conductive fibers 220 extends towards a top surface 210 of the thermally conductive core portion 200. In some embodiments, the thermally conductive fibers 220 extend to and contact the compliant shell 202, as depicted in FIGS. 5E-5G. In some other embodiments, the thermally conductive fibers 220 extend towards the top surface 210 of the thermally conductive core portion 200 but are spaced apart from the compliant shell 202. In embodiments, a portion if the support matrix 204 is disposed between the thermally conductive fibers 220 and the compliant shell 202. In some other embodiments, an optional spacer layer (not shown) is disposed between the thermally conductive fibers 220 and the compliant shell 202. In embodiments, the spacer layer may include a woven or non-woven batting or scrim formed from non-conductive fibers (such as polyester, cotton, or the like) or a combination of non-conductive fibers and conductive fibers (such as carbon fiber, metallic fibers, and/or polymer fibers).

In the embodiment of the thermally conductive core portion 200 depicted in FIG. 5E, the array of thermally conductive fibers 220 includes a plurality of fibers which extend from the bottom surface 212 of the thermally conductive core portion 200 towards the top surface 210. In this embodiment the thermally conductive fibers 220 in the array are generally parallel with one another and to the vertical direction (i.e., the +/−Z direction of the coordinate axes depicted in the figures). That is, the thermally conductive fibers are generally perpendicular to the top surface 210 of the thermally conductive core portion. The thermally conductive fibers 220 in this embodiment extend through the bottom surface 212 of the compliant shell 202 and may be bundled together to form a pigtail connector 216. The pigtail connector 216 may be thermally coupled to a cooling source (not shown) as described in further detail herein.

Referring to FIGS. 4B and 5E, when the thermally conductive core portion 200 is positioned in the support pad 130 and a subject (not shown) is positioned on the top surface 131 of the support pad 130 over the thermally conductive core portion 200, heat from the subject is conducted into the support matrix 204, through the support matrix 204 with the thermally conductive fibers 220, and through the pigtail connector 216 to a cooling source where the heat is dissipated. The conduction of heat into and through the thermally conductive core portion 200 results in the localized cooling of the portion of the subject positioned over the thermally conductive core portion 200.

Referring now to FIG. 5F, in embodiments, the thermally conductive elements, specifically the array of thermally conductive fibers 220, includes a first plurality of thermally conductive fibers 224 and a second plurality of thermally conductive fibers 226. In the embodiment of the thermally conductive core portion 200 depicted in FIG. 5F, the first plurality of thermally conductive fibers 224 are the fibers 220 generally parallel to the +/−Z direction of the coordinate axes depicted in the figure and the second plurality of thermally conductive fibers 226 are the fibers generally parallel to the +/−Y direction of the coordinate axes depicted in the figure (i.e., generally parallel to the top surface 210 of the thermally conductive core portion). Accordingly, it should be understood that the first plurality of thermally conductive fibers 224 and the second plurality of thermally conductive fibers 226 are generally perpendicular with one another. In embodiments, the first plurality of thermally conductive fibers 224 intersect with and contact the second plurality of thermally conductive fibers 226 and, as such, the first and second pluralities of thermally conductive fibers 224, 226 are directly thermally coupled to one another. In some other embodiments, the first plurality of thermally conductive fibers 224 do not contact the second plurality of thermally conductive fibers 226 and, as such, the first and second pluralities of thermally conductive fibers 224, 226 are indirectly thermally coupled to one another. The first plurality of thermally conductive fibers 224 extend through the bottom surface 212 of the compliant shell 202 and may be bundled together to form a pigtail connector 216 while the second plurality of thermally conductive fibers 226 extend through the side surface 222 of the compliant shell 202 and may be bundled together to form a pigtail connector 216. The pigtail connectors 216 may be thermally coupled to a cooling source (not shown) as described in further detail herein.

Referring to FIGS. 4B and 5F, when the thermally conductive core portion 200 is positioned in the support pad 130 and a subject (not shown) is positioned on the top surface 131 of the support pad 130 over the thermally conductive core portion 200, the first plurality of thermally conductive fibers 224 conducts heat from the top surface 210 of the thermally conductive core portion 200 through the support matrix 204 in a vertically downward direction (i.e., in the −Z direction of the coordinate axes depicted in the figure) towards and through the bottom surface 212 of the thermally conductive core portion 200, thereby expelling heat from the interior of the thermally conductive core portion 200 through the pigtail connector 216 formed from the first plurality of thermally conductive fibers 224. The second plurality of thermally conductive fibers 226 assists the first plurality of thermally conductive fibers 224 in expelling heat from the interior of the thermally conductive core portion. Specifically, as the first plurality of thermally conductive fibers 224 conducts heat away from the top surface 210, at least a portion of the heat is coupled into the second plurality of thermally conductive fibers 226 which conduct the heat laterally (i.e., in the +/−Y direction of the coordinate axes depicted in the figure) towards and through the side surface 222 of the thermally conductive core portion 200, thereby expelling heat from the interior of the thermally conductive core portion 200 through the pigtail connector 216 formed by the second plurality of thermally conductive fibers 226.

In embodiments, the fibers of the first plurality of thermally conductive fibers 224 may have substantially the same thermal conductivity as the second plurality of thermally conductive fibers 226. Alternatively, the fibers of the first plurality of thermally conductive fibers 224 may have greater thermal conductivity than the second plurality of thermally conductive fibers 226.

In embodiments, the second plurality of thermally conductive fibers 224 includes fibers having different thermal conductivities. In these embodiments, the fibers of the second plurality of thermally conductive fibers 224 are arranged in the support matrix 204 such that fibers having relatively greater thermal conductivities are positioned closer to the top surface 210 of the thermally conductive core portion 200 than fibers having a relatively lower thermal conductivity. While not wishing to be bound by theory, it is believed that having fibers with relatively greater thermal conductivities proximate the top surface 210 of the thermally conductive core portion 200 may enhance the extraction of heat away from the top surface 210 of the thermally conductive core portion 200 and into the support matrix 204.

In embodiments, the second plurality of thermally conductive fibers 226 are evenly distributed throughout the support matrix 204. In some other embodiments, the second plurality of thermally conductive fibers 226 are distributed in the support matrix 204 such that the density of the second plurality of thermally conductive fibers 226 in the support matrix 204 (i.e., the number of fibers 220 per unit volume of the support matrix 204) is greatest proximate the top surface 210 of the thermally conductive core portion 200 and decreases with increasing distance from the top surface 210 of the thermally conductive core portion 200. While not wishing to be bound by theory, it is believed that having a greater density of second plurality of thermally conductive fibers 226 proximate the top surface 210 of the thermally conductive core portion 200 may enhance the extraction of heat from the top surface 210 of the thermally conductive core portion 200 and into the support matrix 204.

While FIG. 5F schematically depicts the first plurality of thermally conductive fibers 224 as substantially perpendicular to the second plurality of fibers 226, it should be understood that other embodiments are contemplated and possible. For example, FIG. 5G depicts an alternative embodiment of the array of thermally conductive fibers 220. In this embodiment, the second plurality of fibers 226 are the fibers generally parallel to the +/−Y direction of the coordinate axes depicted in the figure. However, in this embodiment, the first plurality of thermally conductive fibers 224 are obliquely oriented with respect to the second plurality of thermally conductive fibers 226. Specifically, in this embodiment, the first plurality of thermally conductive fibers 224 are arranged at an angle with respect to the Z axis to conduct heat laterally, away from the mid-line 230 of the thermally conductive core portion 200. Arranging the first plurality of thermally conductive fibers 224 in this configuration may enhance the extraction of heat from the thermally conductive core portion 200.

Still referring to FIG. 5G, in embodiments, the fibers of the first plurality of thermally conductive fibers 224 may have substantially the same thermal conductivity as the second plurality of thermally conductive fibers 226. Alternatively, the fibers of the first plurality of thermally conductive fibers 224 may have greater thermal conductivity than the second plurality of thermally conductive fibers 226.

In embodiments, the second plurality of thermally conductive fibers 224 includes fibers having different thermal conductivities. In these embodiments, the fibers of the second plurality of thermally conductive fibers 224 are arranged in the support matrix 204 such that fibers having relatively greater thermal conductivities are positioned closer to the top surface 210 of the thermally conductive core portion 200 than fibers having a relatively lower thermal conductivity. While not wishing to be bound by theory, it is believed that having fibers with relatively greater thermal conductivities proximate the top surface 210 of the thermally conductive core portion 200 may enhance the extraction of heat away from the top surface 210 of the thermally conductive core portion 200 and into the support matrix 204.

In embodiments, the second plurality of thermally conductive fibers 226 are evenly distributed throughout the support matrix 204. In some other embodiments, the second plurality of thermally conductive fibers 226 are distributed in the support matrix 204 such that the density of the second plurality of thermally conductive fibers 226 in the support matrix 204 (i.e., the number of fibers 220 per unit volume of the support matrix 204) is greatest proximate the top surface 210 of the thermally conductive core portion 200 and decreases with increasing distance from the top surface 210 of the thermally conductive core portion 200. While not wishing to be bound by theory, it is believed that having a greater density of second plurality of thermally conductive fibers 226 proximate the top surface 210 of the thermally conductive core portion 200 may enhance the extraction of heat from the top surface 210 of the thermally conductive core portion 200 and into the support matrix 204.

Figure 6:
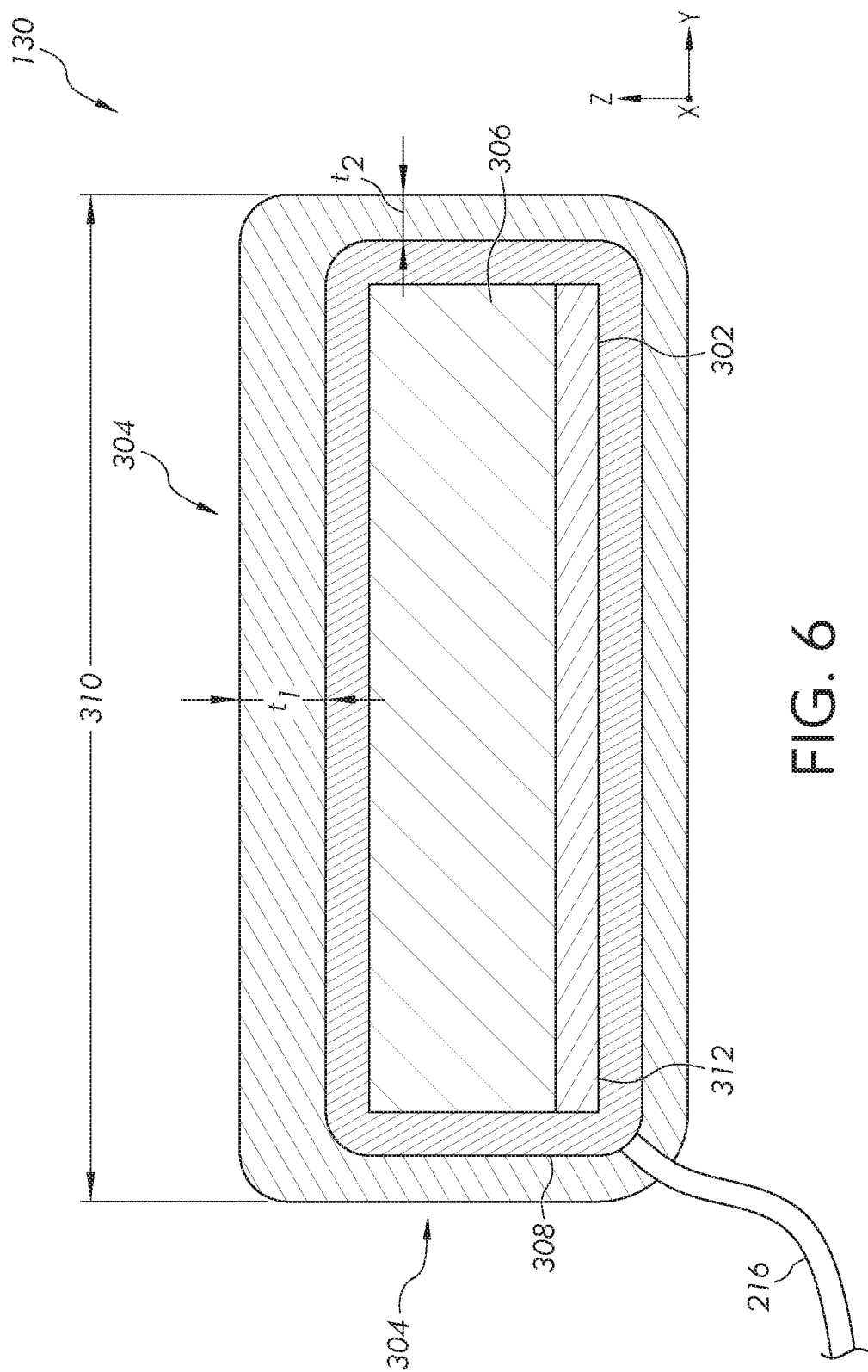
FIG. 6 schematically depicts a cross-section of a support pad including a thermally conductive in accordance with one or more embodiments described herein.

Referring now to FIG. 6, an alternative embodiment of a portion of a support pad 130 is schematically depicted in cross section. In this embodiment, the support pad 130 may include a cover 304 (i.e., a cover material) with a cushioning material 306 (i.e., a support matrix), such as foam or the like, and a cooling feature in the form of a thermally conductive element 308 disposed between the substrate 302 and the cover 304. In embodiments, the support pad 130 may optionally include a rigid substrate 302 positioned beneath the cushioning material 306. In embodiments, the thermally conductive element 308 may include thermally conductive fibers, thermally conductive films, or the like. In some embodiments, the support pad 130 may include a contoured or a shaped surface to accommodate a specific portion of a patient. For example, a support pad 130 positioned to support a subject's head may be contoured to correspond to an approximate shape and size of a subject's head. Alternatively, a support pad 130 positioned to support a subject's head may include an aperture to accommodate a subject's facial features (i.e., eyes, nose, and/or mouth).

In the embodiment depicted in FIG. 6, the thermally conductive element 308 is positioned between the cover 304 and the cushioning material 306. Alternatively, the thermally conductive element 308 may be embedded in and/or dispersed throughout the cushioning material, as described herein with respect to FIGS. 5B-5F. In embodiments, the thermally conductive element 308 and the cover 304 extend laterally (i.e., generally along the Y axis of the coordinate axes depicted in FIG. 6) beyond the cushioning material 306 and the optional substrate 302 in the embodiment of FIG. 6. For example, the cover 304 and the thermally conductive element 308 may wrap around the edges of the cushioning material 306 and the substrate 302, enveloping the cushioning material 306. In some embodiments, the cover 304 and/or the thermally conductive element 308 may be coupled to a bottom surface 312 of the optional substrate 302 of the cushioning material 306 such as by an adhesive, mechanical fasteners, or the like. In the embodiment of the support pad 130 depicted in FIG. 6, the cushioning material 306 and the thermally conductive element 308 are the thermally conductive core portion of the support pad 130.

The optional substrate 302 may be a rigid material to provide structure and support for the support pad 130. For example, the optional substrate 302 may be a rigid plastic or a composite that is radiolucent. In some embodiments, the optional substrate 302 may be a foam with an indentation load deflection (ILD) value that is suitable to provide support without producing unnecessarily high pressures on the subject supported by the support surface. It is contemplated that other materials may be used as a substrate 302, provided that they do not degrade the radiolucency of the support pad 130.

In the embodiments described herein, the cover 304 may be an elastomer, gel, or other protective material to protect the cushioning material 306 and the thermally conductive element 308 from fluids or biological materials. For example, in embodiments, the cover 304 may be fluid impermeable, such that water and/or biological fluids do not pass through the cover 304 and contaminate the cushioning material 306 and/or the thermally conductive element 308. Suitable materials for the cover 304 may include, for example, urethane, nylon and/or Lycra material. In embodiments, the cover 304 may be formed from the same material as the cover material described herein with respect to FIGS. 4A and 4B. However, it is contemplated that other materials may be used as a cover 304, provided that they do not degrade the radiolucency of the support pad 130. In some embodiments, the cover 304 may be removable and/or washable, enabling it to be changed and/or washed.

As shown in FIG. 6, in some embodiments, the cover 304 may have a first thickness $t_1$ at a person support surface 310 and a second thickness $t_2$ at a portion of the support pad that does not form the person support surface 310. For example, the cover 304 may have a first thickness $t_1$ over the cushioning material 306 and a second thickness $t_2$ over areas in which the thermally conductive element 308 extend beyond the top of the cushioning material 306, such as adjacent to the side of the cushioning material. In various embodiments, the first thickness $t_1$ is greater than the second thickness $t_2$. In such embodiments, the increased thickness of the first thickness $t_1$ in relation to the second thickness $t_2$ provides insulation which prevents heat drawn away from the person support surface 310 from returning to that surface. Instead, the heat is transferred away from the person support surface 310, thus providing a cooling effect. More specifically, the greater thickness of $t_1$ may reduce or eliminate the passage of heat from the thermally conductive element 308 back to the subject positioned on the person support surface 310.

Alternatively, or in addition to the varying thickness of the cover 304, an optional thermal shield may be positioned between the thermally conductive element 308 and the cover 304. The thermal shield may be, for example, a polyethylene terephthalate, or polyester, film (e.g., Mylar®) or other thermally reflective material positioned to reflect heat toward the thermally conductive element 308. It is contemplated that other materials may be used as a thermal shield, provided that they do not negatively impact the radiolucency of the support pad 130. In such embodiments, as heat is transferred from the cover 304 at the person support surface 310 to the thermally conductive element 308, the thermal shield reduces or eliminates the amount of heat that returns to the cover 304 at the person support surface 310.

The cushioning material 306 may be any type of material suitable for providing support to the subject on the person support surface 310 without producing unnecessarily high pressures on the subject supported by the person support surface 310. For example, the cushioning material 306 can be a foam, gel, other material, or combinations thereof. In some embodiments, the cushioning material 306 may be in the form of a fluid-filled bladder. The fluid may be, for example, a liquid or gas. In still other embodiments, multiple layers of cushioning material 306 may be included. The layers may include the same materials or different materials, depending on the particular embodiment. For example, a layer of foam and a layer of gel may be employed, or two layers of foam may be employed. As with the substrate 302 and the cover 304, in various embodiments, the cushioning material 306 is made of a radiolucent material.

The cushioning material 306 may be planar or contoured, depending on the specific use of the support pad 130. For example, the cushioning material 306 may have a uniform thickness, as depicted in FIG. 6, or it may have a thickness that varies along the length and/or width of the support pad 130. In some embodiments, the variation in the thickness of the cushioning material 306 may be based on a portion of the anatomy of the subject supported by the support pad 130. For example, a support pad intended for use in supporting a hip may have a first thickness profile, while a support pad intended for use in supporting a shoulder may have a second thickness profile. In addition to varying thicknesses of the cushioning material 306, the shape of the cushioning material 306 may also vary depending on the particular use of the support pad 130. For example, the cushioning material 306 may be rectangular, annular, hexagonal, or another suitable shape.

In various embodiments, the thermally conductive element 308 is positioned between the cover 304 and the cushioning material 306. As noted herein, the thermally conductive element 308 and the cushioning material 306 together form the thermally conductive core portion of the support pad 130 depicted in FIG. 6. In embodiments, when the support pad 130 is positioned on the longitudinal frame 125 of a person support system 100, 101 (FIGS. 1-3), the thermally conductive element 308 is oriented across the support pad 130 in a direction perpendicular to the longitudinal direction of the longitudinal frame 125 (e.g., along the Y axis in FIG. 1) to facilitate coupling the thermally conductive element to a cooling fluid and/or cooling fluid source through the side rails 126, 127, as will be described in further detail herein.

As provided above, in various embodiments, the thermally conductive element 308 extends beyond the person support surface 310. For example, the thermally conductive element 308 may extend to an area of the support pad 130 that is not contacted or covered by a subject supported by the support pad 130, such as the sides of the support pad 130. In various embodiments, the thermally conductive element 308 has an area that is not covered by the subject that is a minimum of about 25% of the area of the thermally conductive element 308. The extension of the thermally conductive element 308 to an area of the support pad 130 that is not in contact with the subject supported by the support pad 130 enables formation of a temperature gradient along the thermally conductive element 308, which in turn enables the thermally conductive element 308 to function as a cooling mechanism for the support pad 130.

That is, the thermally conductive element 308 may include two areas, a source region and a sink region. The source region includes the portions of the thermally conductive element 308 that is covered by a subject supported by the support pad 130. The sink region includes the portions of the thermally conductive element 308 that is not covered by a subject supported by the support pad 130. The area of the sink region may be at least 25% of the area of the source region. In some embodiments, the area of the sink region may be from about 25% to about 200% of the area of the source region, from about 30% to about 100% of the area of the source region, or from about 40% to about 80% of the area of the source region. The sink region withdraws heat from the source region, thus removing heat from the person support surface 310 and directing it away from the interface between the subject supported by the support pad 130 and the cover 304 of the support pad 130.

Still referring to FIG. 6, in various embodiments, the thermally conductive element 308 may include thermally conductive fibers, thermally conductive films, and the like. In embodiment, the thermally conductive fibers having a thermal conductivity of greater than about 40 W/m*K. For example, the thermally conductive fibers may have a thermal conductivity of from about 40 W/m*K to about 2000 W/m*K, from about 60 W/m*K to about 1000 W/m*K, from about 80 W/m*K to about 500 W/m*K, or from about 100 W/m*K to about 300 W/m*K. Suitable fibers may include, for example, carbon fibers and/or polymer fibers. In one particular example, the thermally conductive fibers may include pitch-based carbon fiber. Alternatively or additionally, the thermally conductive fibers may include polymer fibers formed from ultra-high molecular weight polyethylene fibers, polypropylene fibers, liquid crystalline polymer fibers, polyphthalamide fibers, polycarbonate fibers, and the like. Other materials having a suitable thermal conductivity are contemplated, including, without limitation, metallic fibers as described herein. In embodiments where the thermally conductive element 308 is formed from thermally conductive fibers, the fibers may be arrayed in a linear pattern (i.e., parallel with one another). Alternatively, the thermally conductive fibers may have a zig-zag or sinusoidal configuration. As yet another alternative, the thermally conductive fibers may be interwoven to form a thermally conductive fabric.

When the thermally conductive element 308 is a film, the film may be formed from, for example and without limitation, thermally conductive polymer materials. Suitable polymer films include polymer films having a thermal conductivity of greater than about 40 W/m*K. For example, the polymer film may have a thermal conductivity of from about 40 W/m*K to about 2000 W/m*K, from about 60 W/m*K to about 1000 W/m*K, from about 80 W/m*K to about 500 W/m*K, or from about 100 W/m*K to about 300 W/m*K. Suitable polymer materials for the film include, without limitation, ultra-high molecular weight polyethylene, polypropylene, liquid crystalline polymer, polyphthalamide, polycarbonate, and the like.

Furthermore, in the various embodiments of the support pads and thermally conductive core portions described herein (i.e., the thermally conductive core portions depicted in FIGS. 5A-5G and the support pad of FIG. 6), the thermally conductive elements (i.e., fibers, films, etc.) incorporated in the support pads may have a value of k×T of from about 0.006 W/K to about 12 W/K, from about 0.02 W/K to about 10 W/K, or from about 0.05 W/K to about 6 W/K. These values represent the mean directional thermal conductivity k (in Watts per meter degree Kelvin or W/m*K) and the total thickness T (in meters) of the thermally conductive element. The two values are specified together because there is an inverse relationship between the mean thermal conductivity k of the material and the thickness of the layer required to conduct sufficient heat to cool the skin under a set of typical thermal conditions for such applications. Table 1 reflects constraints on the conductivity (k) of the thermally conductive element and the thickness (T) of the element such that k×T is greater than or equal to about 0.006 W/K and less than about 12 W/K.

TABLE 1

Depth of Conductive Material for Given Conductivity Over Range of k × T from 0.006 W/K to 12 W/K

| Conductivity | Minimum Depth | | Maximum Depth | |
|---|---|---|---|---|
| (W/m * K) | (m) | (cm) | (m) | (cm) |
| 40 | 0.000150 | 0.015 | 0.300 | 30.00 |
| 60 | 0.000100 | 0.010 | 0.200 | 20.00 |
| 80 | 0.000075 | 0.008 | 0.150 | 15.00 |
| 100 | 0.000060 | 0.006 | 0.120 | 12.00 |
| 125 | 0.000048 | 0.005 | 0.06 | 9.60 |
| 150 | 0.000040 | 0.004 | 0.080 | 8.00 |
| 200 | 0.000030 | 0.0030 | 0.060 | 6.00 |
| 300 | 0.000020 | 0.0020 | 0.040 | 4.00 |
| 500 | 0.000012 | 0.0012 | 0.024 | 2.40 |
| 1000 | 0.000006 | 0.0006 | 0.012 | 1.20 |
| 2000 | 0.000003 | 0.0003 | 0.006 | 0.60 |

Referring again to FIG. 6, in embodiments, the support pad 130 may optionally further include a pigtail connector 216 thermally coupled to the thermally conductive element 308. The pigtail connector 216 may be used to couple the thermally conductive element 308 to a cooling source (described in further detail herein), thereby facilitating the extraction of heat from the support pad 130. In embodiments, the pigtail connector 216 may be formed from, for example and without limitation, thermally conductive material having a thermal conductivity of greater than about 40 W/m*K. For example, the thermally conductive material of the pigtail connector 216 may have a thermal conductivity of from about 40 W/m*K to about 2000 W/m*K, from about 60 W/m*K to about 1000 W/m*K, from about 80 W/m*K to about 500 W/m*K, or from about 100 W/m*K to about 300 W/m*K. In one particular example, the thermally conductive material may be carbon fiber, such as pitch-based carbon fibers. Alternatively, the thermally conductive elements may be polymer fibers or strips, such as polymer fibers or strips formed from ultra-high molecular weight polyethylene, polypropylene, liquid crystalline polymer, polyphthalamide, polycarbonate, or the like.

Referring now to FIGS. 5B-5G and FIG. 6, embodiments of the support pad 130 and/or the thermally conductive core portion 200 of the support pad 130 may include a pigtail connector 216, as described herein, to thermally couple the support pad 130 and/or the thermally conductive core portion 200 of the support pad 130 to a cooling source (i.e., a cooling source external to the thermally conductive core portion 200). The cooling source further aids in conducting and dissipating heat from the top surface of the support pad 130. In some embodiments, the pigtail connector 216 may further include a coupler to assist in thermally coupling the pigtail connector 216 to the cooling source and/or the side rails of a person support system.

Figure 7A:
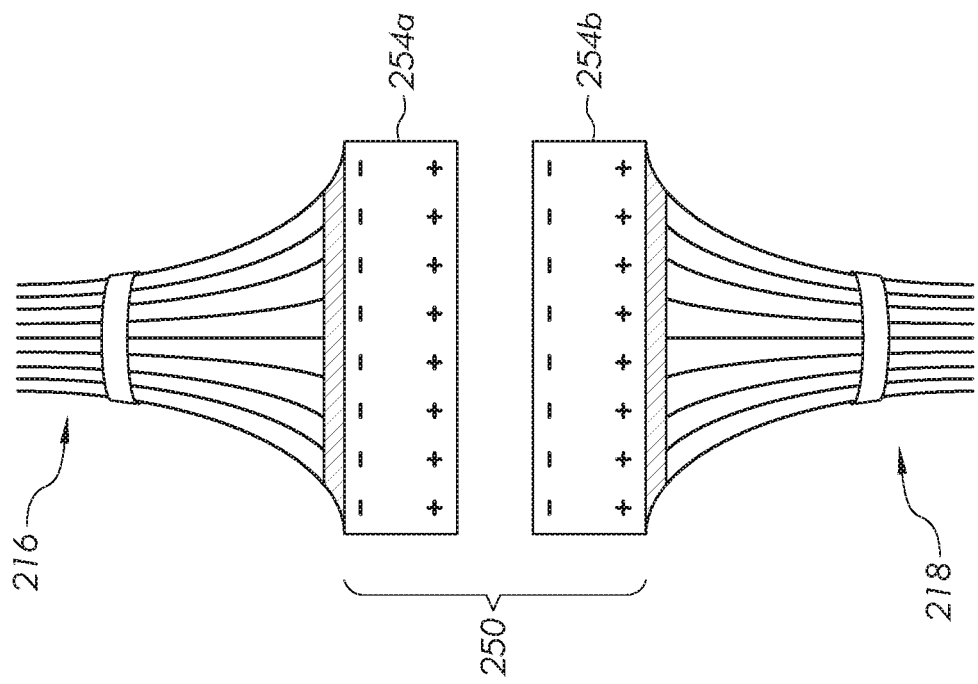
FIG. 7A schematically depicts a cross-section of a magnetic coupler in accordance with one or more embodiments described herein.

Referring to FIG. 7A by way of example, one embodiment of a magnetic coupler 250 is schematically depicted. In this embodiment the magnetic coupler 250 includes a first coupler body 252a and a second coupler body 252b. The first coupler body 252a includes a magnet 254a positioned in a holder 256a. Similarly, the second coupler body 252b includes a magnet 254b positioned in a holder 256b. The magnets 254a, 254b may be, for example and without limitation, ferrite magnets, rare earth magnets, sintered AlNiCo magnets, and the like. The holders 256a, 256b may be formed from thermally conductive materials such as thermally conductive metals, thermally conductive polymers, and the like. For example, in some embodiments, the holders 256a, 256b are formed from copper or a copper alloy. Alternatively, the holders 256a, 256b are formed from thermally conductive polymers such as ultra-high molecular weight polyethylene, polypropylene, liquid crystalline polymer, polyphthalamide, polycarbonate, and the like.

The magnets 254a, 254b are arranged in their respective holders 256a, 256b such that the magnets 254a, 254b are mutually attracted, thereby coupling the first coupler body 252a and the second coupler body 252b to one another and, hence, thermally coupling holder 256a of the first coupler body 252a to holder 256b of the second coupler body 252b. That is, the magnets 254a, 254b are arranged such that the "+" pole piece of either magnet 254a or magnet 254b mates with the "−" pole piece of the other of magnet 254a and 254b.

Still referring to FIG. 7A, a pigtail connector 216 may be thermally coupled to the first coupler body 252a with a thermally conductive adhesive to facilitate good thermal conduction between the thermally conductive material of the pigtail connector 216 and the first coupler body 252a. Alternatively, the pigtail connector 216 may be embedded in or fused to the first coupler body 252a to facilitate good thermal conduction between the thermally conductive material of the pigtail connector 216 and the first coupler body 252a.

In the embodiment of the magnetic coupler 250 depicted in FIG. 7A, the second coupler body 252b may optionally comprise a second pigtail connector 218. The second pigtail connector 218 may be used to couple the magnetic coupler to, for example, a cooling source (not depicted). The second pigtail connector 218 may be thermally coupled to the second coupler body 252b with a thermally conductive adhesive to facilitate good thermal conduction between the thermally conductive material of the second pigtail connector 218 and the second coupler body 252b. Alternatively, the second pigtail connector 218 may be embedded in or fused to the second coupler body 252b to facilitate good thermal conduction between the thermally conductive material of the second pigtail connector 218 and the second coupler body 252b.

Figure 7B:
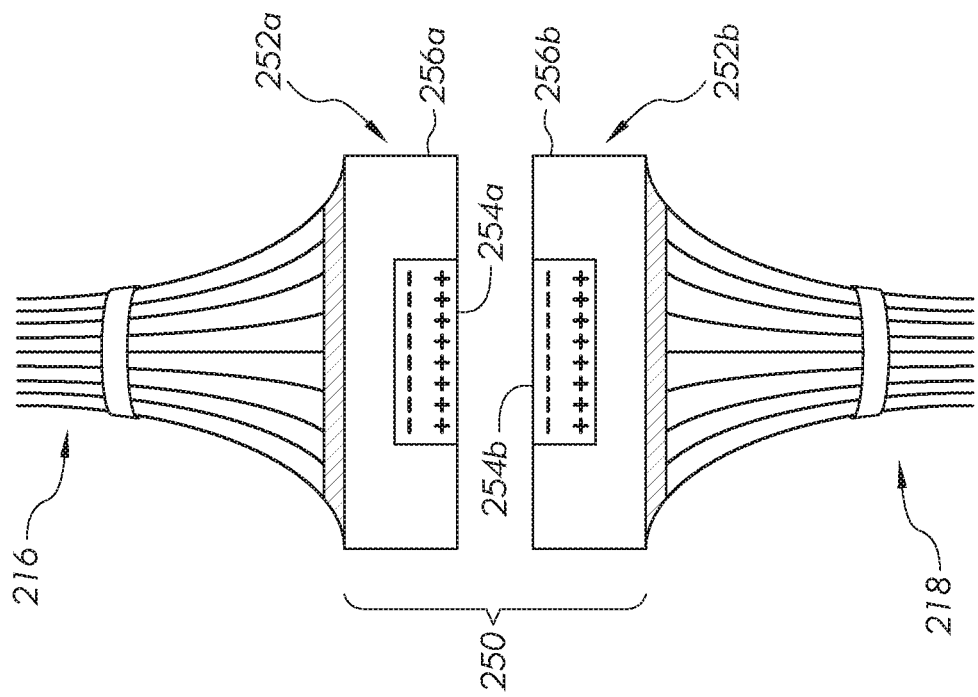
FIG. 7B schematically depicts a cross-section of a magnetic coupler in accordance with one or more embodiments described herein.

Referring now to FIG. 7B, another embodiment of a magnetic coupler 250 is schematically depicted. In this embodiment the magnetic coupler 250 includes a magnet 254a and a magnet 254b. The magnets 254a, 254b may be, for example and without limitation, ferrite magnets, rare earth magnets, sintered AlNiCo magnets, and the like. The magnets 254a, 254b are arranged such that the magnets 254a, 254b are mutually attracted, thereby coupling the magnet 254a and magnet 254b to one another and, hence, thermally coupling magnet 254a to magnet 254b. That is, the magnets 254a, 254b are arranged such that the "+" pole piece of either magnet 254a or magnet 254b mates with the "−" pole piece of the other of magnet 254a and 254b.

In this embodiment, the pigtail connector 216 may be thermally coupled to the magnet 254a with a thermally conductive adhesive to facilitate good thermal conduction between the thermally conductive material of the pigtail connector 216 and the magnet 254a. Alternatively, the pigtail connector 216 may be embedded in or fused to the magnet 254a to facilitate good thermal conduction between the thermally conductive material of the pigtail connector 216 and the magnet 254a.

In the embodiment of the magnetic coupler 250 depicted in FIG. 7B, the magnet 254b may optionally comprise a second pigtail connector 218. The second pigtail connector 218 may be used to couple the magnetic coupler to, for example, a cooling source (not depicted). The second pigtail connector 218 may be thermally coupled to the magnet 254b with a thermally conductive adhesive to facilitate good thermal conduction between the thermally conductive material of the second pigtail connector 218 and the magnet 254b. Alternatively, the second pigtail connector 218 may be embedded in or fused to the magnet 254b to facilitate good thermal conduction between the thermally conductive material of the second pigtail connector 218 and the magnet 254b.

Figure 7C:
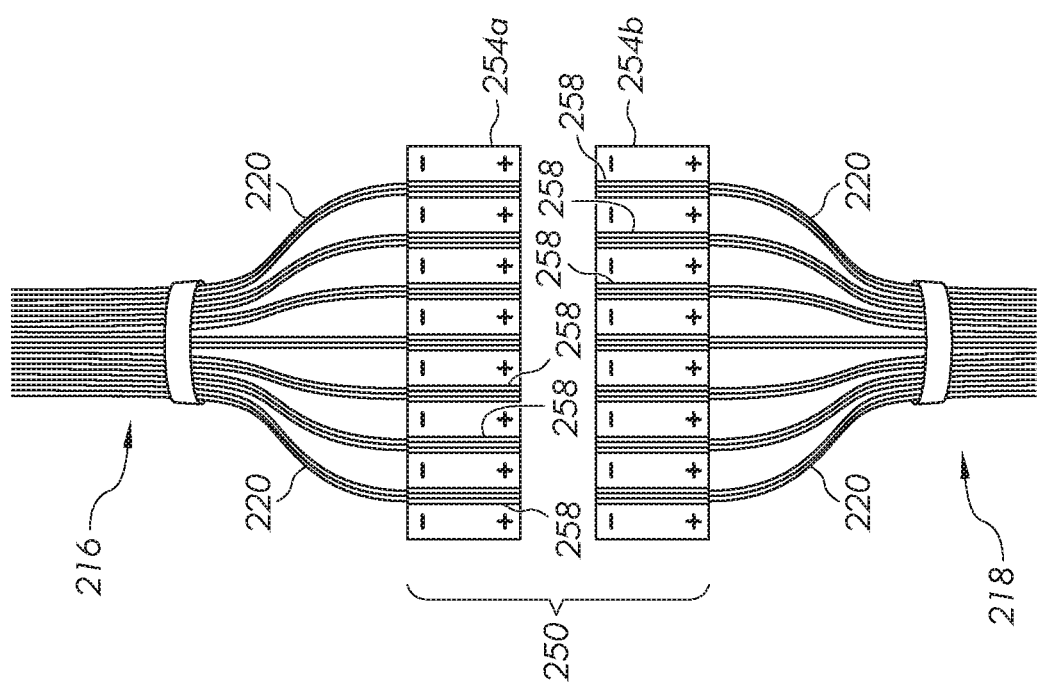
FIG. 7C schematically depicts a cross-section of a magnetic coupler in accordance with one or more embodiments described herein.

Referring now to FIG. 7C, another embodiment of a magnetic coupler 250 is schematically depicted. In this embodiment the magnetic coupler 250 includes a magnet 254a and a magnet 254b. The magnets 254a, 254b may be, for example and without limitation, ferrite magnets, rare earth magnets, sintered AlNiCo magnets, and the like. The magnets 254a, 254b are arranged such that the magnets 254a, 254b are mutually attracted, thereby coupling the magnet 254a and magnet 254b to one another and, hence, thermally coupling magnet 254a to magnet 254b. That is, the magnets 254a, 254b are arranged such that the "+" pole piece of either magnet 254a or magnet 254b mates with the "−" pole piece of the other of magnet 254a and 254b.

In this embodiment, the pigtail connector 216 may be mechanically connected to the magnet 254a. For example, the magnet 254a may include a plurality of channels 258 that extend through the thickness of the magnet 254a. Thermally conductive fibers 220 of the pigtail connector 216 may be positioned in the channels 258 such that the fibers extend through the thickness of the magnet 254a in the channels 258. The thermally conductive fibers 220 may be secured in the channels 258 with, for example, an adhesive, such as a thermally conductive adhesive.

In the embodiment of the magnetic coupler 250 depicted in FIG. 7C, the magnet 254b may further comprise a second pigtail connector 218. The second pigtail connector 218 may be used to couple the magnetic coupler to, for example, a cooling source (not depicted). The second pigtail connector 218 may be mechanically connected to the magnet 254b. For example, the magnet 254b may include a plurality of channels 258 that extend through the thickness of the magnet 254b. Thermally conductive fibers 220 of the second pigtail connector 218 may be positioned in the channels 258 such that the fibers extend through the thickness of the magnet 254b in the channels 258. The thermally conductive fibers 220 may be secured in the channels 258 with, for example, an adhesive, such as a thermally conductive adhesive.

Still referring to FIG. 7C, when the magnet 254a is mated with the magnet 254b, the thermally conductive fibers 220 of the pigtail connector 216 are directly thermally coupled to the fibers 220 of the second pigtail connector 218, thereby thermally coupling the pigtail connector 216 with the second pigtail connector 218.

The embodiments of the magnetic coupler 250 depicted in FIGS. 7A-7C may provide a relatively large surface area between opposing halves of the coupler which, in turn, aids in good thermal conduction through the magnetic coupler. In addition, the embodiments of the magnetic coupler provide a connection that may be easily separated and reconnected without the use of tools.

Figure 8:
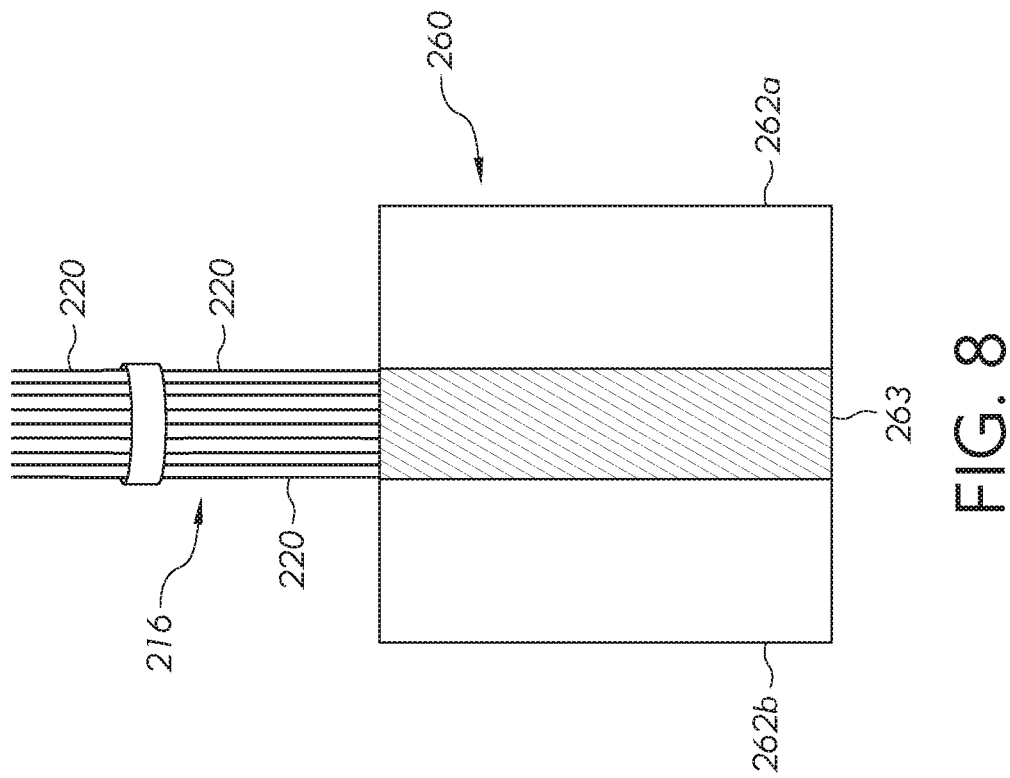
FIG. 8 schematically depicts a cross-section of a coupler in accordance with one or more embodiments described herein.

Referring now to FIG. 8, an alternative embodiment of a coupler 260 for thermally coupling the pigtail connector 216 to a cooling source is schematically depicted. In this embodiment, the coupler 260 includes a pair of platens 262a, 262b. The platens 262a, 262b may be formed from thermally conductive metals such as, without limitation, copper and copper alloys. In this embodiment, the thermally conductive fibers 220 of the pigtail connector 216 may be sandwiched between platen 262a and platen 262b such that the thermally conductive fibers 220 are thermally coupled to the respective surfaces of the platens 262a, 262b. In embodiments, the platens 262a, 262b, with the thermally conductive fibers 220 sandwiched therebetween, may be joined using, for example and without limitation, mechanical fasteners, adhesives including thermally conductive adhesives, solder, or the like. For example, in the embodiment of the coupler 260 depicted in FIG. 8, the platen 262a and 262b are joined together with a layer of adhesive 263. The thermally conductive platens 262a, 262b provide increased surface area by which heat conducted through the thermally conductive fibers 220 of the pigtail connector 216 may be diffused through conduction and/or convection.

While FIGS. 7A-7C and FIG. 8 depict various couplers for thermally coupling the pigtail connector 216 to, for example, a cooling source, it should be understood that other couplers are contemplated and possible. Moreover, it should be understood that, in some embodiments, the pigtail connector 216 may be thermally coupled to a cooling source without a coupler, such as when the thermally conductive fibers 220 of the pigtail connector 216 are proximity coupled to the cooling source or directly coupled to the cooling source.

As described herein, in embodiments, the thermally conductive core portion 200 (e.g., the thermally conductive core portions 200 depicted in FIGS. 5B-5F) of the support pads 130, or the thermally conductive element 308 (e.g., the thermally conductive element 308 depicted in FIG. 6) of the support pads 130, may be thermally coupled to a cooling source to further enhance the extraction of heat from the surface of the support pad. Various embodiments of cooling sources will now be described in detail with specific reference to the figures.

Figure 9:
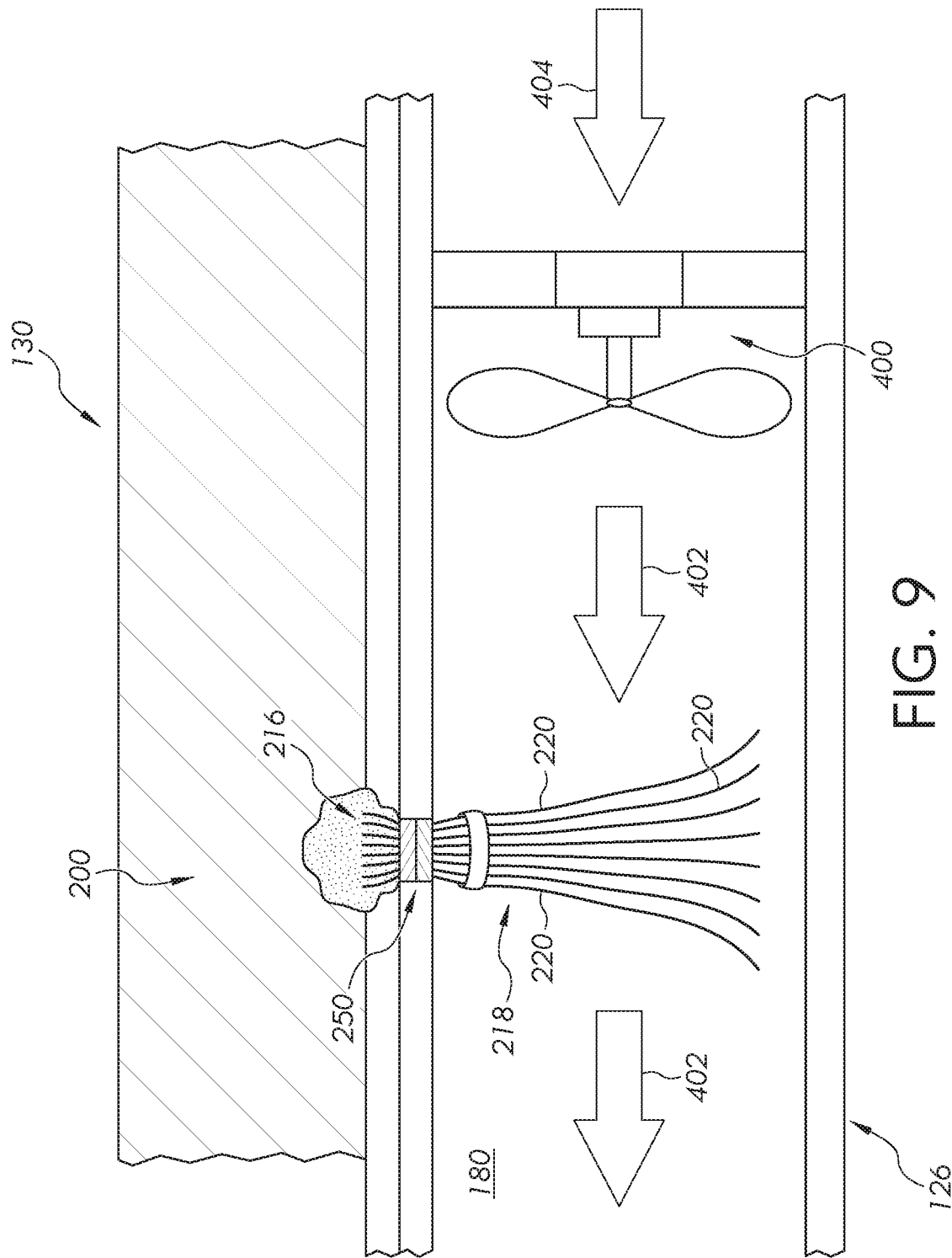
FIG. 9 schematically depicts a cross-section of a side rail with a cooling source thermally coupled to the support pad, in accordance with one or more embodiments shown and described herein.

Referring now to FIGS. 4A and 9, FIG. 9 schematically depicts one embodiment of a cross-section of the side rail 126 and support pad 130 of FIG. 4A in which the side rail 126 contains a cooling source. In this embodiment, the cooling source comprises a blower 400 disposed within the interior channel 180 of the side rail 126. While FIG. 9 schematically depicts the blower 400 as a conventional bladed fan, it should be understood that other blowers are contemplated and possible including without limitation, centrifugal blowers and the like. Further, while FIG. 9 depicts the blower positioned within the interior channel 180, it should be understood that other configurations are contemplated and possible, including configurations in which the blower 400 is located external to the side rail 126 and the output fluid 402 (e.g., air, schematically depicted with a block arrow) is coupled into the side rail 126 with a conduit.

In this embodiment, the support pad 130 includes a thermally conductive core portion 200 as depicted in FIG. 4A. However, it should be understood that, in an alternative embodiment, the thermally conductive core portion 200 may be similar to the thermally conductive core portion depicted in FIG. 4B. In this embodiment, the pigtail connector 216 of the support pad 130 is thermally coupled to a second pigtail connector 218 with magnetic coupler 250, such as the magnetic couplers depicted in FIGS. 7A-7C. In this embodiment, the portion of the magnetic coupler 250 thermally coupled to the second pigtail connector 218 is affixed in an aperture in the side rail 126 and the portion of the magnetic coupler 250 thermally coupled to the pigtail connector 216 may be removably positioned in the aperture to facilitate coupling and decoupling the thermally conductive core portion 200 (and hence the support pad 130) to and from the side rail 126.

In the embodiment depicted in FIG. 9, the thermally conductive fibers 220 of the second pigtail connector 218 are loosely bundled and suspended within the interior channel 180 to facilitate the circulation of output fluid 402 from the blower 400 around and through the thermally conductive fibers 220. In this regard, the thermally conductive fibers 220 are thermally coupled to a cooling source, specifically the blower 400, with the output fluid 402 directed through the side rail 126. Specifically, the blower 400 draws in feed fluid 404 (e.g., air, schematically depicted by a block arrow) and outputs output fluid 402 to create a flow of fluid through the side rail 126. As the output fluid 402 passes around and through the thermally conductive fibers 220, heat conducted from the thermally conductive core portion 200 through the pigtail connector 216 and magnetic coupler 250 to the second pigtail connector 218 is dissipated into the interior channel 180 of the side rail 126 by forced convection, thereby cooling at least a portion of the support pad 130.

While the feed fluid 404 and the output fluid 402 are described as air in the embodiment depicted in FIG. 9, it should be understood that other fluids are possible and contemplated. For example, in some embodiments the feed fluid 404 may be, for example, an inert gas, such as nitrogen. Alternatively, the feed fluid 404 may be a combination of gases. In embodiments, the temperature of the feed fluid 404 may be reduced by conditioning to increase convection and hence, increase the extraction of heat from the support pad 130. In such embodiments, the temperature of the feed fluid 404 may be conditioned by passing the input fluid over or through dry ice such that the feed fluid 404 is a mixture of, for example, atmospheric air and $CO_2$ or nitrogen and $CO_2$. As another example, the feed fluid 404 may be conditioned by injecting liquid nitrogen into the feed fluid 404 such that the feed fluid 404 is a mixture of, for example, atmospheric air and $N_2$ vapor or nitrogen and $N_2$ vapor.

In still other embodiments, the temperature of the input air may be increased to reduce convection and, hence, reduce the extraction of heat from the support pad 130. For example, in embodiments, the feed fluid 404 may be passed over or through a heater, such as an electrical resistance heater or the like, which increases the temperature of the feed fluid 404 and reduces the convection of heat from the thermally conductive fibers 220.

In still other embodiments, the convection of heat from the thermally conductive fibers 220 may be controlled by controlling the volume of output fluid 402 flowing through the interior channel 180 of the side rail 126. For example, when more heat extraction from the thermally conductive fibers is desired (i.e., when more cooling of the support pad 130 is desired), the volume of output fluid 402 directed through the interior channel 180 of the side rail 126 may be increased, by, for example, increasing the rotational velocity of the blower 400. Conversely, when less heat extraction from the thermally conductive fibers is desired (i.e., when less cooling of the support pad 130 is desired), the volume of output fluid 402 directed through the interior channel 180 of the side rail 126 may be decreased, by, for example, decreasing the rotational velocity of the blower 400.

While FIG. 9 schematically depicts the thermally conductive fibers 220 being loosely bundled and suspended in the interior channel 180, it should be understood that other embodiments are contemplated and possible. For example, in embodiments, the thermally conductive fibers 220 may be thermally coupled to the output fluid 402 from the blower 400 using a coupler as depicted in FIG. 8. In this embodiment, the coupler provides increased surface area over which the output fluid 402 may be directed to facilitate forced convection of heat from the thermally conductive fibers 220.

While the feed fluid 404 has been described herein as being a gas directed through the interior channel 180 of the side rail 126, it should be understood that other embodiments are contemplated and possible. For example, in an alternative embodiment, the feed fluid may be a liquid, such as water, liquid nitrogen, or a coolant, directed through the interior channel 180 of the side rail 126 with a pump rather than a blower.

While FIG. 9 schematically depicts a support pad 130 with a thermally conductive core portion 200 as depicted in FIG. 4A, it should be understood that other configurations of the support pad 130 are also contemplated and possible including, without limitation, the configuration of the support pad 130 depicted in FIG. 6.

Figure 10:
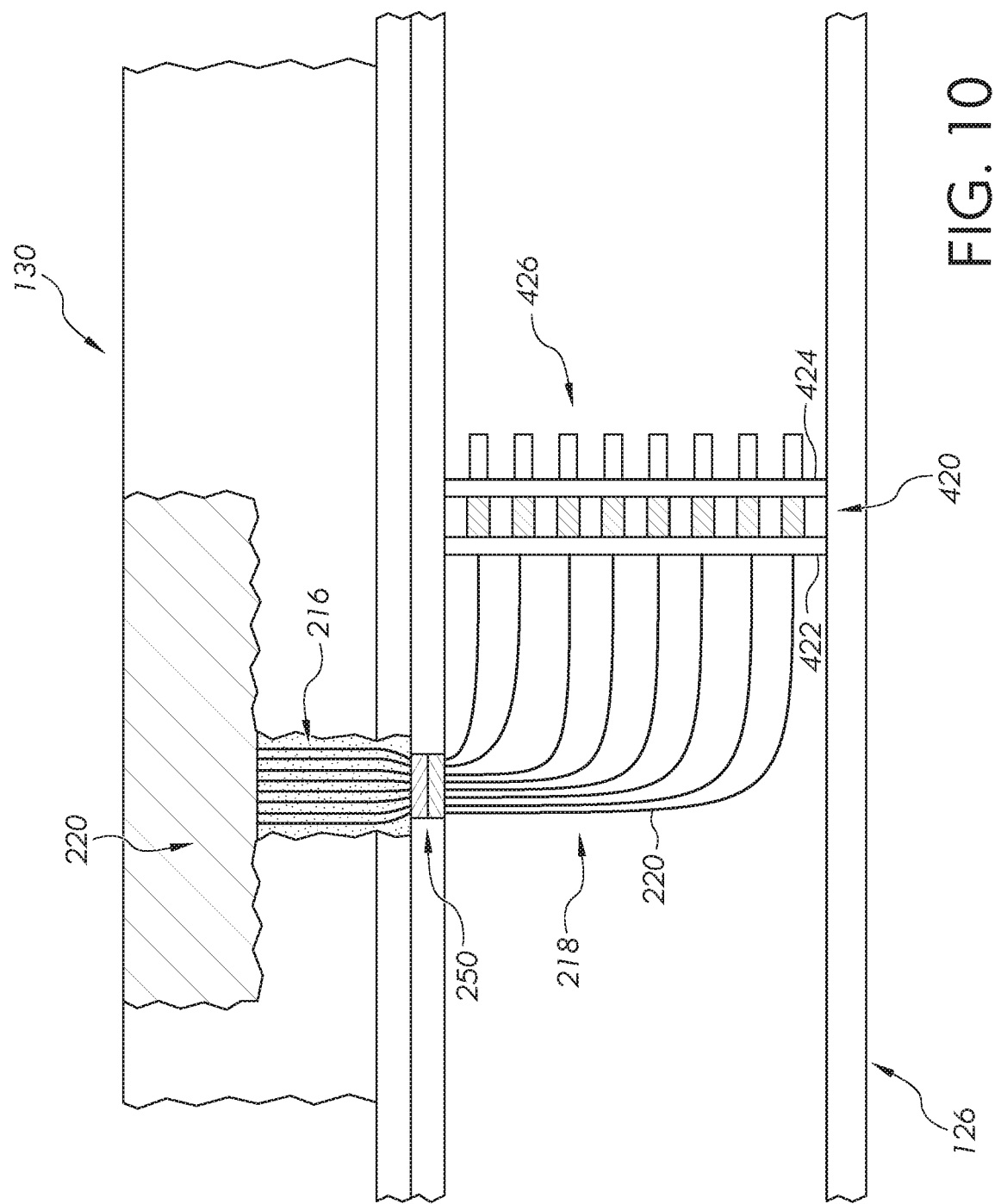
FIG. 10 schematically depicts a cross-section of a side rail with a cooling source thermally coupled to the support pad, in accordance with one or more embodiments shown and described herein.

Referring now to FIGS. 4B and 10, FIG. 10 schematically depicts one embodiment of a cross-section of the side rail 126 and the support pad 130 of FIG. 4B in which the side rail 126 contains a cooling source. In this embodiment, the cooling source comprises a thermoelectric cooler 420, such as a Peltier cooler, disposed within the interior channel 180 of the side rail 126. While FIG. 9 depicts the thermoelectric cooler 420 positioned within the interior channel 180, it should be understood that other configurations are contemplated and possible, including configurations in which the thermoelectric cooler 420 is located external to the side rail 126, such as when the thermoelectric cooler 420 is mounted external to the side rail 126, such as at an opening of the interior channel 180 at an end of the side rail 126. Alternatively, the thermoelectric cooler 420 may be positioned within the support pad 130, specifically in areas of the support pad 130 outside of the thermally conductive core portion 200 and/or where radiolucency of the support pad 130 is not a consideration.

In this embodiment, the support pad 130 includes a thermally conductive core portion 200 as depicted in FIG. 4B. However, it should be understood that, in an alternative embodiment, the thermally conductive core portion 200 may be similar to the thermally conductive core portion depicted in FIG. 4A. In this embodiment, the pigtail connector 216 of the support pad 130 is thermally coupled to a second pigtail connector 218 with a magnetic coupler 250, such as the magnetic couplers depicted in FIGS. 7A-7C. In this embodiment, the portion of the magnetic coupler 250 thermally coupled to the second pigtail connector 218 is affixed in an aperture in the side rail 126 and the portion of the magnetic coupler 250 thermally coupled to the pigtail connector 216 may be removably positioned in the aperture to facilitate coupling and decoupling the thermally conductive core portion 200 (and hence the support pad 130) from the side rail 126.

In the embodiment depicted in FIG. 10, the thermally conductive fibers 220 of the second pigtail connector 218 are loosely bundled and directly coupled across the surface of the cooling plate 422 of the thermoelectric cooler 420 to facilitate conducting heat through the thermally conductive fibers 220 of the second pigtail connector 218. In this regard, the thermally conductive fibers 220 of the second pigtail connector 218 are thermally coupled to a cooling source, specifically the cooling plate 422 of the thermoelectric cooler 420. Specifically, when the thermoelectric cooler 420 is powered on, a temperature differential is created between the cooling plate 422 and the heating plate 424 of the thermoelectric cooler 420 resulting in heat input into the cooling plate 422 being pumped to the heating plate 424 where it may be dissipated. For example, in some embodiments, the heating plate 424 of the thermoelectric cooler 420 includes cooling fins 426 to aid in the dissipation of heat from the heating plate 424. The heat may be dissipated by, for example, radiation or a combination of radiation and convection, such as when a fan or blower is used to direct heat over the cooling fins 426. Accordingly, it should be understood that, in some embodiments, the thermoelectric cooler 420 may further include a fan or blower (not depicted) to assist with the dissipation of heat from the heating plate 424.

While FIG. 10 schematically depicts the thermally conductive fibers 220 of the second pigtail connector 218 directly coupled to the cooling plate 422 of the thermoelectric cooler 420, it should be understood that other embodiments are contemplated and possible. For example, a magnetic coupler, similar to the magnetic couplers depicted in FIGS. 7A-7C, may be utilized to couple the second pigtail connector 218 to the cooling plate 422 of the thermoelectric cooler 420. Alternatively, a coupler 260 as depicted in FIG. 8 may be utilized to couple the second pigtail connector 218 to the cooling plate 422 of the thermoelectric cooler 420. In this embodiment, the second pigtail connector 218 may be sandwiched between the platens 262a, 262b of the coupler 260 and one of the platens 262a, 262b may be attached to the cooling plate 422 of the thermoelectric cooler 420.

In operation, heat conducted from the thermally conductive core portion 200 of the support pad 130 is conducted through the pigtail connector 216 and magnetic coupler 250 to the second pigtail connector 218. This heat is then conducted through the thermally conductive fibers of the second pigtail connector 218 into the cooling plate 422 of the thermoelectric cooler and pumped to the heating plate 424 of the thermoelectric cooler 420 and, thereafter, dissipated. The flow of heat from the thermally conductive core portion 200 of the support pad 130 to the heating plate 424 of the thermoelectric cooler 420 results in cooling of at least a portion of the support pad 130.

In the embodiment depicted in FIG. 10, the amount of heat extracted from the support pad 130 may be controlled by, for example, adjusting the input voltage and/or current into the thermoelectric cooler 420.

While FIG. 10 schematically depicts a support pad 130 with a thermally conductive core portion 200 as depicted in FIG. 4B, it should be understood that other configurations of the support pad 130 are also contemplated and possible including, without limitation, the configuration of the support pad 130 depicted in FIG. 6.

Figure 11:
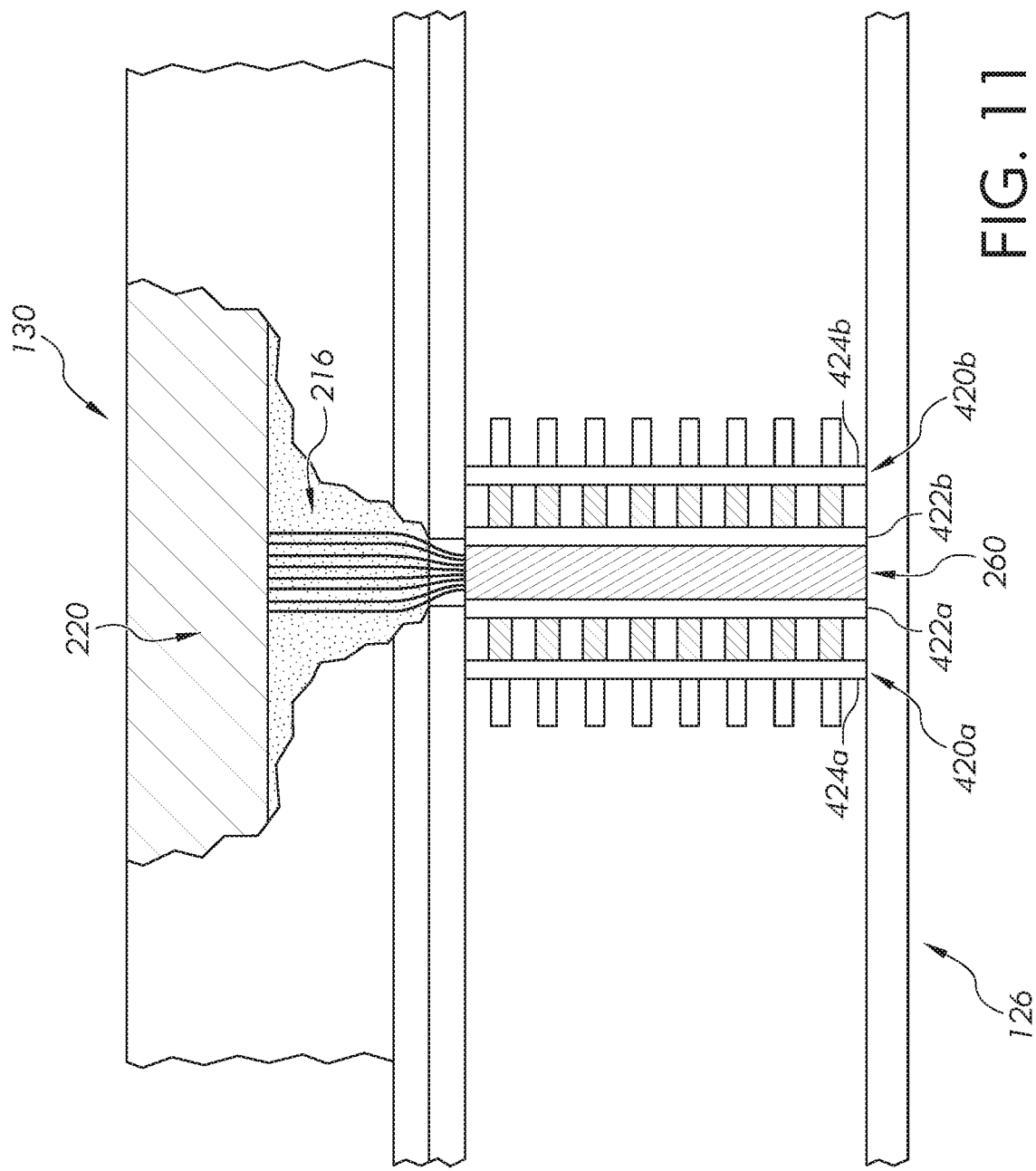
FIG. 11 schematically depicts a cross-section of a side rail with a cooling source thermally coupled to the support pad, in accordance with one or more embodiments shown and described herein.

Further, while FIG. 10 depicts a single thermoelectric cooler 420, it should be understood that other embodiments are contemplated and possible. Referring to FIG. 11 and FIG. 8 by way of example, FIG. 11 schematically depicts one embodiment of a cross-section of the side rail 126 and support pad 130 similar to FIG. 10. However, in this embodiment, the side rail 126 includes a first thermoelectric cooler 420a and second thermoelectric cooler 420b disposed within the interior channel 180 of the side rail 126. In this embodiment, the pigtail connector 216 of the support pad 130 is thermally coupled to the first thermoelectric cooler 420a and the second thermoelectric cooler 420b with a coupler 260, such as the coupler 260 depicted in FIG. 8. Specifically, the thermally conductive fibers (not depicted) of the pigtail connector 216 are sandwiched between the platens 262a, 262b of the coupler 260, as depicted in FIG. 8, and the platens, 262a, 262b are, in turn, thermally coupled to the cooling plates 422a, 422b of the first thermoelectric cooler 420a and the second thermoelectric cooler 420b, respectively.

In operation, heat conducted from the thermally conductive core portion 200 of the support pad 130 is conducted through the pigtail connector 216 and to the platens 262a, 262b of the coupler 260. The heat is then conducted through the platens 262a, 262b of the coupler 260 and into the cooling plates 422a, 422b of the first thermoelectric cooler 420a and the second thermoelectric cooler 420b, respectively. The heat is then and pumped to the heating plates 424a, 424b of the first thermoelectric cooler 420a and the second thermoelectric cooler 420b, respectively and, thereafter, dissipated. The flow of heat from the thermally conductive core portion 200 of the support pad 130 to the heating plates 424a, 424b of the first thermoelectric cooler 420a and the second thermoelectric cooler 420b results in cooling of at least a portion of the support pad 130. Moreover, use of multiple thermoelectric coolers 420a, 420b increases the amount of heat that can be extracted from the thermally conductive core portion 200 and, thus, the amount of cooling provided by the support pad 130.

While FIG. 11 schematically depicts a support pad 130 with a thermally conductive core portion 200 as depicted in FIG. 4B, it should be understood that other configurations of the support pad 130 are also contemplated and possible including, without limitation, the configuration of the support pad 130 depicted in FIG. 6.

Figure 12:
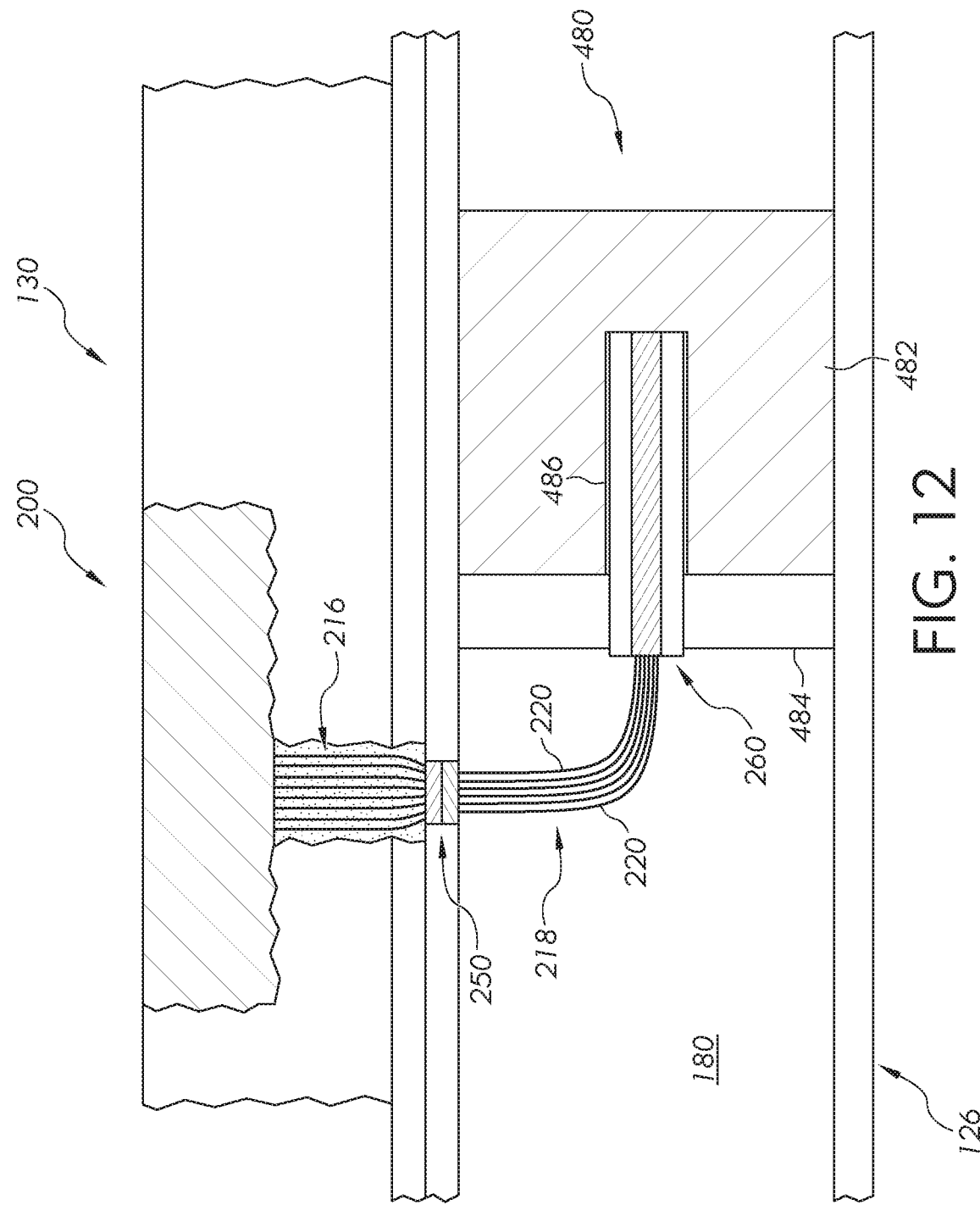
FIG. 12 schematically depicts a cross-section of a side rail with a cooling source thermally coupled to the support pad, in accordance with one or more embodiments shown and described herein.

Referring now to FIGS. 4B and 12, FIG. 12 schematically depicts one embodiment of a cross-section of the side rail 126 and support pad 130 of FIG. 4B in which the side rail 126 contains a cooling source. In this embodiment, the cooling source comprises a canister 480 containing thermally absorptive material 482. The canister 480 is disposed within the interior channel 180 of the side rail 126. In the embodiment depicted in FIG. 12, the canister 480 may be constructed from a thermally conductive metal, such as, without limitation, copper or a copper alloy. The thermally absorptive material 482 contained in the canister 480 may include, without limitation, phase change materials, oils having relatively high heat capacities, dry ice, water ice, liquid nitrogen or the like. Suitable phase change materials include, without limitation, alkanes having a melting temperature greater than or equal to about 5° C. and less than or equal to about 35° C. Examples of suitable alkanes include, without limitation, tetradecane, pentadecane, hexadecane, heptadecane, octadecane, and nonadecane. Suitable high heat capacity oils include, without limitation, mineral oils, silicon oils, fluorocarbon oils, and the like. In embodiments, the canister 480 may be formed with a canister coupler 486 to enable the canister 480 and, more specifically, the thermally absorptive material 482 within the canister 480, to be thermally coupled to the thermally conductive core portion 200 of the support pad 130. In embodiments, the canister coupler 486 may be, for example, a slot configured to receive a corresponding connector, such as coupler 260 depicted in FIG. 8.

While FIG. 12 depicts the canister 480 as being located within the side rail 126, it should be understood that other embodiments are contemplated and possible, such as embodiments where the canister 480 is mounted external to the side rail 126.

In the embodiment depicted in FIG. 12, the support pad 130 includes a thermally conductive core portion 200 as depicted in FIG. 4B. However, it should be understood that, in an alternative embodiment, the thermally conductive core portion 200 may be similar to the thermally conductive core portion depicted in FIG. 4A. In this embodiment, the pigtail connector 216 of the support pad 130 is thermally coupled to a second pigtail connector 218 with magnetic coupler 250, such as the magnetic couplers depicted in FIGS. 7A-7C. In this embodiment, the portion of the magnetic coupler 250 thermally coupled to the second pigtail connector 218 is affixed in an aperture in the side rail 126 and the portion of the magnetic coupler 250 thermally coupled to the pigtail connector 216 may be removably positioned in the aperture to facilitate coupling and decoupling the thermally conductive core portion 200 (and hence the support pad 130) from the side rail 126.

A coupler 260, such as the coupler 260 depicted in FIG. 8, may be utilized to couple the second pigtail connector 218 to the canister coupler 486 of the canister 480. Specifically, the second pigtail connector 218 may be sandwiched between the platens 262a, 262b of the coupler 260. The coupler 260 is, itself, mechanically coupled to a bracket 484 disposed in the interior channel 180 of the side rail 126. The canister 480 may be removably coupled to the coupler 260 by positioning the canister 480 in the interior channel 180 of the side rail such that the canister coupler 486 is engaged with the coupler 260 positioned in the side rail 126.

In operation, heat conducted from the thermally conductive core portion 200 of the support pad 130 is conducted through the pigtail connector 216 and magnetic coupler 250 to the second pigtail connector 218. This heat is then conducted through the thermally conductive fibers of the second pigtail connector 218 into the platens 262a, 262b (FIG. 8) of the coupler 260. The heat is conducted from the platens 262a, 262b of the coupler 260 into the thermally absorptive material 482 of the canister 480 where it is absorbed. The flow of heat from the thermally conductive core portion 200 of the support pad 130 to the thermally absorptive material 482 of the canister results in cooling of at least a portion of the support pad 130.

In embodiments, heat conduction from the support pad 130 to the thermally absorptive material 482 may continue until the heat capacity of the thermally absorptive material 482 is reached and/or an equilibrium temperature is reached between the thermally absorptive material 482 and the support pad 130, more specifically, a subject positioned on the support pad 130. When this occurs, and further cooling is desired, the canister 480 may be removed and replaced with a fresh canister of thermally absorptive material to continue the conduction of heat from the support pad 130.

While FIG. 12 schematically depicts a support pad 130 with a thermally conductive core portion 200 as depicted in FIG. 4B, it should be understood that other configurations of the support pad 130 are also contemplated and possible including, without limitation, the configuration of the support pad 130 depicted in FIG. 6.

Figure 13:
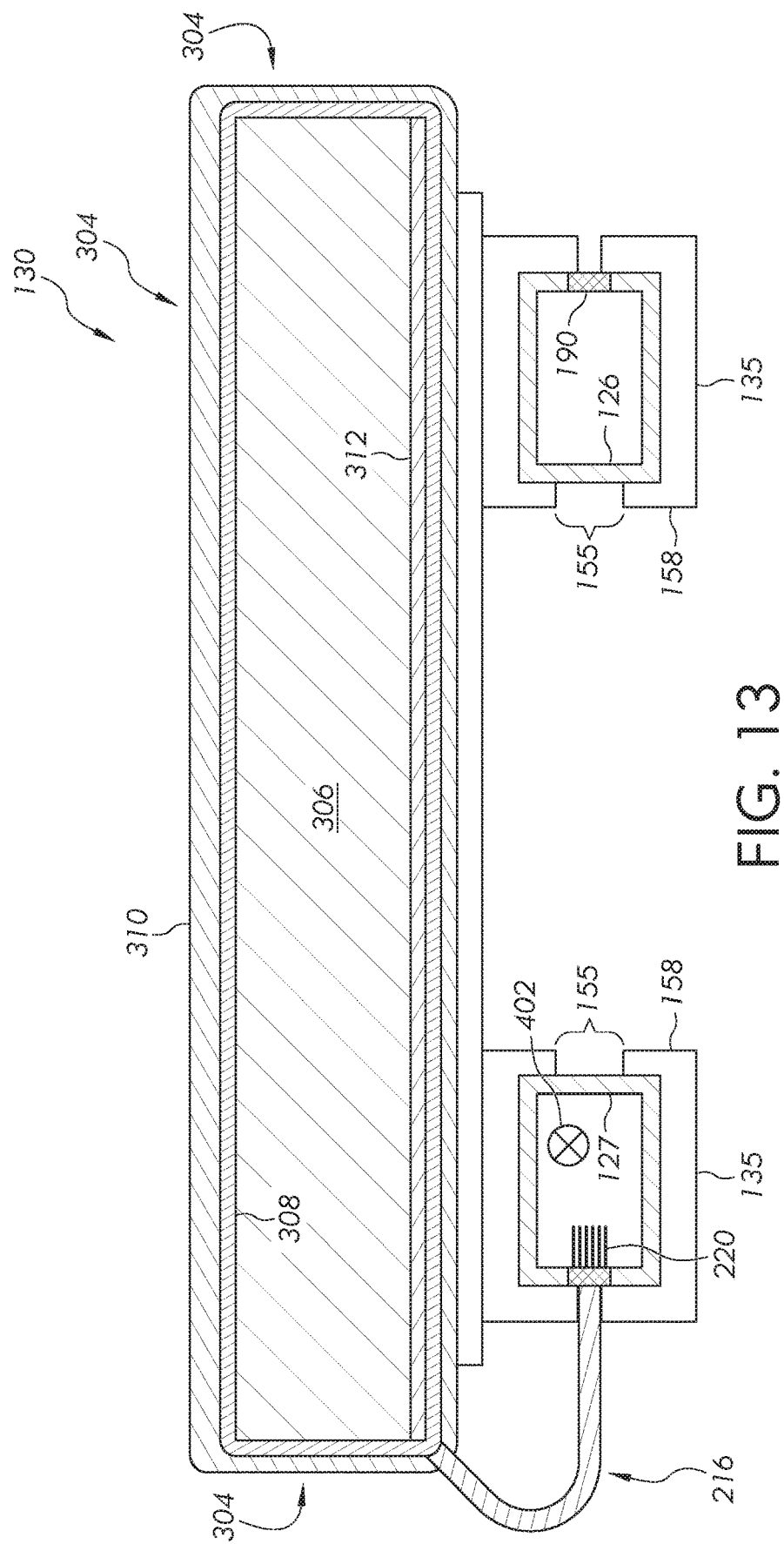
FIG. 13 schematically depicts a cross-section of one of the support pads of the person support system of FIG. 1 along the line A-A in accordance with one or more embodiments described herein.

Referring again to FIGS. 1, 2, 6, and 13 in some embodiments, the support pad 130 of FIG. 6 may be coupled to the longitudinal frame 125 with one or more clamps 135. In some embodiments, each support pad 130 may be coupled to the longitudinal frame 125 via a plurality of clamps. More particularly, FIG. 13 depicts a cross-section along the line A-A of FIG. 1. As shown in FIG. 13, the support pad 130 includes a clamp 135 that is coupled to the first side rail 126 and a clamp 135 that is coupled to the second side rail 127. The clamps 135 may be coupled such that they are slidably movable along a length of the respective side rails 126, 127. Accordingly, it should be understood that the clamps 135 (and the support pad 130 coupled thereto) are repositionable along the length of the longitudinal frame 125. In addition, the clamps 135 may be coupled to respective side rails 126, 127 such that the clamps 135 retain the support pad 130 on the respective side rails 126, 127. In some embodiments, the clamps 135 may be spaced in pairs such that a clamp 135 is positioned in a first location on the first side rail 126 and a second clamp 135 is positioned in a second location on the second side rail 127, where the first and second locations are parallel and opposing each other at an equal distance from the head column 122 and the foot column 124. In some embodiments, the clamps 135 may be positioned at a location on the respective side rail 126, 127 that contains a quick disconnect slot 190 such that each of the clamps 135 are engaged and/or aligned with a corresponding quick disconnect slot 190.

The clamps 135 are coupled to the respective side rails 126, 127 via one or more clamping features. For example, as shown in FIG. 13, the clamp 135 may be a "C" shaped clamp having an opening 155 and one or more lips 158 that extend towards the opening 155 in the "C" shape. As such, the clamp 135 receives the side rail 126, 127 by allowing the side rail 126, 127 to pass through the opening 155. In addition, once the clamp 135 is arranged around the side rail 126, 127, the one or more lips 158 prevent the clamp 135 from slipping off of the side rail 126, 127. In this embodiment, the clamps may be formed from a material which is elastically deformable and recoverable, such as a polymeric material or the like, to facilitate attaching the clamp to a respective side rail.

Alternatively, the clamp 135 may have a first clamp portion and a second clamp portion that is separate from the first clamp portion. In such embodiments, the first clamp portion may be attachable to the second clamp portion with the side rail 126, 127 enclosed within the clamp 135. The first clamp portion may be secured to the second clamp portion via one or more attachment devices, such as threaded fasteners, clips or the like. In other embodiments, the first clamp portion may be partially attached to the second clamp portion via a clamp hinge such that the first clamp portion and the second clamp portion can be brought together around the side rail by rotating the second clamp portion about a clamp hinge from an open position to a closed position. In some embodiments, the first clamp portion may be further secured to the second clamp portion via one or more attachment devices including, without limitation, threaded fasteners, clips, latches or the like.

Still referring to FIG. 13, the longitudinal frame 125, particularly the first side rail 126 and the second side rail 127, may each include one or more quick disconnect slots 190. In some embodiments, a plurality of the quick disconnect slots 190 may be spaced at particular locations along the length of each side rail 126, 127. In some embodiments, the quick disconnect slots 190 may be spaced in pairs such that a first quick disconnect slot 190 is positioned in a first location on the first side rail 126 and a second quick disconnect slot 190 is positioned in a second location on the second side rail 127, where the first and second locations are parallel and opposing each other at an equal distance from the head column 122 and the foot column 124.

The quick disconnect slots 190 facilitate inserting the pigtail connector 216 of the support pad 130 into the side rail 126, 127 such that a cooling fluid may be directed over and through the thermally conductive fibers 220 of the pigtail connector 216, in a similar manner as depicted and described herein with respect to FIG. 9, thereby dissipating heat from the thermally conductive element 308 of the support pad 130. For example, in various embodiments, in addition to the removal of heat from the person support surface 310 via convection through the thermally conductive element 308, heat may be dissipated from the person support surface 310 by conducting the heat through the pigtail connector 216 into the side rail 127 where a cooling fluid (i.e., output fluid 402), such as a gas or the like, is directed around and through the thermally conductive fibers 220 of the pigtail connector 216. In such embodiments, the conduction may be coupled with convection enhance the removal of heat from the source region such as when the thermally conductive element 308 is thermally coupled to a cooling fluid. For example, as shown in FIG. 13, the thermally conductive element 308 is coupled to the side rail 127 of the longitudinal frame 125 via the quick disconnect slot 190 and the pigtail connector 216. More particularly, the pigtail connector 216 from the thermally conductive element 308 may be threaded through a slot in the clamp 135 and through the quick disconnect slot 190 such that the thermally conductive fibers 220 of the pigtail connector 216 are in communication with the inside of the side rail 127 and, more particularly, with a cooling fluid flowing through the side rail 127.

In embodiments in which conduction is used in conjunction with convection to dissipate heat from the support pad 130, the thermally conductive element 308 draws heat away from the source region and directs the heat into one or both of the side rails 126, 127 with one or more pigtail connectors 216. The side rails 126, 127 are coupled to a cooling source 140 (shown in FIG. 1) that provides a cooling fluid to the side rails 126, 127. The cooling source 140 may include, by way of example and not limitation, a pump or fan to direct cooling fluid through the side rails 126, 127, as shown and described herein with respect to FIG. 9. The cooling fluid absorbs the heat from the thermally conductive fibers 220 of the pigtail connector 216 and carries the heat through the side rails 126, 127, away from the person support surface 310, where it may be dissipated in a heat exchanger and/or exhausted to the environment. In some embodiments, the cooling source 140 may provide the cooling fluid directly through the side rails 126, 127, although in other embodiments, the cooling fluid may be contained within a conduit, such as a tube or pipe running through the side rails 126, 127. A conduit may enable the quick disconnect slots 190 to provide cooling features in addition to one or more of electrical lines, pneumatic lines, and/or hydraulic lines via the longitudinal frame 125.

The cooling fluid may be any suitable gas or liquid, as described herein with respect to FIG. 9. For example and without limitation, in various embodiments, the cooling fluid may be air, water, or another fluid composition that has high thermal capacity. According to various embodiments, the cooling fluid is pumped into the side rail 126, 127 at a temperature from about 15.5° C. to about 32° C. The temperature of the cooling fluid may vary depending on the particular embodiment. For example, the temperature of the cooling fluid may be adjusted to achieve a particular temperature at the person support surface 310 of the support pad 130. As a result of the cooling fluid, the removal of heat from the thermally conductive element 308 may be enhanced, which in turn may increase the temperature gradient between the source region and the sink region and further enhance cooling of the person support surface 310 of the support pad 130.

Still referring to FIG. 13, when a subject is supported on the person support surface 310, the thermally conductive element 308 draws the heat from the person support surface 310 and directs the heat (via conduction) to the edges of the support pad 130. In the embodiment depicted in FIG. 13, the heat may be directed through the thermally conductive element 308 around the edges of the support pad 130. The pigtail connector 216 may conduct the heat from the thermally conductive element 308 through the slots in the clamps 135, and into the quick disconnect slots 190 positioned in the side rails 126, 127. Cooling fluid passing through the side rails 126, 127 then removes the heat via convection through the side rails 126, 127 and out to the environment or through an exhaust (not shown).

Figure 14:
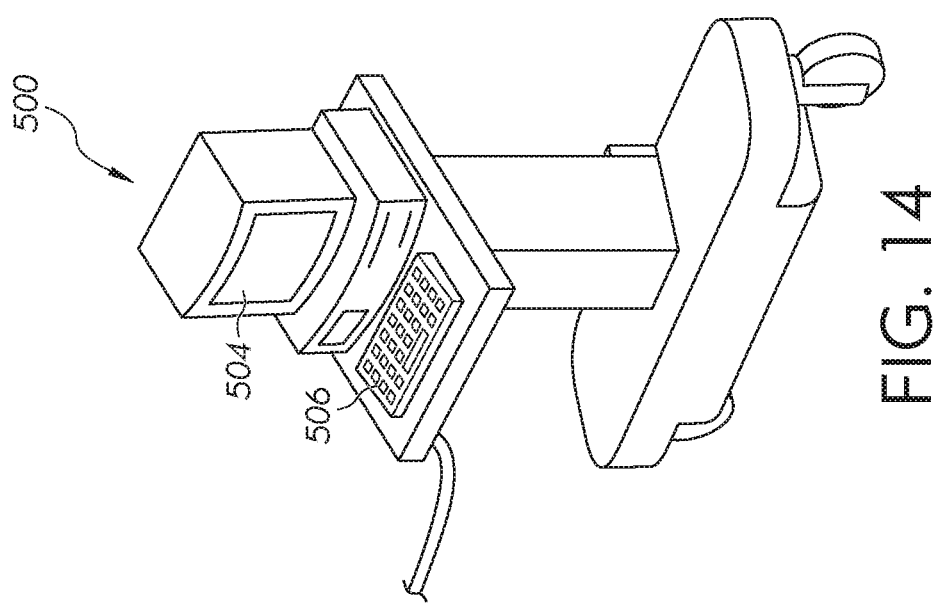
FIG. 14 schematically depicts a control unit of a person support system in accordance with one or more embodiments described herein.
Figure 15:
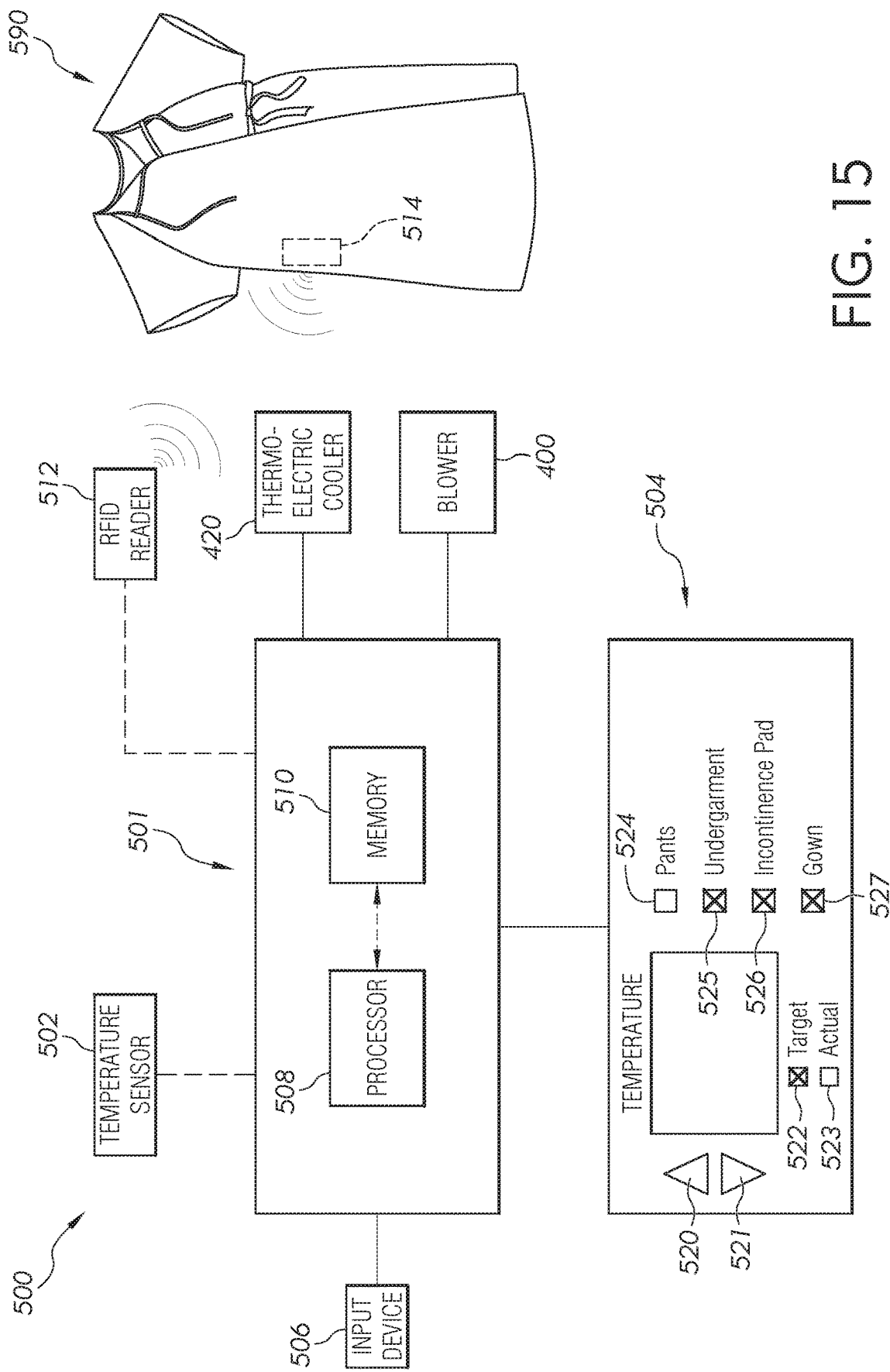
FIG. 15 schematically depicts the interconnectivity of various components of the control unit of a person support system in accordance with one or more embodiments.

Referring now to FIGS. 1, 3, 14 and 15, in some embodiments described herein, the person support system 100, 101 may further include a control unit 500. FIG. 14 schematically depicts one embodiment of a control unit 500 and FIG. 15 schematically depicts the interconnectivity of various parts of the control unit 500 as well as components communicatively coupled to the control unit 500. In embodiments, the control unit 500 may be used to achieve a desired amount of cooling with a support pad comprising a thermally conductive core portion, including, without limitation, when the thermally conductive core portion is thermally coupled to a cooling source, as described with respect to FIGS. 9, 10, 11, and 13. However, it should be understood that the control unit 500 may also be used to assist in achieving a desired amount of cooling with support pads having thermally conductive core portions which are not thermally coupled to a cooling source.

The control unit 500 may be, by way of example and not limitation, a computing device that includes a microcontroller 501 communicatively coupled to a display device 504. The microcontroller 501 may include a processor 508 that is communicatively coupled to a non-transitory memory 510 storing computer-readable and executable instructions, which, when executed by the processor, facilitate cooling of a thermally conductive core portion of a support pad 130 of the person support system 100, 101. That is, in embodiments, when the computer-readable and executable instructions are executed by the processor 508, the control unit 500 regulates the temperature of at least a portion of the top surface of a support pad 130 of the person support system 100, 101. In some embodiments, the control unit 500 may enable user, such as a caregiver, to manually adjust the cooling of the support pad 130, as will be described further herein.

In embodiments, the control unit 500 may include a temperature sensor 502 communicatively coupled to the microcontroller 501. The temperature sensor 502 outputs a signal (i.e., a temperature signal) indicative of the temperature of an object on which it is positioned. In embodiments, the temperature sensor 502 may be communicatively coupled to the microcontroller 501 with wires or, alternatively, wirelessly, such as when the temperature sensor 502 includes an RF transmitter (or transceiver) for transmitting the temperature signal from the temperature sensor 502 and the microcontroller 501 includes an RF receiver (or transceiver) for receiving the temperature signal from the temperature sensor 502.

In embodiments, the temperature sensor 502 may be positioned on the surface of a support pad 130 in an area corresponding to an area of a subject (e.g., the sacral area, the scapular areas, buttocks, heels or the like) to be cooled when the subject is positioned on the support pad 130. The temperature sensor 502 may be positioned to detect either the temperature of the skin of the subject or the temperature of the surface of the support pad 130, which may be similar to the temperature of the skin of the subject. Alternatively, the temperature sensor 502 may be embedded in the person support pad 130, such as in a thermally conductive core portion of the support pad 130, such that the temperature sensor 502 is positioned to detect a temperature of the thermally conductive core portion. In still other embodiments, the temperature sensor 502 may be positioned directly on the skin of the subject, such as in the sacral area, scapular area, buttocks, heels or the like, and held in place with, for example, adhesive or a dressing. In yet other embodiments, the temperature sensor 502 may be positioned in a garment worn by the subject, such as a hospital gown, undergarment, pants, or the like. In embodiments, the temperature signal provided by the temperature sensor 502 to the microcontroller 501 may be used, for example and without limitation, to control the cooling provided by the thermally conductive core portions of the support pad 130, determine proper positioning of the subject with respect to the thermally conductive core portions of the support pad 130, determine if a cooling device is functioning properly and/or providing sufficient cooling, determine if a thermally conductive core portion should be replaced to provide better cooling, and/or combinations thereof.

Still referring to FIGS. 1, 3, 14, and 15, in embodiments, the control unit 500 may optionally include an RFID reader 512 communicatively coupled to the microcontroller 501. In embodiments, the RFID reader 512 may be used to identify various accessories associated with the person support system 100, 101 and/or a subject positioned on the person support system 100, 101, which accessories may influence the cooling of the subject with the support pad(s) 130 of the person support system 100, 101. In embodiments, the RFID reader 512 outputs a signal (i.e., an accessory identification signal) indicative of an identity of an accessory being used in conjunction with the person support system 100, 101. For example, in embodiments, a sheet, pillow, or blanket (i.e., linens) being used on the person support system 100, 101 may include an RFID tag 514 encoded with the identity of the sheet or blanket. Similarly, garments (e.g., the gown, pants, shirt, undergarment, socks, dressings, patches (i.e., a sacral patch) or the like) worn by the patient may include an RFID tag 514 encoded with the identity of the garment. As another example, any pads or cushions, such as incontinence pads or the like, used in conjunction with the support pads 130 of the person support system 100, 101 and/or a subject positioned on the support pads 130, may include an RFID tag 514 encoded with the identity of the pad or cushion. In the specific example, depicted in FIG. 15, the accessory 590 is a hospital gown which includes an RFID tag 514 encoded with the identity of the hospital gown. The RFID reader detects the accessory 590 with RFID tag 514, interrogates the RFID tag 514, and outputs an accessory identification signal which, in this embodiment, indicates that the accessory 590 is a hospital gown. In embodiments, the RFID tag 514 may also be encoded with information related to the insulating properties of the accessories, which information may be encoded as a party of the identity of the accessory.

In embodiments, the RFID reader 512 may be communicatively coupled to the microcontroller 501 with wires or, alternatively, wirelessly, such as when the RFID reader 512 includes an RF transmitter (or transceiver) for transmitting the accessory identification signal and the microcontroller 501 includes an RF receiver (or transceiver) for receiving the accessory identification signal from the RFID reader 512.

In embodiments, the control unit 500 may further include an input device 506 communicatively coupled to the microcontroller 501. The input device 506 may be used to input data, operating parameters, and the like into the control unit 500. In embodiments, the input device 506 may be a conventional input device such as a keyboard, mouse, track pad, stylus or the like. In embodiments, the input device 506 may be communicatively coupled to the microcontroller 501 with wires or, alternatively, wirelessly, such as when the input device 506 includes an RF transmitter (or transceiver) for transmitting an input signal and the microcontroller 501 includes an RF receiver (or transceiver) for receiving the input signal from the input device. In embodiments, the input device 506 may be used to, for example, input target cooling temperatures into the control unit 500, input subject data into the control unit 500, control the operation of one or more cooling sources operatively connected to the control unit 500, and the like.

Still referring to FIGS. 14 and 15, in embodiments, the display device 504 is communicatively coupled to the microcontroller 501 and may be used to display data associated with the person support system 100, 101 and, more specifically, data related to the cooling of a subject position on the person support system 100, 101. In some embodiments, the display device 504 may be a touch screen and, as such, may also be used to input data, operating parameters, and the like, into the control unit 500. For example, in the embodiment depicted in FIG. 15, the display device 504 is a touch screen which includes various buttons including up/down arrow keys 520, 521, temperature check boxes 522, 523, and accessory check boxes 524, 525, 526, 527. The temperature check boxes 522, 523 may be used to toggle between the actual temperature (i.e., the temperature measured and indicated by the temperature signal from the temperature sensor 502) and the target temperature (i.e., the temperature input into the control unit by a user). With regard to the target temperature, up/down arrow keys 520, 521 may be used to increase or decrease the target temperature and/or scroll to a different temperature setting. The accessory check boxes 524, 525, 526, 527 may be used to select and/or identify the accessories associated with the subject and/or the person support system 100, 101. In the embodiment shown in FIG. 15, the accessory check boxes 524, 525, 526, 527 are associated with subject-specific accessories (i.e., garments worn by the subject positioned on the person support system 100, 101 and/or used in conjunction with the subject positioned on the person support system 100, 101).

In some embodiments described herein, the microcontroller 501 of the control unit 500 is communicatively coupled to a cooling source, such as the blower 400 (FIG. 9) and/or a thermoelectric cooler 420 (FIGS. 10 and 11). In these embodiments, the microcontroller 501 is programmed to output a control signal to operate the blower 400 and/or the thermoelectric cooler 420 based on input received from at least one of the temperature sensor 502, the RFID reader 512, the input device 506, the display device 504, or various combinations thereof.

For example, in embodiments, computer readable and executable instructions stored in the non-transitory memory cause the control unit to receive a temperature signal from the temperature sensor indicative of a measured temperature of the skin of a subject at a specific area or, alternatively, a measured temperature of a surface of the support pad. Thereafter, the control unit compares the measured temperature to a target temperature. If the measured temperature is not equal to the target temperature, the control unit outputs a control signal that adjusts an operating parameter of the cooling source, thereby increasing or decreasing cooling of the subject and/or support pad until the measured temperature is equal to the target temperature.

For example and without limitation, when the cooling source is a blower 400 as depicted in FIG. 9 and the microcontroller 501 of the control unit 500 determines that the temperature of a subject (i.e., the temperature of a specific portion of the skin of a subject or the temperature of the surface of the support pad on which the subject is positioned) measured with the temperature sensor 502 (i.e., the measured temperature or the actual temperature) is greater than a target temperature which may, in embodiments, be input in the control unit 500 through the display device 504 and/or the input device 506, the microcontroller 501 sends a signal to the blower 400 to increase the rotational speed of the blower 400 thereby increasing the flow of output fluid through the side rail 126 and increasing the extraction of heat from the top surface of the support pad 130 through the thermally conductive core portion 200.

Conversely, when the microcontroller 501 of the control unit 500 determines that the temperature of the subject (i.e., the temperature of a specific portion of the skin of a subject or the temperature of the surface of the support pad on which the subject is positioned) measured with the temperature sensor 502 (i.e., the measured temperature or the actual temperature) is less than the target temperature, the microcontroller 501 sends a signal to the blower 400 to decrease the rotational speed of the blower 400 thereby decreasing the flow of output fluid through the side rail 126 and decreasing the extraction of heat from the top surface of the support pad 130 through the thermally conductive core portion 200.

Alternatively, when the cooling source is a thermoelectric cooler 420 as depicted in FIG. 10 and the microcontroller 501 of the control unit 500 determines that the temperature of the subject (i.e., the temperature of a specific portion of the skin of a subject or the temperature of the surface of the support pad on which the subject is positioned) measured with the temperature sensor 502 (i.e., the measured temperature or the actual temperature) is less than a target temperature, the microcontroller 501 reduces the current and/or voltage supplied to the thermoelectric cooler 420 thereby decreasing the flow of heat through the thermoelectric cooler 420 from the cooling plate 422 to the heating plate 424 and decreasing the extraction of heat from the top surface of the support pad 130 through the thermally conductive core portion 200.

Conversely, when the microcontroller 501 of the control unit 500 determines that the temperature of the subject (i.e., the temperature of a specific portion of the skin of a subject or the temperature of the surface of the support pad on which the subject is positioned) measured with the temperature sensor 502 (i.e., the measured temperature or the actual temperature) is greater than a target temperature, the microcontroller 501 increases the current and/or voltage supplied to the thermoelectric cooler 420 thereby increasing the flow of heat through the thermoelectric cooler 420 from the cooling plate 422 to the heating plate 424 and increasing the extraction of heat from the top surface of the support pad 130 through the thermally conductive core portion 200.

In some embodiments, temperature measured with the temperature sensor 502 may be used to determine if a subject is appropriately positioned on the support pad 130 to facilitate effective cooling of a specific area of the subject. For example, in one embodiment, the actual temperature measured with the temperature sensor being relatively high when the temperature sensor 502 is applied directly to the skin of the subject may indicate that the subject is not properly positioned on the thermally conductive core portion of the support pad 130 (i.e., proper cooling is not taking place). Alternatively, the actual temperature measured with the temperature sensor 502 being at or above normal body temperature may indicate that insufficient cooling is occurring and that the cooling source should be adjusted (when present) or the thermally absorptive materials (i.e., PCMs or the like) exchanged or replaced (i.e., the cooling capacity of the materials is diminished or insufficient).

In embodiments where the thermally conductive core portion is thermally coupled to a passive cooling source such as the canister 480 containing thermally absorptive material 482 as depicted in FIG. 12, or the thermally conductive core portion 200 consists primarily of phase change material as depicted, for example, in FIG. 5A, the control unit 500 may be utilized to determine the proper thermally absorptive material for the canister 480 or thermally conductive core portion 200 for achieving the target temperature based on factors such as, for example and without limitation, the desired target temperature and the weight of the subject. For example, the non-transitory memory 510 of the control unit 500 may contain a look-up-table (LUT) of thermally absorptive materials (e.g., phase change materials, oils, coolant, etc.) that are indexed according to such factors as the target temperature and the weight of the subject. That is, the thermally absorptive materials may be indexed according to the target temperature which they are capable of achieving. In these embodiments, an operator may input the target temperature and the weight of the subject into the control unit 500 through the input device 506 or the display device 504. The processor 508 of the microcontroller 501 compares the input factors to the LUT of thermally absorptive materials and outputs to the display device one or more materials that may be used to reach the desired target temperature. While target temperature and weight of the subject have been provided as examples of factors that may be used to determine the appropriate thermally absorptive materials, it should be understood that other factors are contemplated and possible including, without limitation, the location of cooling (e.g., the sacral area, the scapular areas, buttocks, heels or the like), the ambient temperature, the length of the procedure, the material from which the support pad is formed, the type of accessories associated with the subject positioned on the person support system, and/or various combinations thereof.

For example, the control unit 500 may take into account variables that may adversely impact cooling, such as the presence of accessories 590 (e.g., linens, garments, and the like) in use with the person support system 100, 101 and/or subject which may have an insulating effect. Specifically, any accessories 590 which may be positioned between the skin of the subject and the surface of the support pad(s) may have an insulating effect which diminishes cooling. In this embodiment, the control unit 500 may take into account any accessories 590 being used in conjunction with the person support system 100, 101 and/or the subject positioned on the person support system 100, 101 together with a desired target temperature input in the control unit by a user and adjust either the target temperature and/or the recommended thermally absorptive materials to account for the insulating effects of any accessories 590 that are present.

For example, in embodiments where the thermally conductive core portion is thermally coupled to a cooling source such as the canister 480 containing thermally absorptive material 482 as depicted in FIG. 12, or the thermally conductive core portion 200 consisting primarily of phase change material as depicted, for example, in FIG. 5A, the control unit 500 may be utilized to determine the proper thermally absorptive material for the canister 480 or the thermally conductive core portion 200 for achieving the desired target temperature based on the desired target temperature and any accessories 590 that may be present. Specifically, a user may input the desired target temperature into the control unit 500 with the input device 506 or the display device 504. The target temperature may be displayed with the display device 504. A user may then input the identity of any accessories 590 that are present using either the input device 506 or the display device 504. Alternatively, the RFID reader 512 may be used to automatically detect the identity of any accessories 590 which include an RFID tag 514. Regardless of the input method, a list of the accessories 590 present may be displayed with the display device 504. In this embodiment the non-transitory memory 510 of the control unit 500 may contain a look-up-table (LUT) of thermally absorptive materials (e.g., phase change materials, oils, coolant, etc.) that are indexed according to the desired target temperature and the identity and insulating properties of various accessories. For example, the LUT may contain a list of thermally absorptive materials and each material may be associated with a combination of insulating properties of various accessories or combinations of accessories and correlated to a target temperature which may be achieved with the thermally absorptive material when the specified accessories are present. The processor 508 of the microcontroller 501 compares the input factors (i.e., the desired target temperature and the identified accessories) to the LUT of thermally absorptive materials and outputs one or more recommended thermally absorptive materials to the display device 504 that may be used to reach the desired target temperature at the surface of the skin in the presence of the identified accessories and/or provide a recommended time schedule for replacing the thermally absorptive material in order to achieve the desired target temperature. Alternatively, the non-transitory memory 510 of the microcontroller 501 may use an algorithm to identify one or more recommended thermally absorptive materials and/or recommended time schedules for replacing the thermally absorptive materials in order to reach the desired target temperature based on the input target temperature and the insulating properties of the identified accessories 590.

For example and without limitation, when the accessory 590 is an incontinence pad, the incontinence pad may provide thermal insulation to the skin of the subject thereby requiring additional cooling to reach the desired target temperature at the surface of the skin. Accordingly, a greater amount of heat withdrawal capacity may be necessary to reach the desired target temperature than in if the incontinence pad were not present. In this example, the control unit utilizes the identity of the accessory 590 in conjunction with the target temperature to determine a recommended thermally absorptive material and/or a recommended time schedule for replacing the thermally absorptive material in order to achieve the desired target temperature.

As another example, in embodiments where the thermally conductive core portion of the support pad 130 is thermally coupled to a cooling source, such as the blower 400 (FIG. 9) and/or a thermoelectric cooler 420 (FIGS. 10 and 11), and the microcontroller 501 is programmed to output a control signal to the cooling source to regulate cooling of the support pad 130, the control unit 500 may be utilized to adjust the target temperature to account for the insulating effect of any accessories 590 that may be present. Specifically, a user may input the desired target temperature into the control unit 500 with the input device 506 or the display device 504. The desired target temperature may be displayed with the display device 504. A user may then input the identity of any accessories 590 that are present using either the input device 506 or the display device 504. Alternatively, the RFID reader 512 may be used to automatically detect the identity of any accessories 590 which include an RFID tag 514. Regardless of the input method, a list of the accessories 590 present may be displayed with the display device 504. In this embodiment the non-transitory memory 510 of the control unit 500 may contain a look-up-table (LUT) of adjusted target temperatures that are indexed according to the desired target temperature and the identity and insulating properties of various combinations of accessories. For example, the LUT contains a list of adjusted target temperatures associated with one or more target temperatures and a corresponding accessory or combination of accessory. The adjusted target temperature is the actual temperature set point which may be utilized to obtain the desired target temperature at the surface of the skin in the presence of the identified accessories. The processor 508 of the microcontroller 501 compares the input factors (i.e., the desired target temperature and the identified accessories) to the LUT of adjusted target temperatures and outputs an adjusted target temperature to the display device 504 that may be used to reach the desired target temperature at the surface of the skin in the presence of the identified accessories. Alternatively, the non-transitory memory 510 of the microcontroller 501 may use an algorithm to identify an adjusted target temperature in order to reach the target temperature at the surface of the skin based on the input target temperature and the insulating properties of the identified accessories 590. Thereafter, the microcontroller 501 provides control signals to the cooling source (i.e., the blower 400 and/or thermoelectric cooler 420) to adjust an operating parameter of the cooling source and thereby achieve the adjusted target temperature at the surface of the accessory (i.e., at the top surface of the support pad) and, in turn, reach the desired target temperature at the surface of the skin. In this embodiment, the control unit 500 may further utilize the temperature signal from the temperature sensor 502 to control the cooling source in order to both achieve and maintain the adjusted target temperature at the surface of the accessory (i.e., at the top surface of the support pad) and, in turn, the desired target temperature at the surface of the subject's skin by controlled heat extraction through the thermally conductive core portion of the support pad 130.

For example and without limitation, when the target temperature is 75° F. and the accessory 590 is an incontinence pad, the incontinence pad may provide thermal insulation to the skin of the subject thereby requiring additional cooling to reach the desired target temperature at the surface of the skin. Accordingly, a greater amount of heat withdrawal capacity may be necessary to reach the desired target temperature at the surface of the skin than if the incontinence pad were not present. In this example, the control unit 500 utilizes the identity of the accessory 590 in conjunction with the desired target temperature to determine an adjusted target temperature at the surface of the accessory (i.e., at the surface of the support pad) such that the desired target temperature is reached at the surface of the skin. The control unit 500 then operates the cooling source, in conjunction with the temperature signal from the temperature sensor 502, to achieve and maintain the adjusted target temperature at the surface of the accessory (i.e., at the surface of the support pad) and, in turn, the desired target temperature at the surface of the subject's skin by controlled heat extraction through the thermally conductive core portion of the support pad 130.

In embodiments where the target temperature is adjusted to account for the presence of insulating accessories and/or the type of thermally absorptive materials are selected to account for the presence of insulating accessories, the comfort of the patient may be improved by preventing overcooling. Moreover, the workflow of a user (i.e., a caregiver) may be improved by minimizing the amount of cooling delivered to achieve a specific temperature, thereby decreasing the frequency of user intervention to monitor temperature and/or replace exhausted thermally absorptive materials. Further, by tailoring the operation of the cooling source to deliver only the minimal amount of cooling needed to obtain the desired target temperature may reduce the amount of energy expended on cooling.

Still referring to FIGS. 14 and 15, in embodiments, the control unit 500 may provide a visual indication of the temperature detected by the temperature sensors 502 on the display device 504, as described herein. For example, the visual indication may be a number displayed on a display device 504 of the control unit 500, or in the form of a graph. In some embodiments, a user may view the temperature and manually adjust the cooling source using the input device 506 communicatively coupled to the control unit 500. An adjustment to the cooling source may result in a decrease in the temperature, such as when the adjustment causes an increase in the flow of the fluid through the side rail 126 with the blower 400, or an increase in the temperature, such as when the adjustment causes a decrease in the flow of the fluid through the side rail 126 with the blower 400. Similar manual adjustments may be made to increase or decrease the cooling when the cooling source is, for example, a thermoelectric cooler 420

In still other embodiments, temperature sensors 502 may be included in the side rails 126, 127 or, in embodiments including a conduit for the cooling fluid, in the conduit. Accordingly, the control unit 500 may receive temperature readings from within the side rails 127, 127 in addition to temperature readings from a temperature sensor associated with the subject and/or the surface of the support pad 130. In such embodiments, the control unit 500 may determine a temperature gradient between the surface of the support pad and the side rails 126, 127. The flow of the cooling fluid may be increased or decreased in order to increase or decrease the temperature gradient and thus achieve a desired cooling rate. The control unit 500 may determine that an adjustment to the flow of the cooling fluid should be made by comparing the determined temperature gradient to a predetermined temperature gradient that is pre-set or set by a user and stored in the non-transitory memory 510.

In some embodiments, the cooling source may be positioned a distance away from the surface of the support pad(s). In some embodiments, the cooling source may be positioned from about 0.5 m to about 3 m from the support pads, from about 0.75 m to about 2 m from the support pads, or from about 1 m to about 1.5 m from the support pads in order to establish a suitable temperature gradient. In embodiments, the cooling source may be positioned proximate a head end of the person support system or the foot end of the person support system. The particular distance between the support pads and the cooling source and location of the cooling source may vary depending on the particular embodiment, provided that the cooling source 140 does not adversely impact the radiolucency of the support pad 130.

Based on the foregoing, it should be understood that the non-transitory memory 510 includes computer readable and executable instructions which, when executed by the processor 508, cause the microcontroller 501 to receive input signals from the temperature sensor 502, RFID reader 512, input device 506, and/or display device 504 and output signals to at least the display device 504 based on the input signals received. In some embodiments, the microcontroller 501 also outputs control signals to a cooling source such as a blower 400 or a thermoelectric cooler 420 to regulate cooling of a support pad 130.

In embodiments described herein, the targeted cooling of at least a portion of a support pad is achieved by conducting heat from the support pad and dissipating that heat with a heat sink, either by conduction, convection, radiation, or combinations thereof. The heat conducted away from the support pad is, effectively, waste heat. In some embodiments of the person support systems described herein, the heat conducted away from the support pad may be recycled and repurposed. For example, in embodiments, the heat conducted away from the support pad may be recycled to warm the subject positioned on the person support system.

Figure 16:
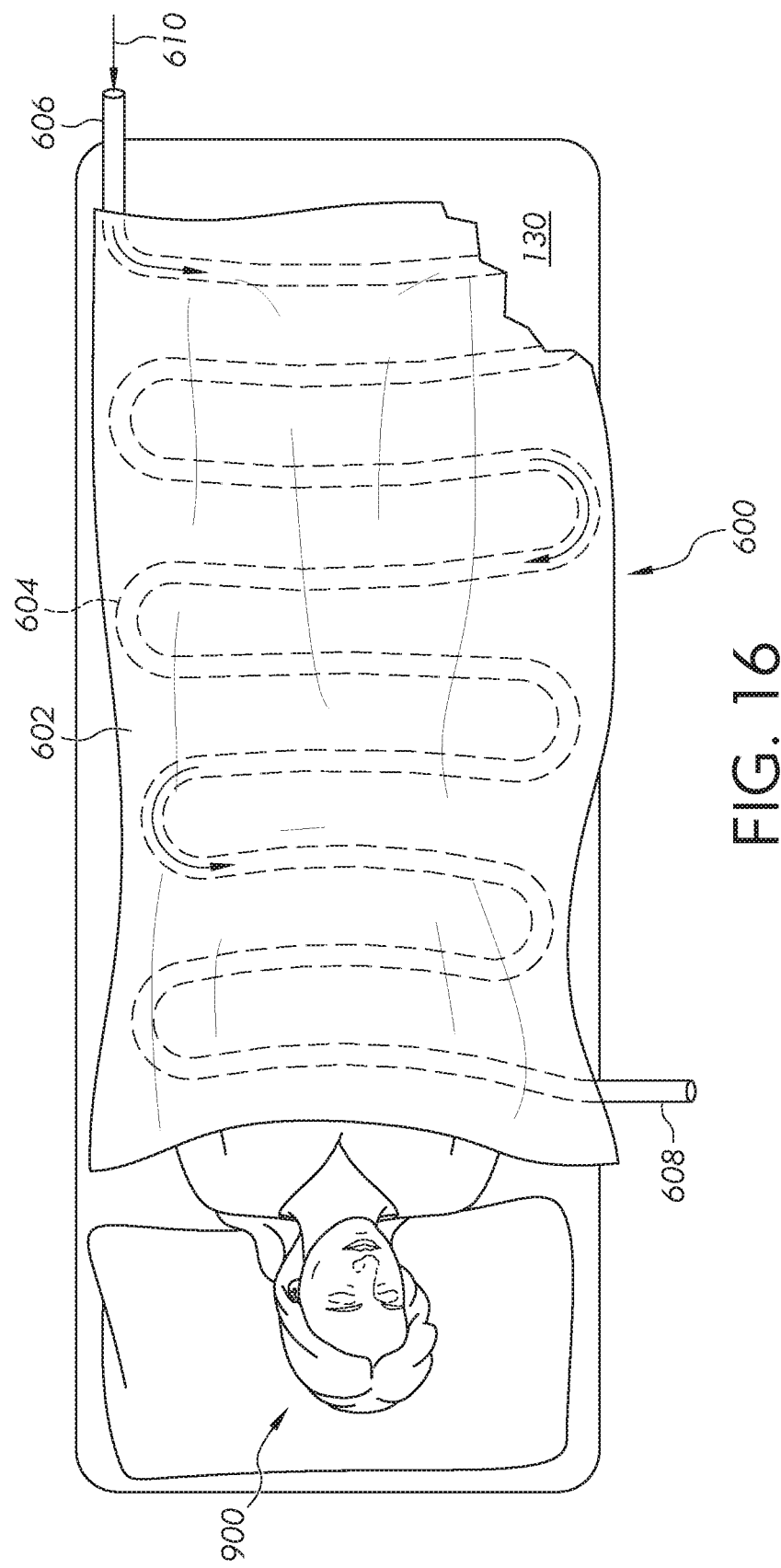
FIG. 16 schematically depicts one embodiment of a warming blanket for use with one or more embodiments of the person support systems described herein.

Referring to FIG. 16 by way of example, a warming blanket 600 is schematically depicted for use in warming a subject 900 positioned on a support pad 130 of a person support system. In embodiments, the warming blanket 600 may include a sheet portion 602 which includes a flexible conduit 604. For example, the sheet portion 602 may include multiple plies and the flexible conduit 604 may be disposed between two of the plies. As shown in FIG. 16, the flexible conduit 604 may have a serpentine configuration within the sheet portion 602 of the warming blanket 600. In the embodiment of the flexible conduit 604 depicted in FIG. 16, the flexible conduit includes an inlet 606 for receiving a warming fluid 610 (schematically depicted by arrows) and an outlet 608 for expelling the warming fluid 610.

Figure 17:
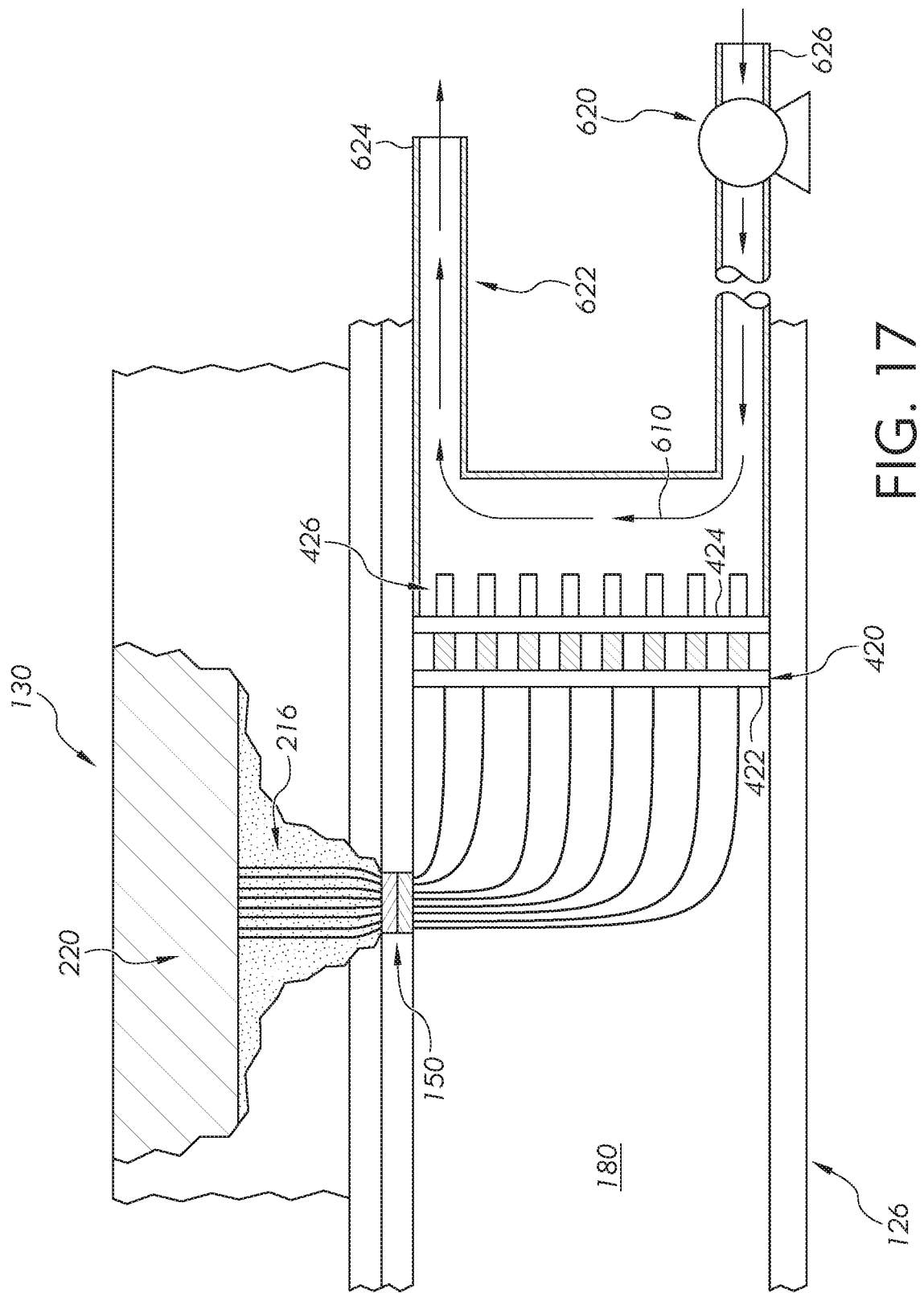
FIG. 17 schematically depicts an embodiment of a system for delivering warming fluid to the warming blanket of FIG. 16.

Referring now to FIGS. 16 and 17, the side rail 126 of the person support system may include a thermoelectric cooler 420 thermally coupled to a thermally conductive core portion 200 of the support pad 130, as described herein with respect to FIG. 10. However, in this embodiment, the side rail 126 may further include a frame conduit 622 extending into the interior channel 180 of the side rail 126. The frame conduit 622 is positioned relative to the heating plate 424 of the thermoelectric cooler 420 and directs a flow of warming fluid 610 across the heating plate 424 and the cooling fins 426 extending from the heating plate 424. In the embodiment shown in FIG. 17, the frame conduit 622 is coupled to a pump 620 which circulates the warming fluid 610 through the frame conduit 622. The frame conduit 622 further includes a frame outlet 624 which is fluidly coupled to the inlet 606 of the warming blanket 600 and a frame inlet which is fluidly coupled to the outlet 608 of the warming blanket 600. Accordingly, it should be understood that, in this embodiment, the flexible conduit 604 of the warming blanket 600 and the frame conduit 622 form a closed loop system.

In embodiments, the warming fluid 610 directed through the flexible conduit 604 and the frame conduit 622 may be, for example, a gas such as, without limitation, air or nitrogen. Alternatively, the warming fluid 610 directed through the flexible conduit 604 and the frame conduit 622 may be, for example, a liquid such as, without limitation, water, mineral oil, or the like.

In operation, the thermoelectric cooler 420 conducts heat from the support pad 130 as described hereinabove with respect to FIG. 10. Simultaneously, the pump 620 pumps the warming fluid 610 through the frame conduit 622 such that the warming fluid 610 contacts the heating plate 424 and cooling fins 426 of the thermoelectric cooler 420, thereby heating the warming fluid 610. The heated warming fluid 610 exits the frame conduit 622 at frame outlet 624 and enters the inlet 606 of the flexible conduit 604 of the warming blanket 600. The warming fluid 610 is circulated through the flexible conduit 604 of the warming blanket 600 and the heat from the warming fluid 610 is transferred to a subject 900 positioned beneath the warming blanket 600 on the support pad 130, thereby warming the subject 900. The warming fluid 610 exits the flexible conduit 604 at the outlet 608 and is re-circulated into the frame inlet 626 of the frame conduit 622 and through the pump 620. In this embodiment, the flexible conduit 604 of the warming blanket receives the warming fluid 610 from the heating plate 424 of the thermoelectric cooler 420 by convection, specifically forced convection.

While a closed loop embodiment of the warming blanket has been described, it should be understood that an open loop embodiment is contemplated and possible. Referring again to FIGS. 16 and 17, in the open loop embodiment, the frame outlet 624 is coupled to the inlet 606 of the flexible conduit 604. However, the frame inlet 626 is coupled to atmosphere (i.e., open) as is the outlet 608 of the flexible conduit 604. In this embodiment the warming fluid 610 may be air.

In operation, the thermoelectric cooler 420 conducts heat from the support pad 130 as described hereinabove with respect to FIG. 10. Simultaneously, the pump 620 draws in warming fluid 610 (i.e., air) through the frame inlet 626 of the frame conduit 622 such that the warming fluid 610 contacts the heating plate 424 and cooling fins 426 of the thermoelectric cooler 420, thereby heating the warming fluid 610. The heated warming fluid 610 exits the frame conduit 622 at frame outlet 624 and enters the inlet 606 of the flexible conduit 604 of the warming blanket 600. The warming fluid 610 is circulated through the flexible conduit 604 of the warming blanket 600 and the heat from the warming fluid 610 is transferred to a subject 900 positioned beneath the warming blanket 600 on the support pad 130, thereby warming the subject 900. The warming fluid 610 exits the flexible conduit 604 at the outlet 608 and is expelled to atmosphere. In this embodiment, the flexible conduit 604 of the warming blanket receives the warming fluid 610 from the heating plate 424 of the thermoelectric cooler 420 by convection, specifically forced convection.

Still referring to FIGS. 16 and 17, in another open loop embodiment, the frame outlet 624 is coupled to the inlet 606 of the flexible conduit 604. However, the frame inlet 626 is coupled to atmosphere (i.e., open) and the outlet 608 of the flexible conduit 604 of the warming blanket 600 is plugged. In this embodiment the flexible conduit 604 is perforated along its length between the inlet 606 and the outlet 608. In this embodiment the warming fluid 610 may be air.

In operation, the thermoelectric cooler 420 conducts heat from the support pad 130 as described hereinabove with respect to FIG. 10. Simultaneously, the pump 620 draws in warming fluid 610 (i.e., air) through the frame inlet 626 of the frame conduit 622 such that the warming fluid 610 contacts the heating plate 424 and cooling fins 426 of the thermoelectric cooler 420, thereby heating the warming fluid 610. The heated warming fluid 610 exits the frame conduit 622 at frame outlet 624 and enters the inlet 606 of the flexible conduit 604 of the warming blanket 600. The warming fluid 610 is circulated through the flexible conduit 604 of the warming blanket 600. As the warming fluid 610 is circulated, the warming fluid 610 exits the flexible conduit 604 through the perforations along its length, thereby transferring heat from the warming fluid 610 to a subject 900 positioned beneath the warming blanket 600 on the support pad 130. In this embodiment, the flexible conduit 604 of the warming blanket receives the warming fluid 610 from the heating plate 424 of the thermoelectric cooler 420 by convection, specifically forced convection.

Still referring to FIGS. 16 and 17, in yet another open loop embodiment, natural convection is used to circulate the warming fluid 610 from the heating plate 424 of the thermoelectric cooler 420 through the flexible conduit 604 of the warming blanket. In this embodiment, the frame outlet 624 is coupled to the inlet 606 of the flexible conduit 604. However, the frame inlet 626 is coupled to atmosphere (i.e., open) as is the outlet 608 of the flexible conduit 604 of the warming blanket 600. In this embodiment the pump 620 is not coupled to the frame conduit 622. In this embodiment the warming fluid 610 is air.

In operation, the thermoelectric cooler 420 conducts heat from the support pad 130 as described hereinabove with respect to FIG. 10. Simultaneously, warming fluid 610 (i.e., air) in the frame conduit 622 contacts the heating plate 424 and cooling fins 426 of the thermoelectric cooler 420, thereby heating the warming fluid 610 by convection. The heated warming fluid 610 rises and exits the frame conduit 622 at frame outlet 624 and enters the inlet 606 of the flexible conduit 604 of the warming blanket 600. The warming fluid 610 circulates through the flexible conduit 604 of the warming blanket 600 and the heat from the warming fluid 610 is transferred to a subject 900 positioned beneath the warming blanket 600 on the support pad 130, thereby warming the subject 900. The warming fluid 610 exits the flexible conduit 604 at the outlet 608 and is expelled to atmosphere.

Referring to FIGS. 16 and 9, in an alternative embodiment, the warming blanket 600 may be utilized in conjunction with side rail 126 and blower 400 as depicted in FIG. 9. Specifically, the inlet 606 of the flexible conduit 604 of the warming blanket 600 may be fluidly coupled to the side rail 126 such that output fluid 402 is directed into and circulated through the flexible conduit 604 of the warming blanket 600 after passing around and through the thermally conductive fibers 220 of the second pigtail connector 218. In this manner, heat conducted from the top surface of the support pad 130 through the thermally conductive core portion 200, the first pigtail connector 216, and the magnetic coupler 250 is recycled into the warming blanket 600.

Figure 18:
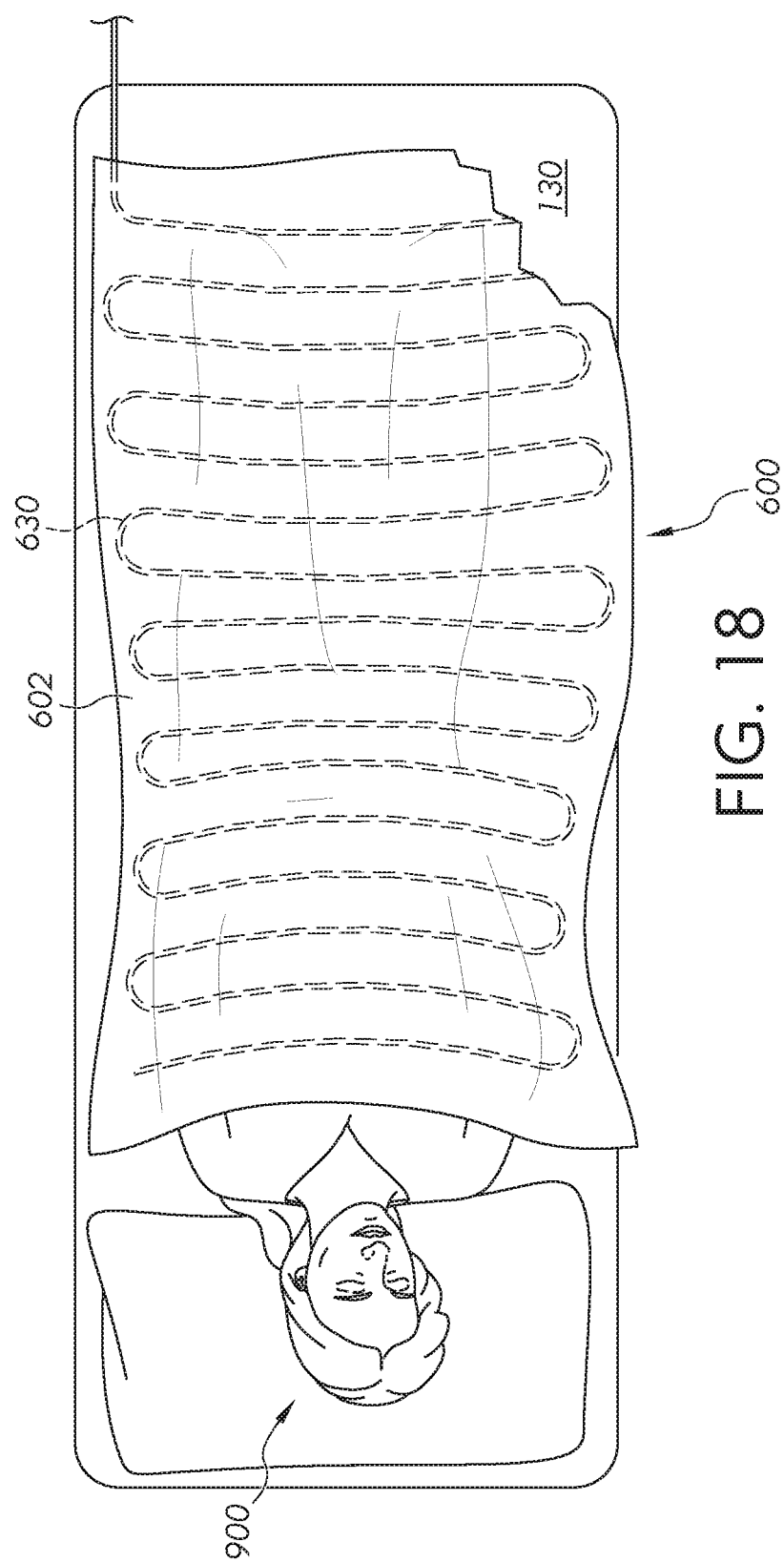
FIG. 18 schematically depicts another embodiment of a warming blanket for use with one or more embodiments of the person support systems described herein.
Figure 19:
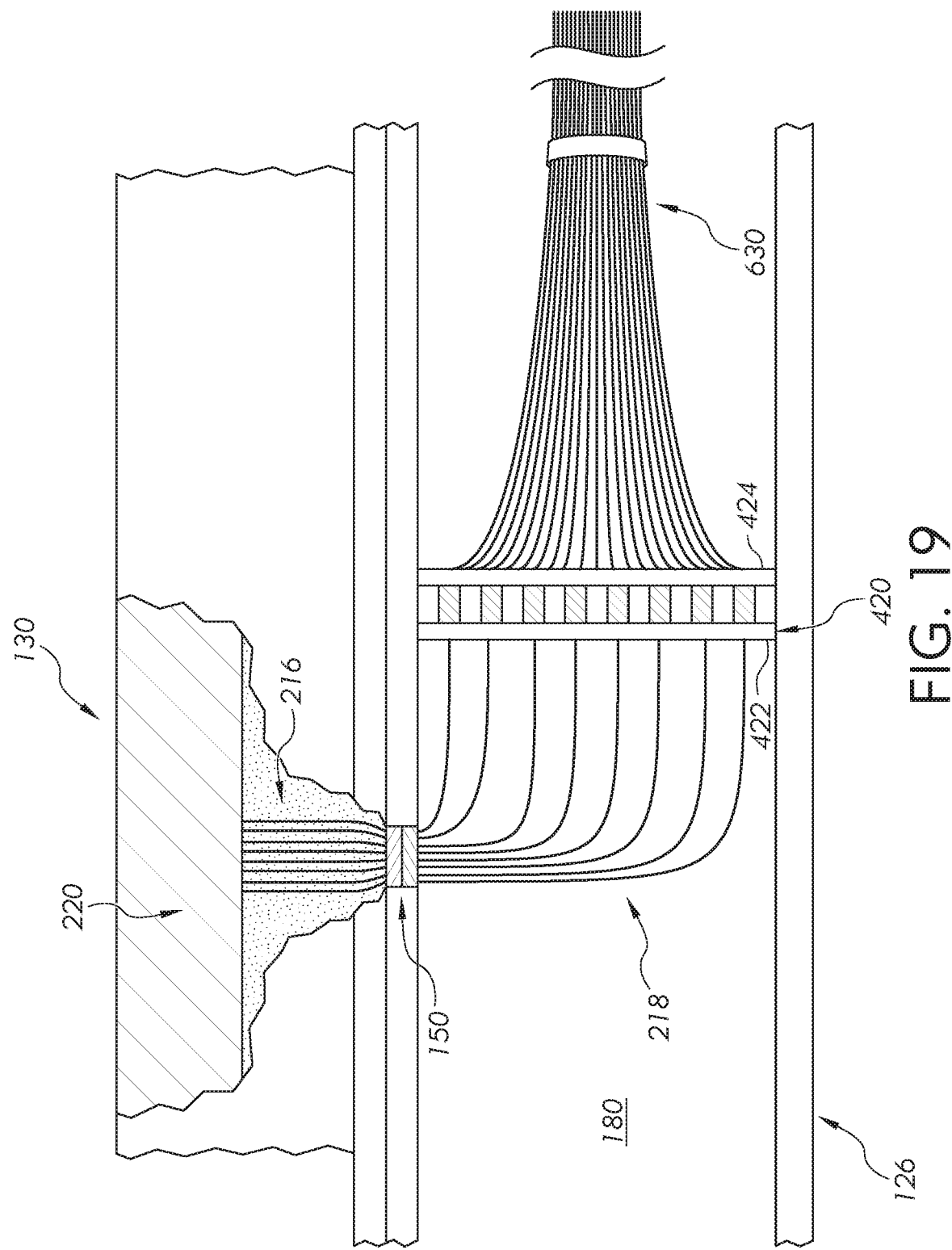
FIG. 19 schematically depicts an embodiment of a system for heating the warming blanket of FIG. 18.

Referring now to FIGS. 18 and 19, in an alternative embodiment, the warming blanket 600 includes a thermally conductive element 630 disposed between two plies of the warming blanket or, alternatively, embedded in a single ply of the warming blanket 600, such as when the thermally conductive element 630 is woven into the material of the ply. As shown in FIG. 18, the thermally conductive element may have a serpentine configuration within the sheet portion 602 of the warming blanket 600. In the embodiment depicted in FIG. 18, the thermally conductive element 630 may be formed from, for example and without limitation, carbon fibers such as pitch-based carbon fibers, thermally conductive polymer fibers as described herein, or combinations thereof.

The side rail 126 of the person support system may include a thermoelectric cooler 420 thermally coupled to a thermally conductive core portion 200 of the support pad 130, as described herein with respect to FIG. 10. However, in this embodiment, the thermally conductive element 630 of the warming blanket 600 is thermally coupled to the heating plate 424 of the thermoelectric cooler 420.

In operation, the thermoelectric cooler 420 conducts heat from the support pad 130 as described hereinabove with respect to FIG. 10. After the heat is transferred from the cooling plate 422 of the thermoelectric cooler 420 to the heating plate 424 of the thermoelectric cooler 420, the heat is conducted away from the heating plate 424 with the thermally conductive element 630. As the heat is conducted along the length of the thermally conductive element 630 and through the warming blanket 600, heat from the thermally conductive element 630 is transferred to a subject 900 positioned beneath the warming blanket 600 on the support pad 130, thereby warming the subject 900.

While various embodiments of support pads which include thermally conductive core portions that are actively cooled by thermally coupling the thermally conductive core portions to a cooling source which creates a temperature gradient between the top surface of the support pad and the cooling source have been described herein, it should be understood that alternative embodiments are contemplated and possible. For example, in some embodiments described here, the thermally conductive core portions may provide passive cooling by absorbing and dissipating heat without being thermally coupled to a cooling source.

Figure 20:
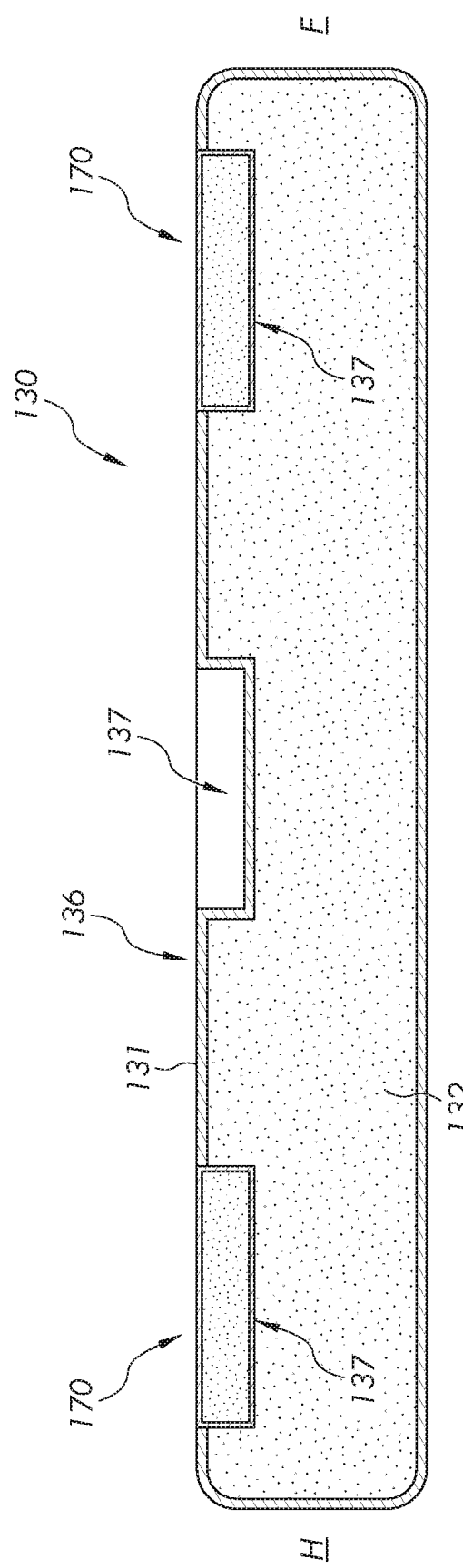
FIG. 20 schematically depicts an alternative embodiment of a support pad with recesses for receiving foam plugs or thermally conductive core portions.
Figure 21:
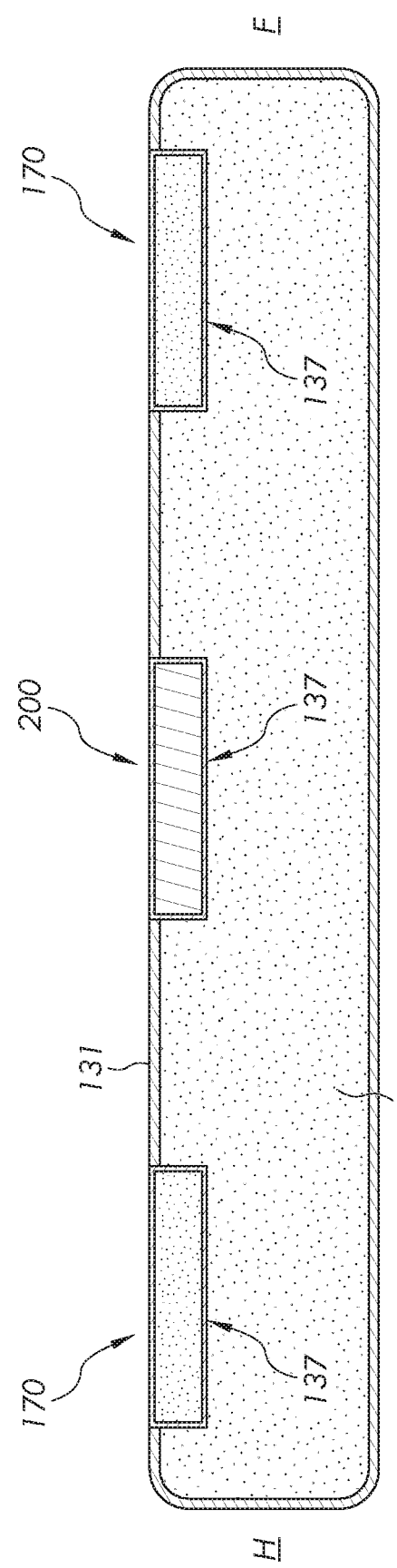
FIG. 21 schematically depicts the support pad of FIG. 20 with a thermally conductive core portion disposed in one recess and foam plugs positioned in other recesses.

Referring to FIGS. 20 and 21 by way of example, FIG. 20 schematically depicts a cross-section of one embodiment of a support pad 130. In this embodiment, the support pad 130 is sized and shaped to extend from a head end H of a person support system to the foot end F of the person support system. However, it should be understood that, in alternative embodiments, the support pad 130 may be sized and shaped to extend only over a portion of the person support system. The support pad 130 may include a core part 132 enveloped in a cover material 136, as described hereinabove with respect to FIG. 4B. However, in this embodiment, the support pad 130 includes at least one recess 137 formed in the core part 132 and extending up through the top surface 131 of the support pad 130. In embodiments, the recesses 137 may be located in the core part 132 in, for example and without limitation, areas that correspond to the sacral area, buttocks, scapular areas, and/or heels of a subject when the subject is positioned on the top surface 131 of the support pad 130. The recesses 137 are sized and shaped to removably receive a foam plug 170 that is formed from the same or similar material as the core part 132. In embodiments, the foam plug 170 may be enveloped in a cover material that is the same as the cover material 136 of the support pad 130. When the foam plugs 170 are inserted in the corresponding recesses 137, the top of the foam plugs are flush with the top surface 131 of the support pad 130.

In the embodiment of the support pad 130 shown in FIGS. 20 and 21, the foam plug(s) 170 may be removed from the recesses 137 and replaced with thermally conductive core portions 200, as depicted in FIG. 21. Like the foam plugs 170, the top surfaces of the thermally conductive core portions 200 are flush with the top surface 131 of the support pad 130 when inserted in the recesses 137. The thermally conductive core portions 200 may be any one of the thermally conductive core portions described herein including, without limitation, the various embodiments of thermally conductive core portions depicted in FIGS. 5A-5G. In embodiments where the thermally conductive core portions 200 depicted in FIG. 5B are used, the thermally conductive core portions 200 may optionally include the thermal transport layer 214. However, when the thermally conductive core portion of FIG. 5B is used in conjunction with the support pad 130 depicted in FIGS. 20 and 21, the thermally conductive core portion is formed without the pigtail connector 216. Similarly, when the thermally conductive core portions 200 are as depicted in FIGS. 5E-5G, the thermally conductive core portions are constructed without the pigtail connector 216. That is, in the embodiments of the support pad 130 depicted in FIGS. 20 and 21, heat from a subject positioned on the top surface 210 of the thermally conductive core portion 200 is conducted into the support matrix 204 of the thermally conducted core portion 200 and dissipated therein rather than further conducted out of the support matrix 204.

Still referring to FIGS. 20 and 21, a support pad 130 which includes recesses 137 in which foam plugs 170 and/or thermally conductive core portions 200 may be removably positioned facilitates tailoring the cooling capacity of the support pad 130 to specific situations and/or subjects. For example, in embodiments, where no cooling is desired, foam plugs 170 may be positioned in the recesses 137. Where cooling is desired at a specific location, the foam plug 170 may be removed from the corresponding recess and replaced with a thermally conductive core portion 200. The thermally conductive core portion 200 may be selected from a plurality of different thermally conductive core portions 200 to achieve a desired amount of cooling. For example and without limitation, a plurality of thermally conductive core portions 200 may be constructed as depicted in FIG. 5A and/or FIG. 5B. Each of the plurality of thermally conductive core portions 200 may be constructed from different materials (e.g., different phase change materials or the like) and, as a result, may have different cooling characteristics. The specific thermally conductive core portion 200 inserted in the recess 137 of the support pad 130 may be selected from the plurality of thermally conductive core portions based on cooling characteristics in order to achieve a desired amount of cooling.

Based on the foregoing it should be understood that, in one embodiment, the support pad of FIGS. 20 and/or 21 may form a component of a subject cooling system which includes the support pad 130 having at least one recess formed in the core part 132 of the support pad 130; a foam plug sized and shaped to be received in the recess formed in the core part of the support pad 130; and a plurality of thermally conductive core portions 200 sized and shaped to be received in the recess formed in the core part. Each of the thermally conductive core portions 200 may have cooling characteristics different than the other thermally conductive core portions of the plurality. The thermally conductive core portions may be constructed as depicted in any one of FIGS. 5A-5G.

The embodiment of the support pad 130 depicted in FIGS. 20 and 21 provides a customizable surface that can be tailored to specific cooling requirements by exchanging foam plugs for thermally conductive core portions and vice-versa. Because the thermally conductive core portions are recessed into the surface, the amount of cooling provided can be tailored up to a maximum cooling by, for example, adjusting the thickness of the thermally conductive core portions (i.e., using a combination of thermally conductive core portions and foam plug "spacers" inserted in the recesses with the thermally conductive core portions positioned on the spacers) or selecting thermally conductive core portions with different types of phase change materials with different melting temperatures or the like.

While specific reference has been made herein to use of the support pads with thermally conductive core portions in conjunction with subject support systems such as surgical tables and/or spine tables, it should be understood that use of the support pads with other types of subject support systems are contemplated and possible. For example, some embodiments of the support pads with thermally conductive core portions, such as the embodiment depicted in FIGS. 20 and 21, may be used in conjunction with stretchers and or gurneys. Alternatively, a variation of the embodiment of the support pad 130 depicted in FIG. 4B may be utilized in conjunction with a stretcher or gurney.

Figure 22:
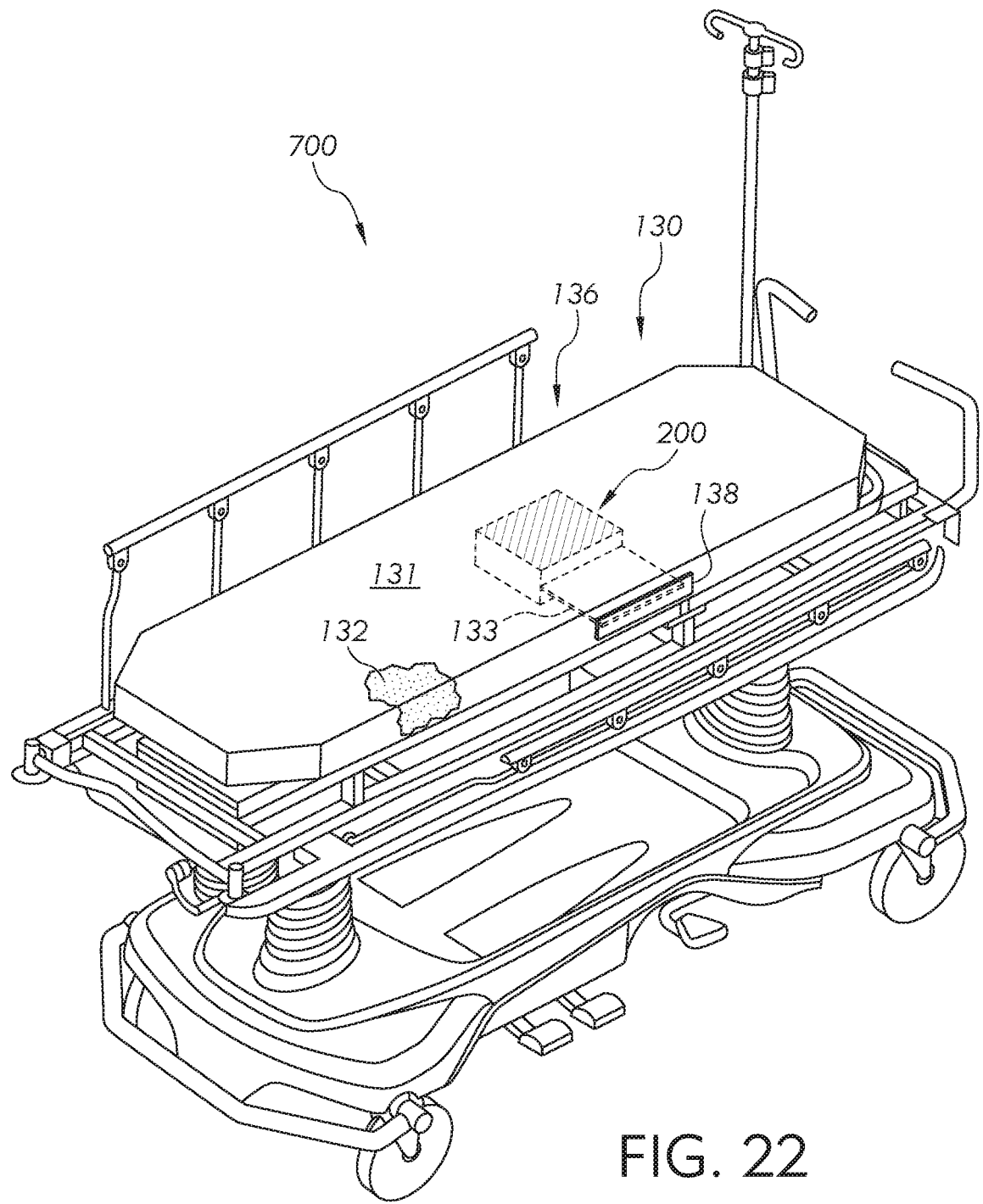
FIG. 22 schematically depicts a mobile person support system, such as a stretcher, having a support pad with a thermally conductive core portion in accordance with one or more embodiments described herein.

Referring to FIG. 22 by way of example, a stretcher 700 which includes a support pad 130 is schematically depicted. The support pad 130 is generally constructed as shown in FIG. 4B. That is, the core part 132 of the support pad 130 may be formed with a channel 133 extending through the foam of the core part 132 from a recess where the thermally conductive core portion 200 is located to the edge of the support pad 130, as depicted in FIG. 22. The channel 133 may facilitate removing and replacing the thermally conductive core portion 200 with, for example, a thermally conductive core portion constructed from different thermally conductive material having different cooling characteristics or a "fresh" thermally conductive core portion (such as when the thermally conductive core portion 200 has reached an equilibrium temperature with a subject positioned on the support pad 130 and the cooling capabilities of the thermally conductive core portion 200 are exhausted). In other embodiments, the channel 133 may facilitate removing and replacing the thermally conductive core portion 200 in the recess with, for example, a plug of foam material similar or identical to the foam of the core part 132. The thermally conductive core portion 200 may be replaced with a plug of foam material when, for example, focal cooling of a particular area is not needed or desired. The plug of foam material fills the recess previously occupied by the thermally conductive core portion 200, thereby maintaining the support provided by the support pad 130 in the absence of the thermally conductive core portion 200. In embodiments, access to the channel 133 in the core part 132 may be provided by, for example, a closure 138 formed in the cover material 136 enveloping the core part 132. The closure 138 may be, for example and without limitation, a flap, a hook-and-loop closure, a zipper, or the like. In the embodiment depicted in FIG. 22, the thermally conductive core portion 200 may be a thermally conductive core portion as shown and described in FIGS. 5A-5G.

The embodiment of the support pad 130 depicted in FIG. 22 allows focal cooling to be provided without modification of the structural components of the stretcher 700. That is, the support pad 130 may be retrofit to existing stretchers without modification of the stretcher frame.

While various embodiments of support pads with cooling features have been shown and described herein in conjunction with person support systems, it should be understood that other applications are contemplated and possible. For example, the support pads described herein may be used in conjunction with other medical equipment including, without limitation, wheelchairs, stretchers, gurneys, and the like or any other medical equipment which utilizes a support surface on which a subject may be positioned for extended periods of time.

Various embodiments described herein include cooling features in the form of thermally conductive elements in a support pad. The cooling features may reduce a temperature of the tissue in contact with the support pad, which may further reduce the likelihood of a pressure ulcer. In various embodiments, the support pad is made of radiolucent materials to enable the support pad to be used without interfering with imaging techniques utilized in conjunction with the person support systems on which the support pads are positioned.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A person support system comprising:
a longitudinal frame comprising at least one side rail;
a support pad positioned on the longitudinal frame, the support pad comprising a thermally conductive core portion comprising a support matrix and at least one thermally conductive element; and
a cooling source thermally coupled to the thermally conductive core portion through the at least one side rail with a connector comprising thermally conductive fibers, wherein the cooling source draws heat from the thermally conductive core portion through the at least one thermally conductive element and the thermally conductive fibers of the connector thereby cooling at least the thermally conductive core portion of the support pad,
wherein the cooling source is thermally coupled to the thermally conductive core portion with a magnetic coupler.

2. The person support system of claim 1, wherein:
the person support system further comprises a control unit communicatively coupled to a temperature sensor, the control unit comprising a processor and a non-transitory memory storing computer readable and executable instructions which, when executed by the processor, cause the control unit to:
receive a temperature signal from the temperature sensor indicative of a measured temperature of skin of a subject or a surface of the support pad;
compare the measured temperature to a target temperature; and
adjust an operating parameter of the cooling source when the measured temperature is not equal to the target temperature, thereby increasing or decreasing cooling of the support pad until the measured temperature is equal to the target temperature.

3. The person support system of claim 1, wherein:
the person support system further comprises a control unit communicatively coupled to an input device and a temperature sensor, the control unit comprising a processor and a non-transitory memory storing computer readable and executable instructions which, when executed by the processor, cause the control unit to:
receive an input indicative of a target temperature;
receive an input indicative of an identity of an accessory;
determine an adjusted target temperature based on the target temperature and the identity of the accessory;
receive a temperature signal from the temperature sensor indicative of a measured temperature of a surface of the support pad; and
adjust an operating parameter of the cooling source thereby increasing or decreasing cooling of the support pad until the measured temperature is equal to the adjusted target temperature.

4. The person support system of claim 3 further comprising an RFID reader communicatively coupled to the control unit, wherein the computer readable and executable instructions, when executed by the processor, further cause the control unit to receive an accessory identification signal from the RFID reader indicative of the identity of the accessory, wherein the accessory identification signal is the input indicative of the identity of the accessory.

5. The person support system of claim 1, wherein:
the cooling source comprises thermally absorptive material; and
the person support system further comprises a control unit communicatively coupled to an input device, the control unit comprising a processor and a non-transitory memory storing computer readable and executable instructions which, when executed by the processor, cause the control unit to:
receive an input indicative of a target temperature;
receive an input indicative of an identity of an accessory; and
determine a recommended thermally absorptive material based on the target temperature and the identity of the accessory.

6. The person support system of claim 5 further comprising an RFID reader communicatively coupled to the control unit, wherein the computer readable and executable instructions, when executed by the processor, further cause the control unit to receive an accessory identification signal from the RFID reader indicative of the identity of the accessory, wherein the accessory identification signal is the input indicative of the identity of the accessory.

7. The person support system of claim 5, wherein the computer readable and executable instructions, when executed by the processor, further cause the control unit to determine a recommended time schedule for replacing the thermally absorptive material to achieve the target temperature.

8. The person support system of claim 1, wherein:
The cooling source comprises a thermally absorptive material disposed in a canister; and
the thermally conductive core portion of the support pad is thermally coupled to the canister with the thermally conductive fibers of the connector.

9. The person support system of claim 1, wherein the at least on thermally conductive element comprises:
- thermally conductive particles suspended in the support matrix; and
- at least one thermal transport layer thermally coupled to the support matrix and configured to conduct heat from the support matrix.

10. The person support system of claim 9, wherein a number of thermally conductive particles per unit volume of the support matrix is greatest proximate a top surface of the thermally conductive core portion and decreases with increasing distance from the top surface of the thermally conductive core portion.

11. The person support system of claim 9, wherein the thermally conductive core portion further comprises thermally absorptive particles suspended in the support matrix.

12. The person support system of claim 11, wherein a number of thermally absorptive particles per unit volume of the support matrix is greatest at a top surface of the thermally conductive core portion and decreases with increasing distance from the top surface of the thermally conductive core portion.

13. The person support system of claim 1, wherein the at least one thermally conductive element of the thermally conductive core portion comprises an array of thermally conductive fibers suspended in the support matrix and arranged to conduct heat away from a top surface of the thermally conductive core portion, wherein at least a portion of the array of thermally conductive fibers extend from at least one of a side surface of the support matrix and a bottom surface of the support matrix.

14. The person support system of claim 13, wherein the array of thermally conductive fibers comprises a first plurality of thermally conductive fibers and a second plurality of thermally conductive fibers, wherein the second plurality of thermally conductive fibers are arranged parallel to a top surface of the thermally conductive core portion.

15. The person support system of claim 14, wherein the first plurality of thermally conductive fibers are obliquely oriented with respect to the second plurality of thermally conductive fibers.

16. The person support system of claim 15, wherein the first plurality of thermally conductive fibers and the second plurality of thermally conductive fibers have different thermal conductivities and the thermal conductivity of the first plurality of thermally conductive fibers is greater than the thermal conductivity of the second plurality of thermally conductive fibers.

17. The person support system of claim 14, wherein the second plurality of thermally conductive fibers are arranged in the support matrix such that a density of the second plurality of thermally conductive fibers in the support matrix is greatest at a top surface of the thermally conductive core portion and decreases with increasing distance from the top surface of the thermally conductive core portion.

18. The person support system of claim 14, wherein:
- the second plurality of thermally conductive fibers comprises thermally conductive fibers having different thermal conductivities; and
- the second plurality of thermally conductive fibers are arranged in the support matrix such that fibers having relatively greater thermal conductivity are positioned closer to a top surface of the thermally conductive core portion than thermally conductive fibers having relatively lower thermal conductivity.

19. The person support system of claim 1, wherein the at least one thermally conductive element envelops the support matrix.

20. The person support system of claim 1, wherein:
- the cooling source is a thermoelectric cooler and the thermally conductive core portion is thermally coupled to a cooling plate of the thermoelectric cooler; and
- the person support system further comprises a warming blanket thermally coupled to a heating plate of the thermoelectric cooler.

21. The person support system of claim 20, wherein the warming blanket comprises a flexible conduit receiving a warming fluid from the heating plate of the thermoelectric cooler by convection.

22. The person support system of claim 20, wherein the warming blanket comprises a thermally conductive element and the thermally conductive element of the warming blanket is thermally coupled to the heating plate of the thermoelectric cooler.

23. The person support system of claim 1, wherein:
- the cooling source is a thermoelectric cooler disposed in the at least one side rail of the longitudinal frame; and
- the thermally conductive core portion of the support pad is thermally coupled to a cooling plate of the thermoelectric cooler with the thermally conductive fibers of the connector.

24. The person support system of claim 1, wherein:
- the cooling source is a blower configured to direct a flow of fluid through an interior channel of the at least one side rail; and
- the thermally conductive core portion of the support pad is thermally coupled to the flow of fluid with the thermally conductive fibers of the connector.

25. The person support system of claim 1, wherein:
- the support pad comprises a core part; and
- the thermally conductive core portion is disposed in a recess formed in the core part.

26. The person support system of claim 25, wherein the core part comprises a channel extending from the recess to an edge of the support pad, the channel facilitating insertion and removal of the core part in the recess.

27. A person support system comprising:
- a longitudinal frame comprising at least one side rail;
- a support pad positioned on the longitudinal frame, the support pad comprising a thermally conductive core portion comprising a support matrix and at least one thermally conductive element;
- a cooling source thermally coupled to the thermally conductive core portion through the at least one side rail with a connector comprising thermally conductive fibers, wherein the cooling source draws heat from the thermally conductive core portion through the at least one thermally conductive element and the thermally conductive fibers of the connector thereby cooling at least the thermally conductive core portion of the support pad;
- a control unit communicatively coupled to an input device, an RFID reader, and a temperature sensor, the control unit comprising a processor and a non-transitory memory storing computer readable and executable instructions which, when executed by the processor, cause the control unit to:
  - receive an input indicative of a target temperature;
  - receive an accessory identification signal from the RFID reader indicative of an identity of an accessory;

determine an adjusted target temperature based on the target temperature and the identity of the accessory;

receive a temperature signal from the temperature sensor indicative of a measured temperature of a surface of the support pad; and adjust an operating parameter of the cooling source thereby increasing or decreasing cooling of the support pad until the measured temperature is equal to the adjusted target temperature.

28. A subject cooling system comprising:

a support pad comprising a core part and at least one recess formed in the core part, the at least one recess extending through a top surface of the support pad;

a foam plug comprising a shape and a size corresponding to the at least one recess formed in the core part of the support pad; and a set of thermally conductive core portions, each thermally conductive core portion of the set of thermally conductive core portions comprising a shape and a size corresponding to the at least one recess formed in the core part of the support pad, wherein:

each thermally conductive core portion of the set of thermally conductive core portions has different cooling characteristics than at least one other thermally conductive core portion in the set of thermally conductive core portions; and the foam plug and each thermally conductive core portion of the set of thermally conductive core portions are interchangeably insertable into the at least one recess formed in the core part of the support pad.

29. The subject cooling system of claim 28, wherein at least one thermally conductive core portion of the set of thermally conductive core portions comprises a support matrix and thermally absorptive particles suspended in the support matrix.

30. The subject cooling system of claim 28, wherein at least one thermally conductive core portion of the set of thermally conductive core portions comprises a support matrix and an array of thermally conductive fibers suspended in the support matrix and arranged to conduct heat away from a top surface of the thermally conductive core portion, wherein the support matrix comprises a thermally absorptive material and at least a portion of the array of thermally conductive fibers extend from at least one of a side surface of the support matrix and a bottom surface of the support matrix.

31. The subject cooling system of claim 28, wherein at least one thermally conductive core portion of the set of thermally conductive core portions comprises:

a compliant shell;

a support matrix comprising thermally adsorptive material enclosed within the compliant shell; and a cover flange extending around the support matrix and continuous with a top surface of the compliant shell, wherein at least the top surface and the cover flange have a thermal conductivity greater than 40 W/m*K.

32. The subject cooling system of claim 28, wherein at least one thermally conductive core portion of the set of thermally conductive core portions comprises:

a first support matrix comprising thermally absorptive material;

a second support matrix comprising thermally absorptive material, wherein the first support matrix and the second support matrix are enclosed within a compliant shell comprising a top surface having a thermal conductivity greater than 40 W/m*K, the compliant shell thermally coupling the first support matrix to the second support matrix; and a third support matrix disposed between the first support matrix and the second support matrix, wherein the third support matrix is formed from a different material than the first support matrix and the second support matrix.

33. The subject cooling system of claim 32, wherein the third support matrix is positioned in the compliant shell.

34. The subject cooling system of claim 32, wherein the third support matrix comprises a foam.

35. A person support system comprising:

a longitudinal frame comprising at least one side rail;

a support pad positioned on the longitudinal frame, the support pad comprising a thermally conductive core portion comprising a support matrix and at least one thermally conductive element; and a cooling source thermally coupled to the thermally conductive core portion through the at least one side rail with a connector comprising thermally conductive fibers, wherein the cooling source draws heat from the thermally conductive core portion through the at least one thermally conductive element and the thermally conductive fibers of the connector thereby cooling at least the thermally conductive core portion of the support pad, wherein:

the cooling source is a thermoelectric cooler and the thermally conductive core portion is thermally coupled to a cooling plate of the thermoelectric cooler; and the person support system further comprises a warming blanket thermally coupled to a heating plate of the thermoelectric cooler.

36. The person support system of claim 35, wherein the warming blanket comprises a flexible conduit receiving a warming fluid from the heating plate of the thermoelectric cooler by convection.

37. The person support system of claim 35, wherein the warming blanket comprises a thermally conductive element and the thermally conductive element of the warming blanket is thermally coupled to the heating plate of the thermoelectric cooler.

38. A person support system comprising:

a longitudinal frame comprising at least one side rail;

a support pad positioned on the longitudinal frame, the support pad comprising a thermally conductive core portion comprising a support matrix and at least one thermally conductive element; and a cooling source thermally coupled to the thermally conductive core portion through the at least one side rail with a connector comprising thermally conductive fibers, wherein the cooling source draws heat from the thermally conductive core portion through the at least one thermally conductive element and the thermally conductive fibers of the connector thereby cooling at least the thermally conductive core portion of the support pad, wherein:

the at least on thermally conductive element comprises thermally conductive particles suspended in the support matrix and at least one thermal transport layer thermally coupled to the support matrix and configured to conduct heat from the support matrix; and a number of thermally conductive particles per unit volume of the support matrix is greatest proximate a top surface of the thermally conductive core portion and decreases with increasing distance from the top surface of the thermally conductive core portion.

39. The person support system of claim 38, wherein the thermally conductive core portion further comprises thermally absorptive particles suspended in the support matrix.

40. The person support system of claim 39, wherein a number of thermally absorptive particles per unit volume of the support matrix is greatest at a top surface of the thermally conductive core portion and decreases with increasing distance from the top surface of the thermally conductive core portion.

41. A person support system comprising:
a longitudinal frame comprising at least one side rail;
a support pad positioned on the longitudinal frame, the support pad comprising a thermally conductive core portion comprising a support matrix and at least one thermally conductive element; and
a cooling source thermally coupled to the thermally conductive core portion through the at least one side rail with a connector comprising thermally conductive fibers, wherein the cooling source draws heat from the thermally conductive core portion through the at least one thermally conductive element and the thermally conductive fibers of the connector thereby cooling at least the thermally conductive core portion of the support pad, wherein:
the at least one thermally conductive element of the thermally conductive core portion comprises an array of thermally conductive fibers suspended in the support matrix and arranged to conduct heat away from a top surface of the thermally conductive core portion;
at least a portion of the array of thermally conductive fibers extend from at least one of a side surface of the support matrix and a bottom surface of the support matrix; and
the array of thermally conductive fibers comprises a first plurality of thermally conductive fibers and a second plurality of thermally conductive fibers, wherein the second plurality of thermally conductive fibers are arranged parallel to a top surface of the thermally conductive core portion.

42. The person support system of claim 41, wherein the first plurality of thermally conductive fibers are obliquely oriented with respect to the second plurality of thermally conductive fibers.

43. The person support system of claim 42, wherein the first plurality of thermally conductive fibers and the second plurality of thermally conductive fibers have different thermal conductivities and the thermal conductivity of the first plurality of thermally conductive fibers is greater than the thermal conductivity of the second plurality of thermally conductive fibers.

44. The person support system of claim 41, wherein the second plurality of thermally conductive fibers are arranged in the support matrix such that a density of the second plurality of thermally conductive fibers in the support matrix is greatest at a top surface of the thermally conductive core portion and decreases with increasing distance from the top surface of the thermally conductive core portion.

45. The person support system of claim 41, wherein:
the second plurality of thermally conductive fibers comprises thermally conductive fibers having different thermal conductivities; and
the second plurality of thermally conductive fibers are arranged in the support matrix such that fibers having relatively greater thermal conductivity are positioned closer to a top surface of the thermally conductive core portion than thermally conductive fibers having relatively lower thermal conductivity.

46. A person support system comprising:
a longitudinal frame comprising at least one side rail;
a support pad positioned on the longitudinal frame, the support pad comprising a thermally conductive core portion comprising a support matrix and at least one thermally conductive element;
a cooling source thermally coupled to the thermally conductive core portion through the at least one side rail with a connector comprising thermally conductive fibers, wherein the cooling source comprises thermally absorptive material and draws heat from the thermally conductive core portion through the at least one thermally conductive element and the thermally conductive fibers of the connector to the thermally absorptive material thereby cooling at least the thermally conductive core portion of the support pad; and
a control unit communicatively coupled to an input device and an RFID reader, the control unit comprising a processor and a non-transitory memory storing computer readable and executable instructions which, when executed by the processor, cause the control unit to:
receive an input indicative of a target temperature;
receive an accessory identification signal from the RFID reader indicative of an identity of an accessory; and
determine a recommended thermally absorptive material based on the target temperature and the identity of the accessory.

47. The person support system of claim 46, wherein the computer readable and executable instructions, when executed by the processor, further cause the control unit to determine a recommended time schedule for replacing the thermally absorptive material to achieve the target temperature.

* * * * *